US011844907B2

(12) United States Patent
Smith et al.

(10) Patent No.: US 11,844,907 B2
(45) Date of Patent: Dec. 19, 2023

(54) HUMIDIFIERS FOR RESPIRATORY APPARATUS

(71) Applicant: ResMed Pty Ltd, Bella Vista (AU)

(72) Inventors: Ian Malcolm Smith, Sydney (AU); Richard Llewelyn Jones, Sydney (AU); Hargopal Verma, Sydney (AU); Dimitri Marco Maurer, Gosford (AU); Jane Zona McHenry, Auckland (NZ)

(73) Assignee: ResMed Pty Ltd, Bella Vista (AU)

( * ) Notice: Subject to any disclaimer, the term of this patent is extended or adjusted under 35 U.S.C. 154(b) by 184 days.

(21) Appl. No.: 17/363,040

(22) Filed: Jun. 30, 2021

(65) Prior Publication Data

US 2021/0322712 A1 Oct. 21, 2021

Related U.S. Application Data

(63) Continuation of application No. 16/243,953, filed on Jan. 9, 2019, now Pat. No. 11,077,281, which is a (Continued)

(51) Int. Cl.
*A61M 16/16* (2006.01)
*A61M 16/10* (2006.01)
(Continued)

(52) U.S. Cl.
CPC .......... *A61M 16/16* (2013.01); *A61M 16/109* (2014.02); *A61M 16/1075* (2013.01);
(Continued)

(58) Field of Classification Search
CPC .. A61M 16/00; A61M 16/10; A61M 16/1045; A61M 16/1075; A61M 16/109;
(Continued)

(56) References Cited

U.S. PATENT DOCUMENTS 3,912,125 A 10/1975 Acklin
4,051,205 A 9/1977 Grant
(Continued)

FOREIGN PATENT DOCUMENTS

GB 2 293 325 A 3/1996
WO WO 2010/031126 A1 3/2010

OTHER PUBLICATIONS

U.S. Appl. No. 61/522,763, filed Aug. 12, 2011.

*Primary Examiner* — Colin W Stuart
(74) *Attorney, Agent, or Firm* — Nixon & Vanderhye P.C.

(57) ABSTRACT

A positive airway device is configured to deliver a pressurized flow of humidified respiratory gas to a patient's airways and includes a flow generator with a blower portion and a docking portion laterally adjacent to the blower portion. The docking portion is separated from the blower portion by a divider and comprises a cavity configured to laterally receive a humidifier tub. The humidifier tub comprises a first tub subsection with an air inlet opening and an air outlet opening and a second tub subsection. A flange extending outwardly from an outer surface of the humidifier tub forms a transition between the first and second tub subsections. The humidifier tub is configured so that when the humidifier tub is fully received by the docking portion, the first tub subsection is enclosed within the cavity and the second tub subsection remains outside the cavity.

25 Claims, 53 Drawing Sheets

Related U.S. Application Data continuation of application No. 13/723,236, filed on Dec. 21, 2012, now Pat. No. 10,213,573.

(60) Provisional application No. 61/579,298, filed on Dec. 22, 2011.

(51) Int. Cl.
*A61M 16/14* (2006.01)
*A61M 16/00* (2006.01)

(52) U.S. Cl.
CPC ......... *A61M 16/14* (2013.01); *A61M 16/0066* (2013.01); *A61M 16/162* (2013.01); *A61M 16/164* (2014.02); *A61M 16/165* (2014.02)

(58) Field of Classification Search
CPC ............ A61M 16/108; A61M 16/1085; A61M 16/1095; A61M 16/14; A61M 16/16; A61M 16/162; A61M 16/164; A61M 16/165; A61M 16/167; A61M 16/168; F24F 3/14; F24F 3/147; F24F 6/00; F24F 6/02; F24F 2006/008
See application file for complete search history.

(56) References Cited

U.S. PATENT DOCUMENTS

| | | | |
|---|---|---|---|
| 4,086,305 A | 4/1978 | Dobritz | |
| 4,098,853 A | 7/1978 | Brown | |
| 4,152,379 A * | 5/1979 | Suhr | A61M 16/16 261/DIG. 65 |
| 4,529,867 A | 7/1985 | Velnosky | |
| 4,546,491 A | 10/1985 | Beaussant | |
| 5,231,979 A * | 8/1993 | Rose | A61M 16/16 128/200.24 |
| 5,247,604 A | 9/1993 | Chiu | |
| 6,397,841 B1 * | 6/2002 | Kenyon | A61M 16/08 128/204.14 |
| 6,554,260 B1 | 4/2003 | Lipscombe et al. | |
| 6,669,626 B1 | 12/2003 | Mcdonough | |
| 6,874,771 B2 | 4/2005 | Birdsell et al. | |
| 7,096,864 B1 | 8/2006 | Mayer et al. | |
| 8,020,551 B2 | 9/2011 | Virr et al. | |
| 8,555,879 B2 * | 10/2013 | Potharaju | A61M 16/109 128/203.12 |
| 8,701,662 B2 | 4/2014 | Pujol | |
| 10,213,573 B2 | 2/2019 | Smith et al. | |
| 2003/0066526 A1 * | 4/2003 | Thudor | A61M 16/161 128/203.26 |
| 2004/0020487 A1 | 2/2004 | Koch et al. | |
| 2004/0055597 A1 | 3/2004 | Virr | |
| 2004/0060559 A1 | 4/2004 | Virr | |
| 2007/0034638 A1 | 2/2007 | Zeiron | |
| 2007/0079826 A1 * | 4/2007 | Kramer | A61M 16/109 128/200.14 |
| 2007/0157928 A1 | 7/2007 | Pujol | |
| 2007/0169776 A1 * | 7/2007 | Kepler | A61M 16/107 128/200.14 |
| 2007/0193580 A1 * | 8/2007 | Feldhahn | A61M 16/021 128/204.18 |
| 2008/0310994 A1 * | 12/2008 | O'Donnell | A61M 16/109 128/203.14 |
| 2009/0056714 A1 | 3/2009 | Cortez, Jr. et al. | |
| 2010/0154796 A1 * | 6/2010 | Smith | A61M 16/0875 239/311 |
| 2011/0155132 A1 | 6/2011 | Virr et al. | |
| 2019/0143070 A1 | 5/2019 | Smith et al. | |

* cited by examiner

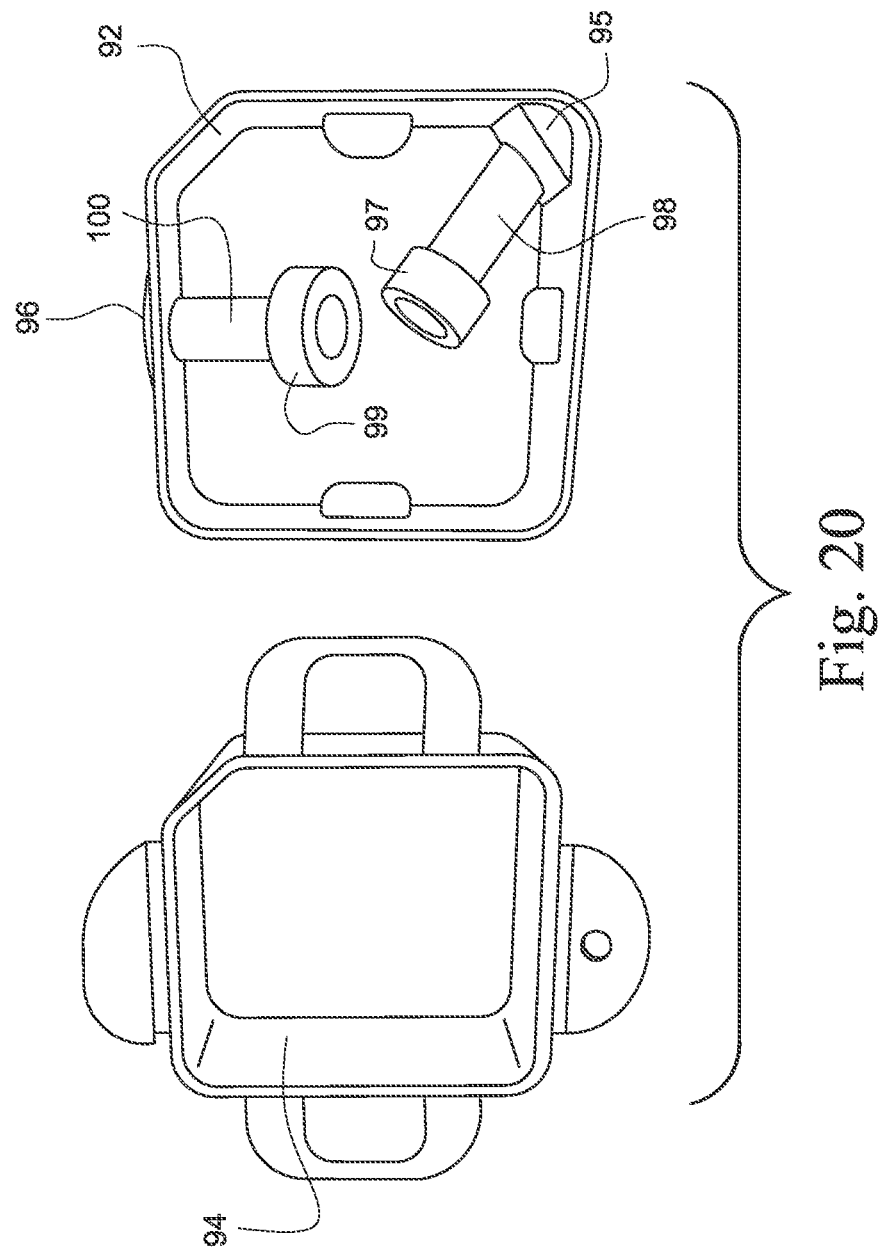

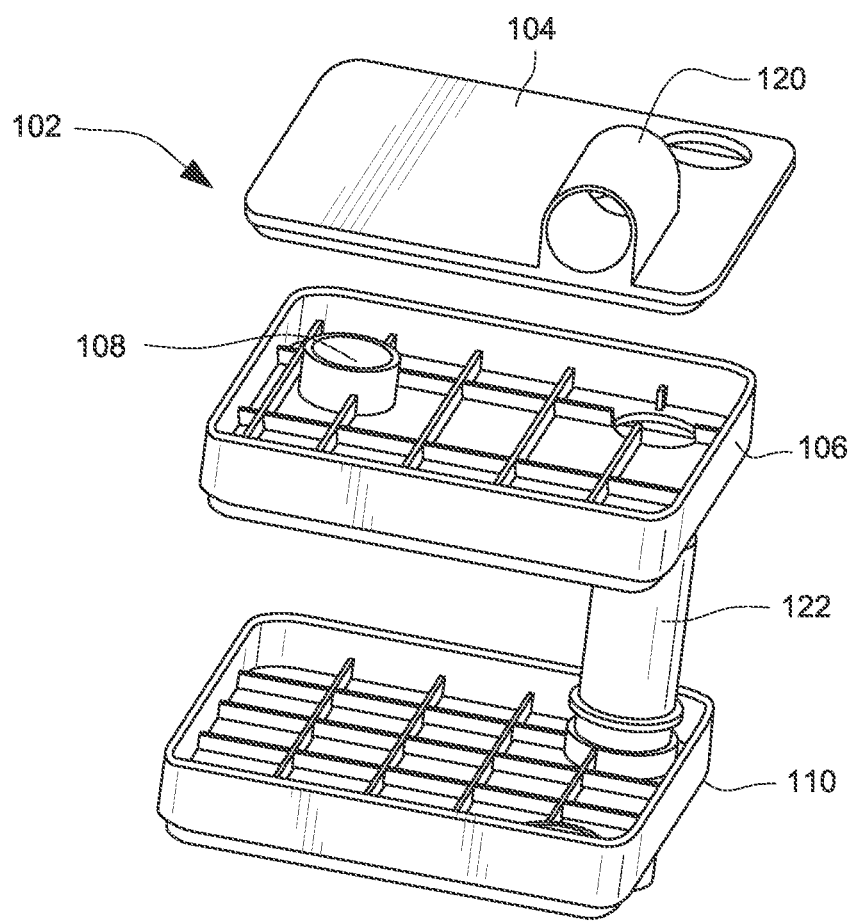
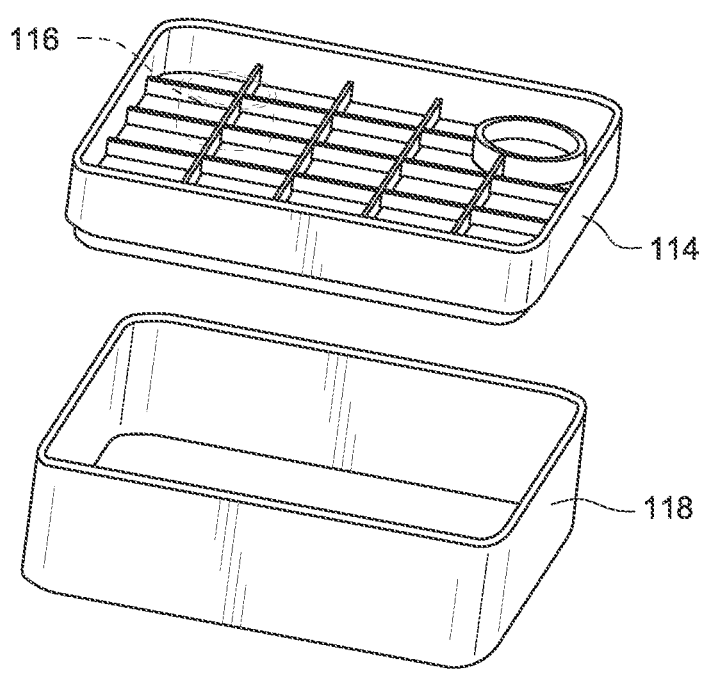
Fig. 28

HUMIDIFIERS FOR RESPIRATORY APPARATUS

CROSS REFERENCE TO RELATED APPLICATION

This application is a continuation of U.S. application Ser. No. 16/243,952, filed Jan. 9, 2019, which is a continuation of U.S. application Ser. No. 13/723,236, filed Dec. 21, 2012, now U.S. Pat. No. 10,213,573, which claims priority to U.S. Application No. 61/579,298, filed Dec. 22, 2011, the entire contents being incorporated herein by reference.

FIELD OF THE TECHNOLOGY

The present technology relates to humidifiers for respiratory apparatus, for example humidifiers for respiratory apparatus for treating sleep disordered breathing (SDB) such as obstructive sleep apnea (OSA).

BACKGROUND OF THE TECHNOLOGY

Respiratory apparatuses commonly have the ability to alter the humidity of the breathable gas in order to reduce drying of the patient's airway and consequent patient discomfort and associated complications. The use of a humidifier placed between the flow generator and the patient mask produces humidified gas that minimizes drying of the nasal mucosa and increases patient airway comfort. In addition in cooler climates, warm air applied generally to the face area in and about the mask is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub.

SUMMARY OF THE TECHNOLOGY

One aspect of the technology relates to a humidifier having a reduced heated water volume ensuring faster warm up times and/or less thermal inertia. This allows more accurate and/or faster controllability of the water temperature with reduced thermal overshoots in the control system. This has advantages if, for example, a climate control feedback system is used to control humidity output.

Another aspect of the technology relates to a humidifier having a reduced air path and thus a more compact humidifier volume for a given reservoir capacity. In current humidifiers, more dead space is required to reduce the risk of water getting into the flow generator when the device is not level. For example, the required dead space may be equal to the water volume and the humidifier may be designed to be tilted by at least 90° in any direction, and there must be spare volume for the water to flow into before it can enter the flow generator. According to a further aspect of the technology, in a bird feeder type humidifier with a tilt-control system only a thin water layer is heated so the air path just has to accommodate a relatively small amount of water before entering the flow generator in tilt conditions.

Still another aspect of the technology relates to promoting evaporation by providing for the air to flow rapidly, in a relatively thin layer over the water surface. This concept naturally allows a thin, high speed air layer to be designed into the humidifier.

According to an example of the present technology, a tub for a humidifier comprises an inner tub configured to hold a supply of water; an outer tub configured to receive the inner tub, the outer tub comprising a bottom and a cavity being formed between the bottom and the inner tub when the inner tub is received in the inner tub; and a valve configured to control a flow of the supply of water from the inner tub to the cavity, wherein the valve is closed to prevent the flow when the inner tub is received in a first position in the outer tub and open to permit the flow when the inner tub is received in a second position in the outer tub.

According to another example of the present technology, a humidifier for a respiratory apparatus, comprises a tub as described in the preceding paragraph and a dock configured to receive the tub. According to a still another example, the dock comprises a lid movable between an open position in which the dock is configured to receive the tub and a closed position in which the dock is configured to hold the tub. According to a still further example, the lid is configured to move the inner tub from the first position to the second position when the lid is moved from the open position to the closed position. An air lock is formed between the supply of water and the lid when the lid is in the closed position.

According to another example of the present technology, a tub for a humidifier comprises a tub base configured to contain a supply of water; a tub lid connectable to the tub base, the tub lid comprising an inlet for a flow of breathable gas and an outlet for a flow of humidified breathable gas; a inlet tube connected to the inlet; and an outlet tube connected to the outlet, wherein the inlet tube and the outlet tube are configured to float on a surface of the supply of water contained in the tub and prevent a flow of water out of the inlet and/or the outlet if the tub is tilted and/or rotated.

According to yet another example of the present technology, a tub for a humidifier comprises a lid including an inlet for a flow of breathable gas and an outlet for a flow of humidified breathable gas; a bottom chamber configured to contain a supply of water exposed to the flow of breathable gas; and at least one intermediate level between the lid and the bottom chamber, the intermediate level being configured to contain a predetermined amount of water exposed to the flow of breathable gas.

According to still another example of the present technology, a humidifier comprises a first tub configured to contain a supply of water and having a first size; a second tub configured to contain a supply of water and having a second size different than the first size; and a dock configured to receive either the first tub or the second tub, the dock including an inlet configured to receive a flow of breathable gas and direct it into the tub received in the dock and an outlet for a flow of a humidified flow of breathable gas.

According to another example of the present technology, a tub for a humidifier is configured to contain a supply of water and comprises an inlet for receiving a flow of breathable gas; an outlet for the flow of breathable gas; and a movable vane provided between the inlet and the outlet, the movable vane being configured to direct a selectable portion of the flow of breathable gas from the inlet to the outlet without contacting a surface of the supply of water.

According to a further example of the present technology, a tub for a humidifier comprises a top lid portion including an inlet conduit for a flow of breathable gas and an outlet conduit for a humidified flow of breathable gas; a middle portion including a top portion having an inlet hole configured to receive the flow of breathable gas from the inlet of the top lid portion and an outlet hole configured to receive the flow of humidified breathable gas; and a bottom portion, wherein the bottom portion and the middle portion form a reservoir for a supply of water, the top portion of the middle portion and the top lid portion forming a top chamber separated from the reservoir, and the inlet hole and outlet hole are positioned to prevent water from flowing out of the reservoir into the top chamber if the tub is tilted or rotated.

According to further examples of the present technology, a respiratory apparatus comprises a flow generator configured to generate a flow of breathable gas and a humidifier as disclosed and described herein. The flow generator may generate the flow of breathable gas at a pressure of 2-30 cm H$_2$O, typically 8-12 cm H$_2$O. According to a further example of the present technology, a tub for a humidifier includes an adjustable section configured to expand and retract to increase or decrease a volume of the tub. For example, the tub can be expandable to increase the volume of the tub by about 10-100%. The tub may further include an inlet for receiving a flow of breathable gas and an outlet for the flow of breathable gas.

The adjustable section may be, for example, a concertina-type section or collapsible and expandable folds, a sliding section with opposing walls that overlap and are configured to slidably move with respect to each other or any other type of arrangement capable of increasing and/or decreasing the volume of the tub. In the case of a sliding section, the adjustable section comprises a seal positioned between opposable walls that are slidably movable with respect to each other. The seal may be any type of seal such as, for example, an o-ring or an overmold seal.

The tub may further include a locking device to lock the adjustable section at a particular position. The locking device may be any device capable of locking the adjustable section at a particular position such as, for example, an adjustable length latch. In addition, the locking device may lock the adjustable section at a finite number of discrete positions or at an infinite number of positions so that the tub is expandable at a finite number of discrete increments or at an infinite number of increments.

The tub may also include an inlet tube configured to receive the flow of breathable gas, wherein the inlet tube has a length sufficient to prevent water from flowing from the inlet tube to the inlet of the dock if the humidifier is tilted and/or rotated. The inlet tube may be adjustable and configured to expand and contract in combination with the size of the tub to prevent water from flowing from the inlet tube to the inlet of the dock if the humidifier is tilted and/or rotated.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 20 is a view of the tub lid and floating tubes of FIG. 19 and a tub base;

FIG. 28 is an exploded assembly view of the humidifier of FIG. 22;

DETAILED DESCRIPTION OF ILLUSTRATED EXAMPLES

Figure 1:
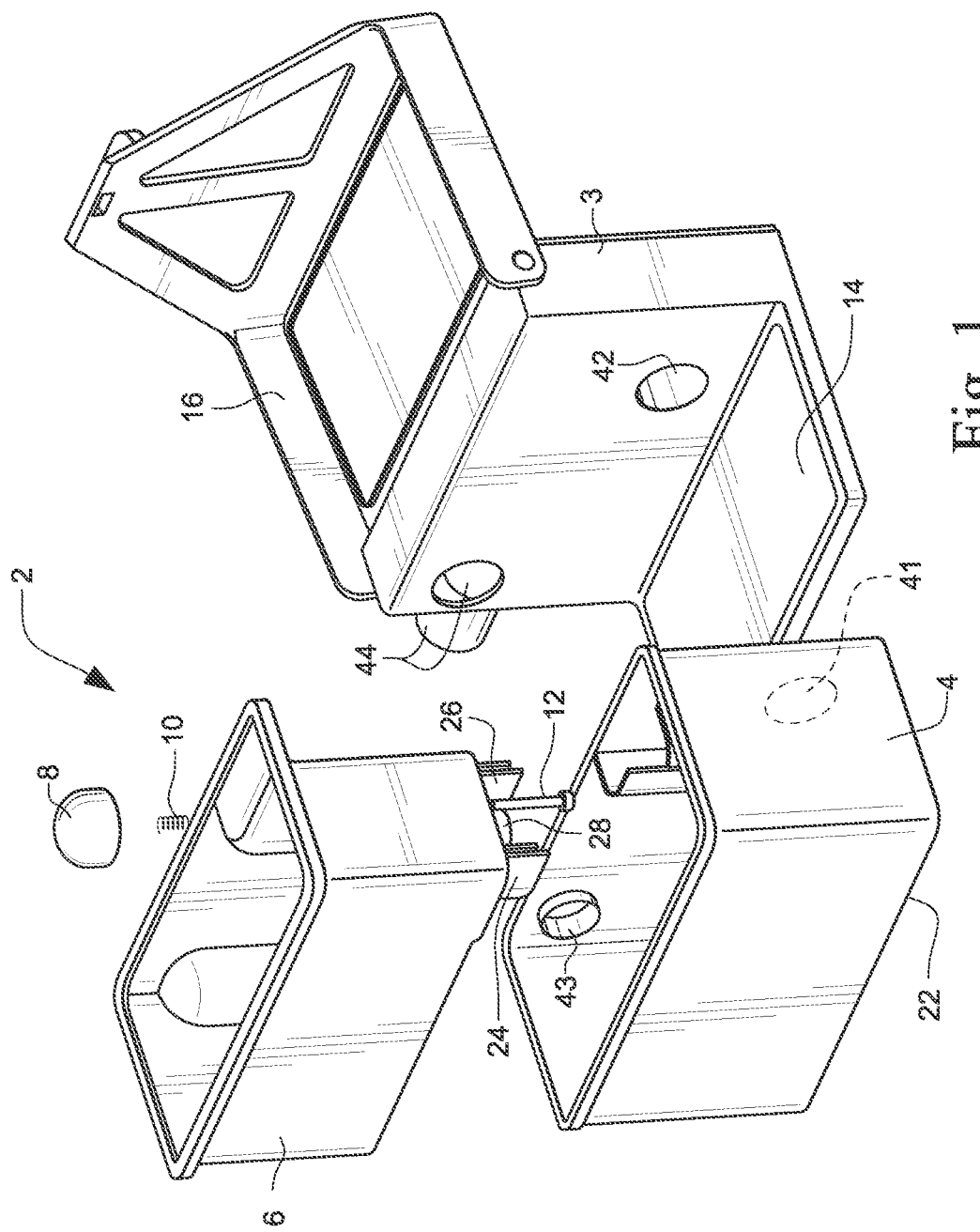
FIG. 1 is an exploded assembly view of a humidifier according to an example of the technology.

The following description is provided in relation to several examples which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

Bird Feeder Type Humidifier

One example of a "bird feeder" type humidifier has a water reservoir feeding a smaller volume of heated water in the humidifier air path through a nozzle. The level of water in the smaller heated volume is dictated by the set height of a nozzle i.e. water flows from the reservoir until the level in the lower heated cavity reaches the nozzle, thus creating an air lock. See, for example, U.S. Pat. No. 7,096,864, the entire contents of which are incorporated herein by reference.

The air lock ensures that the pressure above the water is lower than the pressure outside of the air lock. This lower pressure region is referred to as a vacuum. As water is lost by evaporation, the water level falls breaking the air lock which allows more water to flow into the heated cavity. The water level then rises until the air lock is once again created. With one nozzle, the water level can fall a few millimeters below the nozzle height as a meniscus maintains the air lock. Once the meniscus can not support the air lock, air can flow into the reservoir and the heated air cavity refills to the set height of the nozzle.

The humidifier of U.S. Pat. No. 7,096,864 has a second, lower depth, nozzle which the water can flow through to maintain the fluid level. This provides more consistent filling of the heated air cavity. With a second, lower depth, nozzle the pressure head of the reservoir maintains a constant level of water, dictated by the height of the primary nozzle without the level fluctuations present if just a single nozzle is used. The second nozzle controls water flow into the heated cavity and the water pressure head in the reservoir above maintains a constant liquid level, controlled by the primary nozzle, and prevents a meniscus from forming on the primary nozzle. The water level in the heated cavity is therefore controlled more consistently than with a single nozzle.

A disadvantage with bird feeder type humidifiers is that if they are not level then the air lock may be lost allowing water to flow freely into the heated cavity. This water will then flow into the flow generator of the respiratory apparatus and/or the patient tube (i.e. the air delivery hose or conduit). The water may also "spit out" as the air path may be totally or partially blocked with water.

Another difficulty with current bird feeder type humidifiers is filling the humidifier with water. For the bird feeder principle to work the vacuum is required above the water, but this must be removed to fill the water tank.

Tilt Spill Control

Referring to FIGS. 1-11, a humidifier 2 according to an example comprises a cradle 3. The cradle 3 may comprise a heater plate 14, although it should be appreciated that the cradle 3 may include an integrated heater. The cradle 3 also comprises a lid 16 that may be pivotally connected to the cradle. The cradle 3 may be part of a flow generator that is configured to generate a flow of breathable gas at a pressure of 2-30 cm $H_2O$, or the cradle 3 may be separate from and/or connectable to the flow generator.

The cradle 3 is configured to receive a tub. The tub comprises an outer tub or tub base 4 and an inner reservoir or inner tub 6. The inner reservoir or inner tub 6 includes a valve 8 that controls water flow from the inner reservoir or inner tub 6 to a cavity 40 that is configured to be heated by the heater plate 14 of the cradle 3. The inner reservoir or inner tub 6 is configured to contain a supply of water 20 for humidifying a flow of breathable gas through the humidifier 2. The inner reservoir or inner tub 6 is configured to be received in the outer tub or tub base 4 so that a cavity 40 is provided between the inner reservoir or inner tub 6 and the outer tub 4. The cavity 40 may be heated by the heater plate 14. The bottom 22 of the outer tub 4 may be heat conductive. For example, the bottom 22 may be formed of metal and the remainder of the outer tub 4 may be formed of, for example, a plastic material.

Figure 5:
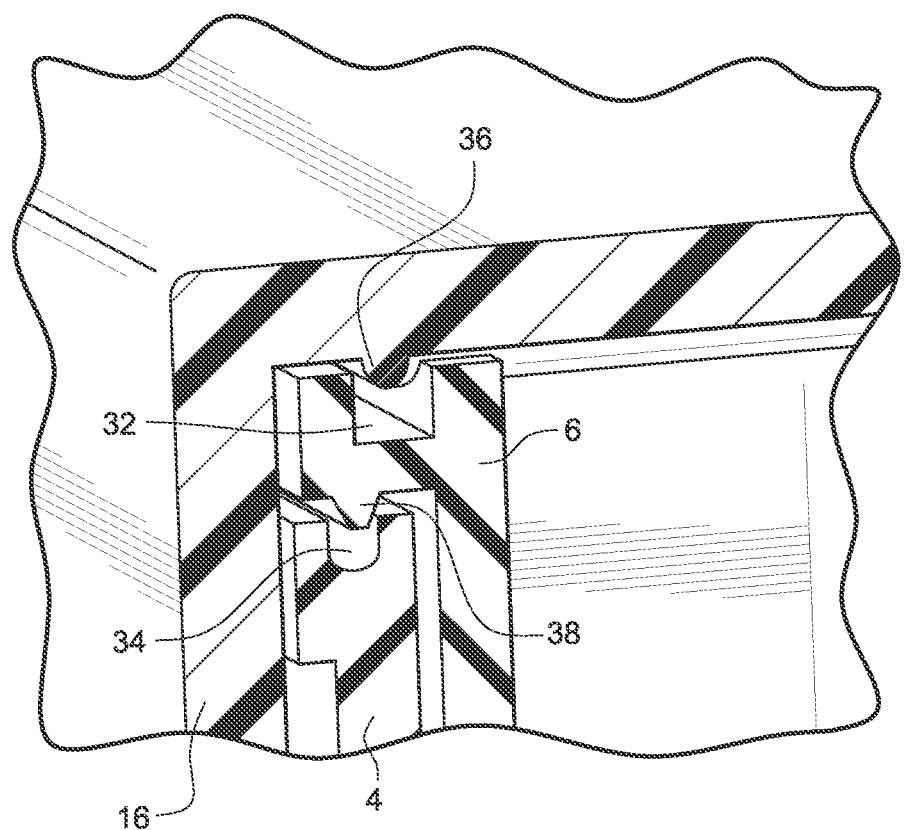
FIG. 5 is a detailed cross section view of the outer tub or tub base, the inner reservoir or tub, and the lid, with the lid in the closed position.

The valve 8 controls the flow of water 20 from the inner tub 6 to the outer tub 4. The lid 16 of the cradle 3 may be pivoted from the open position shown in FIG. 3 to the closed position shown in FIG. 2. In the closed position the lid 16 engages the inner tub 6 as shown in FIG. 5 and pushes the inner tub 6 into engagement with the outer tub 4. As shown in FIG. 5, the lid 16 may include a lid rib or lid projection 36 that is configured to engage a seal (not shown) provided in a first groove 32 that extends around the perimeter of the top of the inner tub 6. The perimeter of the top of the inner tub 6 may also comprise a tub rib or tub projection 38 extending around the perimeter that is configured to engage a seal (not shown) provided in a second groove 34 that extends around a perimeter of the top of the outer tub 4. The seals may be, for example, overmoulded to the inner and outer tubs 6, 4, or the inner and/or outer tubs 6, 4 may be formed of, for example, flexible thermoplastic elastomer (TPE). In the closed position of the lid 16 shown in FIG. 5, the tub is sealed at the top and at the lid 16 to prevent water from spilling out of the tub from between the inner and outer tubs 6, 4 and between the inner tub 6 and the lid 16.

Figure 2:
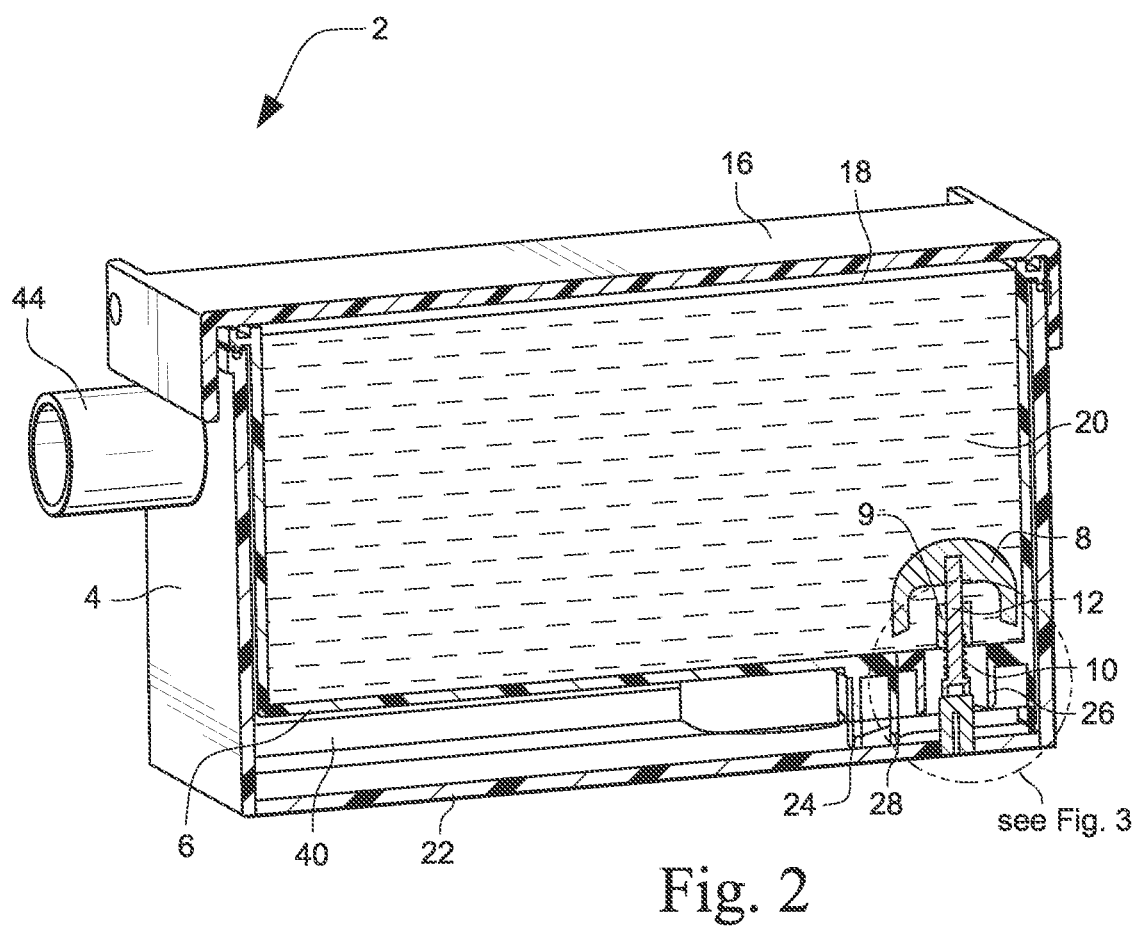
FIG. 2 is a cross section view of the humidifier of FIG. 1 with the lid in a closed position and the inner reservoir or tub filled with water.
Figure 3:
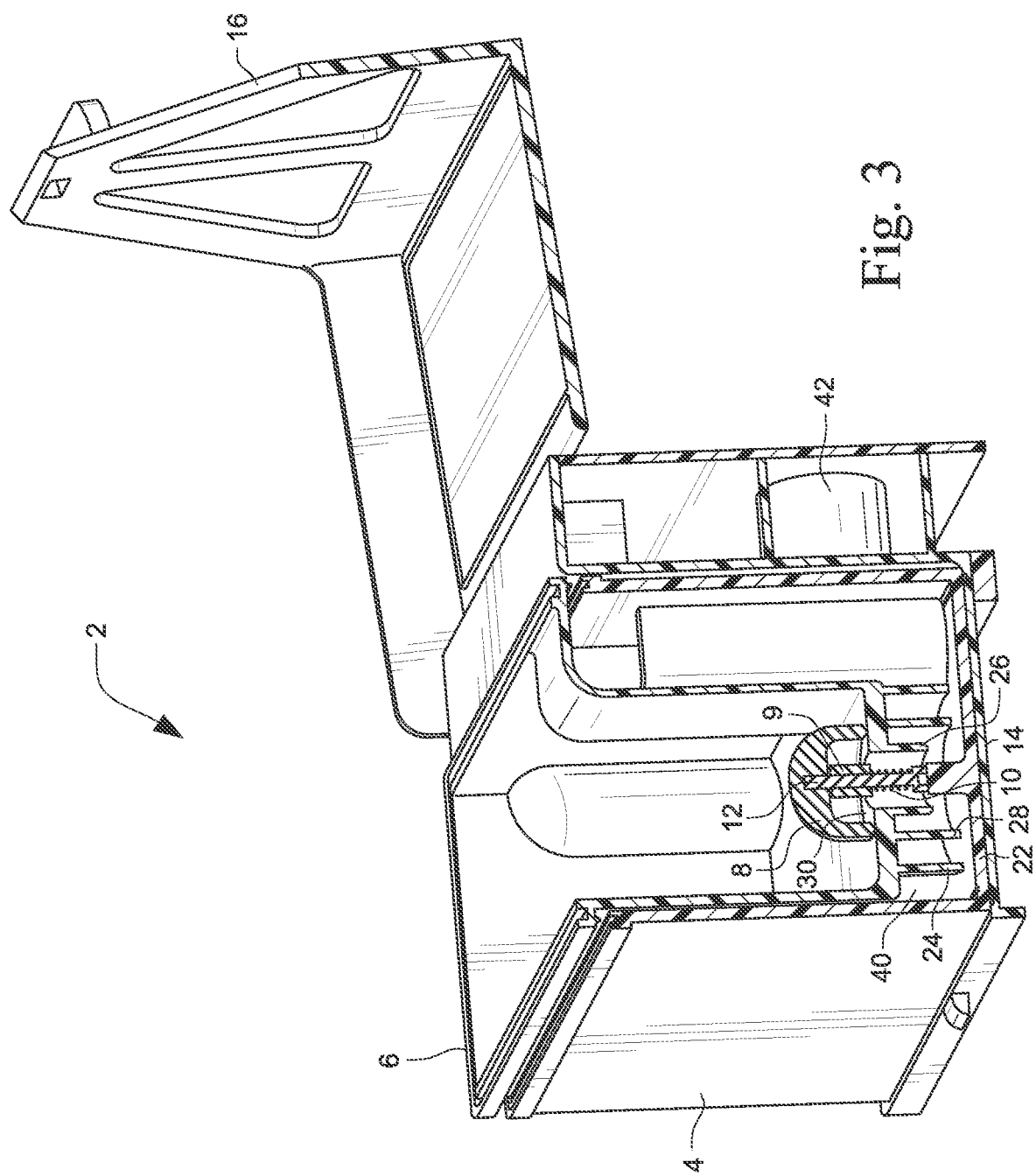
FIG. 3 is a cross section view of the humidifier of FIG. 1 with the lid in an open position and the inner reservoir or tub empty.

Referring to FIG. 2, in the closed position of the lid 16, an air lock 18 is created between the top surface of the water 20 and the sealed lid 16. The air lock 18 creates a vacuum above the water 20 that prevents the free flow of the water 20 into the cavity 40. The valve 8 seals a primary or first nozzle 26 and a secondary or second nozzle 28 when the lid 16 is in the open position shown in FIG. 3. When the lid 16 is pivoted to the closed position shown in FIG. 2, the valve 8 is lifted off the valve seat 30 of the inner tub 6 and water 20 may flow from the inner tub 6 to the cavity 40 between the inner tub 6 and the bottom 22 of the outer tub 4. The primary (or first) nozzle 26 maintains a constant water level in the cavity 40 and the secondary (or second) nozzle 28 ensures a consistent water level by controlling the flow of water into the cavity 40.

Figure 4:
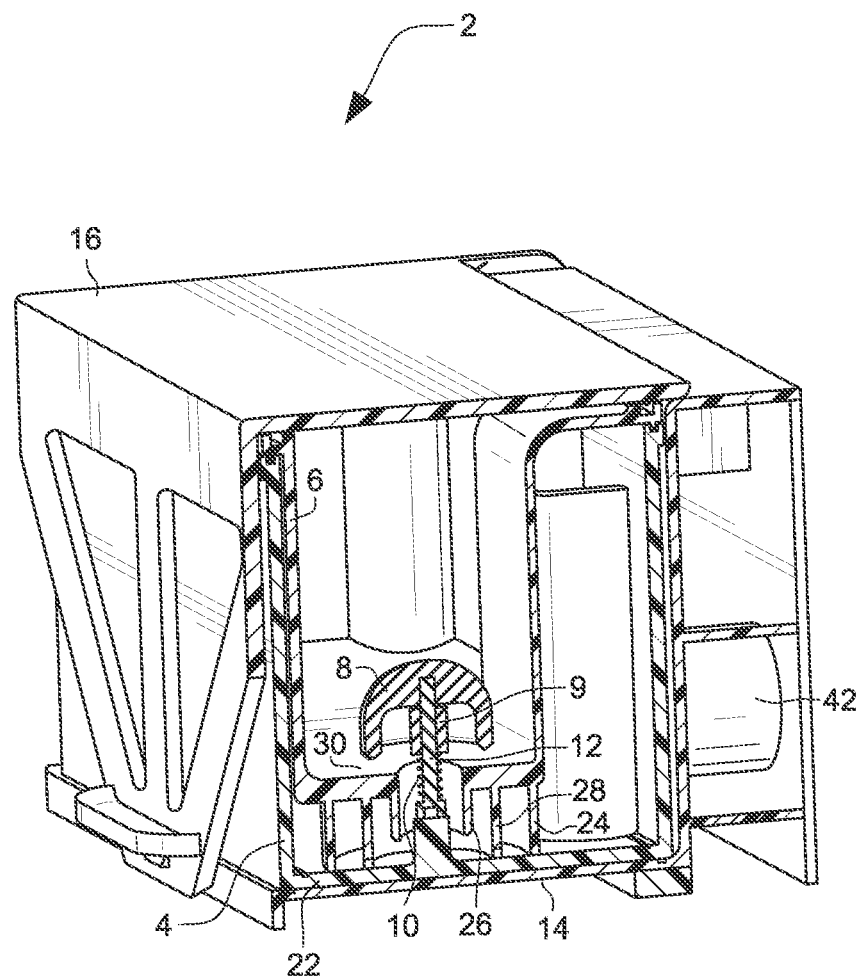
FIG. 4 is a second cross section view of the humidifier of FIG. 1 with the lid in the closed position.

The valve 8 comprises a valve spring 10 provided on a valve stem 12. A spring stop 9 is provided between the valve 8 and the valve spring 10. In the open position of the lid 16 shown in FIG. 3, the valve spring 10 pushes up the inner tub 6 and the valve 8 is engaged with the valve seat 30 (i.e. the valve 8 is closed) and the inner tub 6 may be removed from the outer tub 4 for filling with water 20. The inner tub 6 may also be filled with water 20 in-situ (i.e. without being removed from the outer tub 4) as the air flow path is sealed off from the water. The force of the valve spring 10 is sufficient to maintain the valve 8 closed even when the inner tub 6 is full of water. When the inner tub 6 is filled with water 20 and placed into the outer tub 4 and the lid 16 is closed as shown in FIGS. 2 and 4, the inner tub 6 is engaged by the lid 16 and pushed down against the bias of the valve spring 10. The valve 8 is lifted off of the valve seat 30 and the water 20 may flow through the primary and secondary nozzles 26, 28 into the cavity 40 until the water level reaches the level of the primary nozzle 26. A flow of breathable gas enters the heated cavity 40 through an inlet tube 42 in the cradle 3 and through an inlet aperture 41 and the humidified flow of breathable gas exits through an outer tub outlet 43 of the outer tub 4 in communication with an outlet tube 44 of the cradle 3.

The inner tub 6 includes a tilt control labyrinth 24 provided on a bottom of the inner tub 6 around the primary and secondary nozzles 26, 28. Referring to FIGS. 6-11, which illustrate a different tub configuration from FIGS. 1-5, when the tub is tilted, water in the cavity 40 flows through an opening 25 in the tilt control labyrinth 24 until the tilt labyrinth water level 48 is at a set height of the primary nozzle 26. When the humidifier 2 is tilted on the inlet end (i.e. with the inlet tube 42 at the bottom) as shown in FIG. 7, the water cannot flow out of the inlet tube 42 or the outlet tube 44. The tilt control labyrinth 24 maintains the air lock 18 and prevents the water 20 in the inner reservoir 6 from emptying into the cavity 40. The cavity 40 has a volume sufficient to allow water to flow into the cavity 40 in all orientations before it can flow out of the inlet tube 42 or the outlet tube 44.

Figure 8:
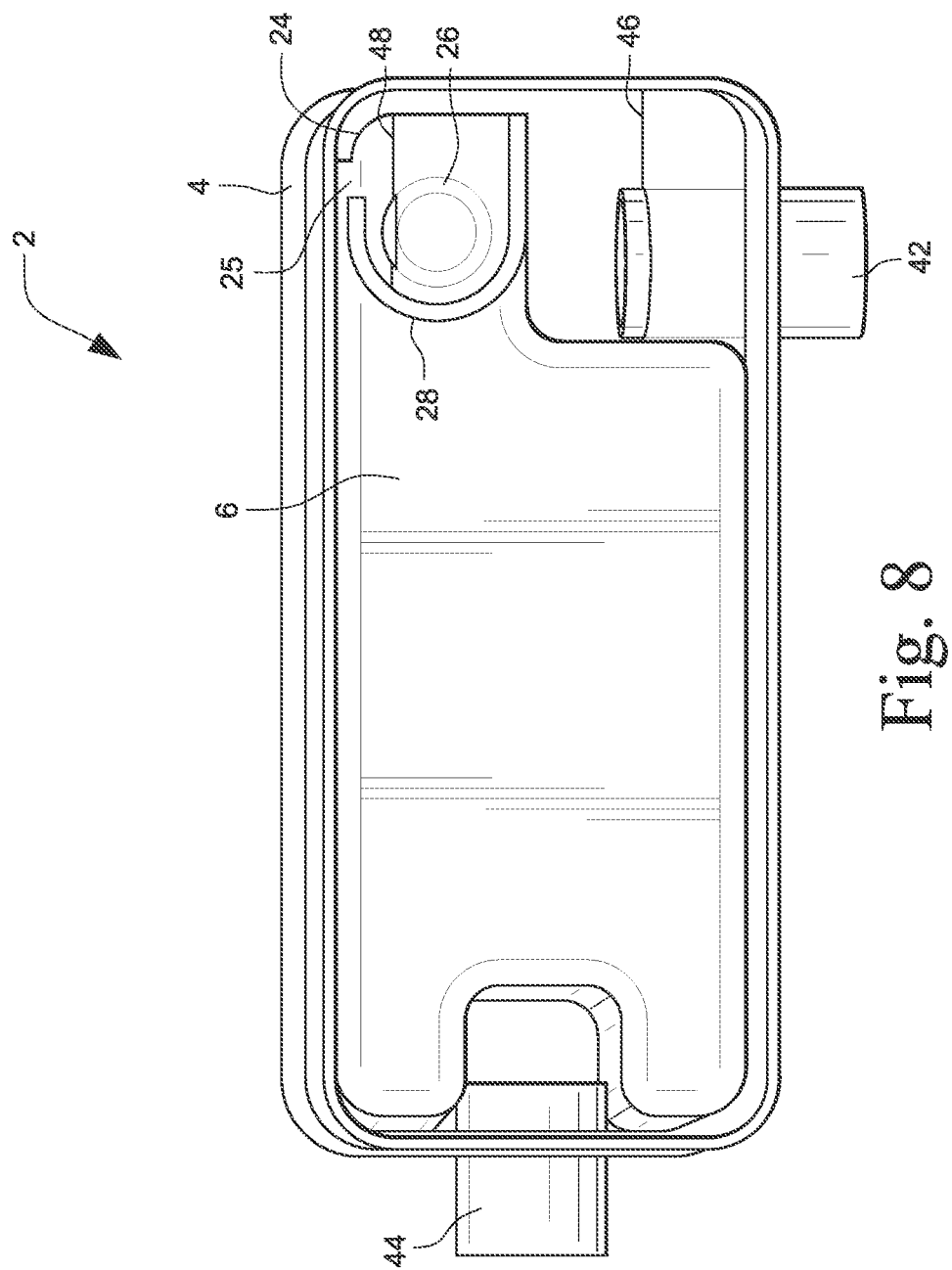
FIG. 8 is a view of the humidifier of FIG. 1 tilted in a second orientation.

As shown in FIG. 8, when the humidifier is tilted on its side so that the inlet tube 42 is facing down, the tilt labyrinth water level 48 in the tilt control labyrinth 24 and the cavity water level 46 in the cavity 40 prevent the water from flowing out of the inlet tube 42 and the outlet tube 44.

Figure 9:
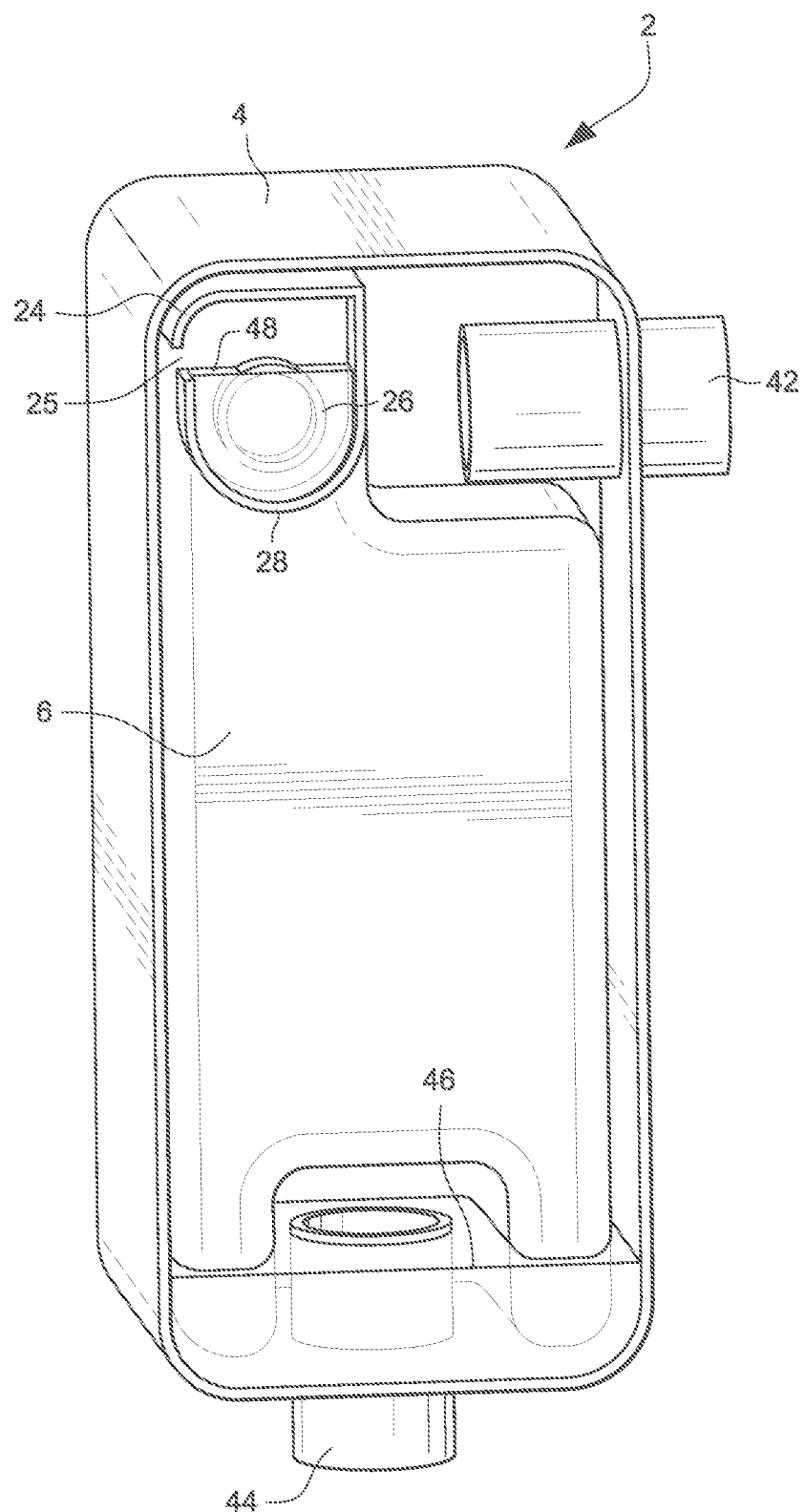
FIG. 9 is a view of the humidifier of FIG. 1 tilted in a third orientation.

When the humidifier is tilted on the outlet end (i.e. with the outlet tube 44 on the bottom) as shown in FIG. 9, the tilt labyrinth water level 48 in the tilt control labyrinth 24 and the cavity water level 46 in the cavity 40 prevent the water from flowing out of the outlet tube 44 and the inlet tube 42. The tilt labyrinth water level 48 in the tilt control labyrinth 24 maintains the air lock 18 in the inner reservoir 6.

Figure 10:
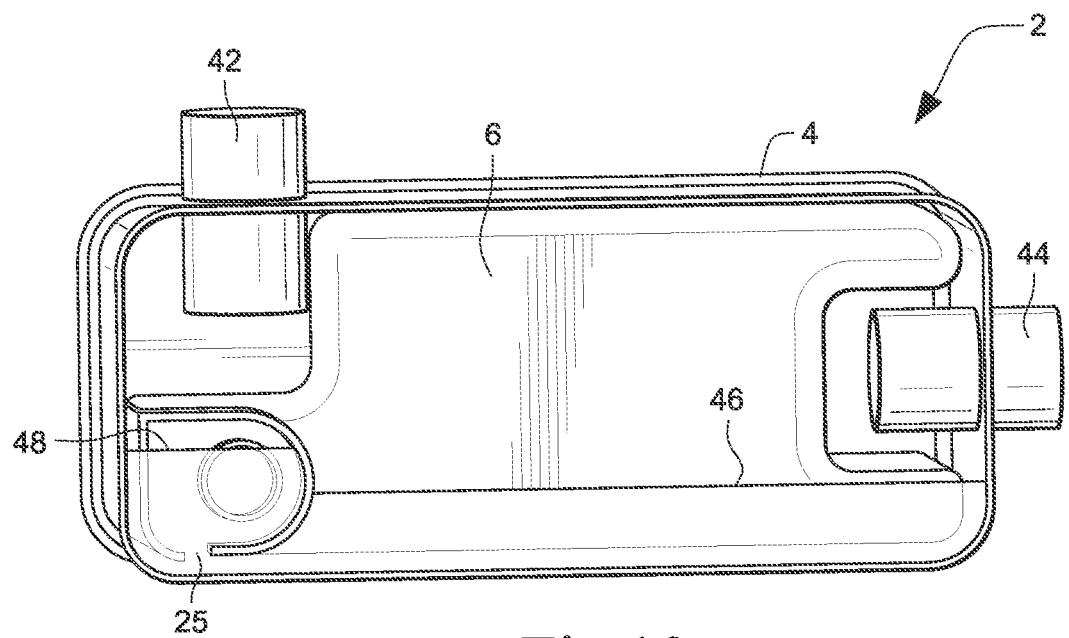
FIG. 10 is a view of the humidifier of FIG. 1 tilted in a fourth orientation.
Figure 11:
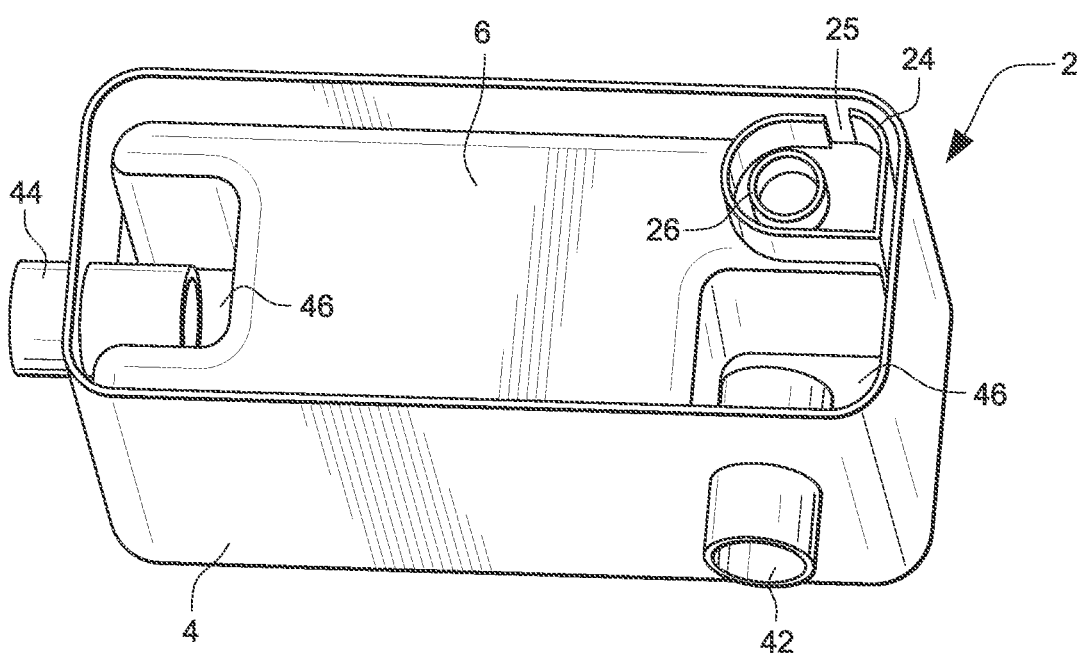
FIG. 11 is a view of the humidifier of FIG. 1 tilted in a fifth orientation.
Figure 12:
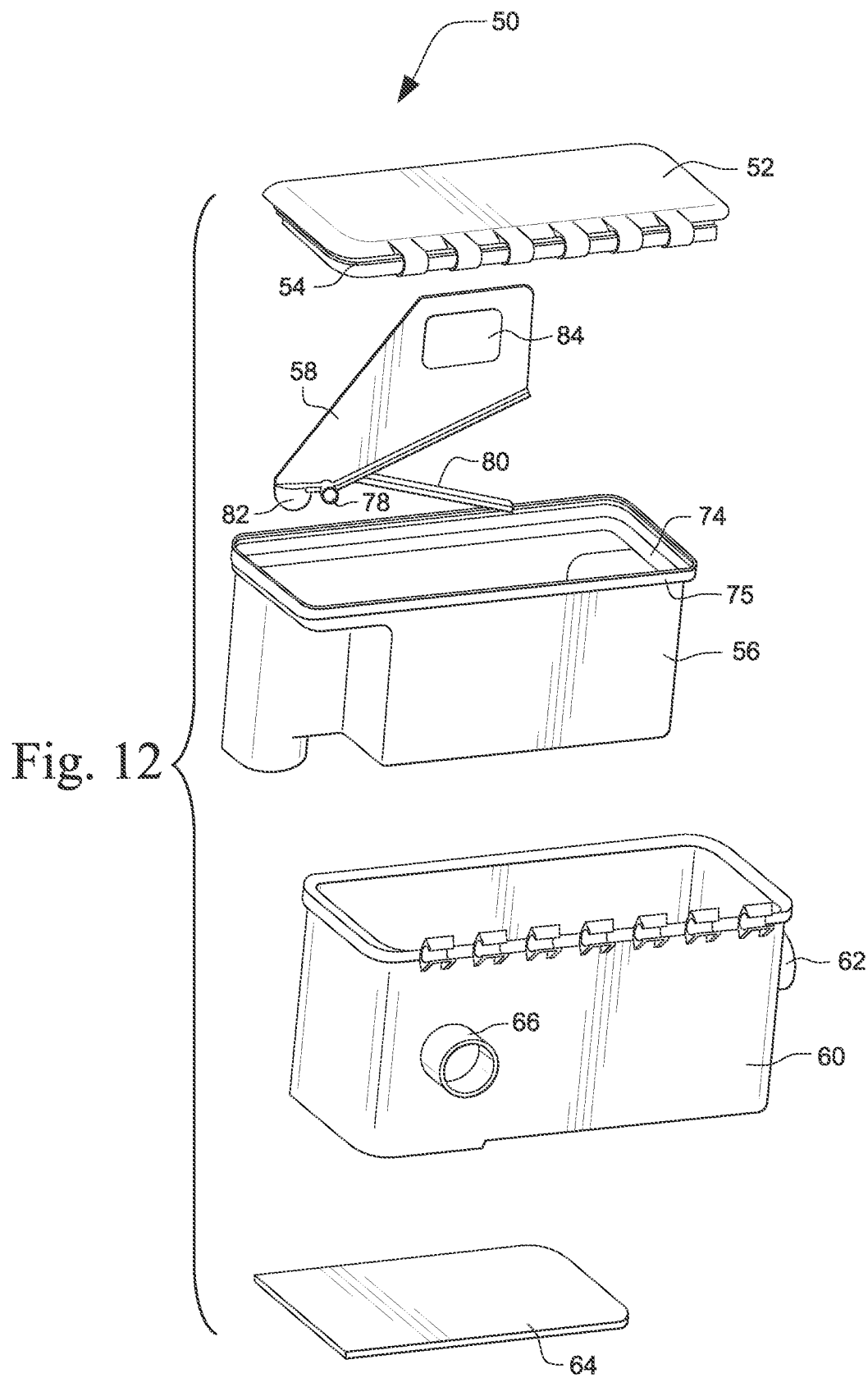
FIG. 12 is a view of a humidifier according to another example of the technology.

When the humidifier is tilted on its side with the inlet tube 42 facing up as shown in FIG. 10, the tilt labyrinth water level 48 in the tilt control labyrinth and the cavity water level 46 in the cavity 40 prevent water from flowing out of the inlet tube 42 and the outlet tube 44. When the humidifier is tilted upside down as shown in FIG. 11, the cavity water level 46 in the cavity 40 prevents water from flowing out of the inlet tube 42 and the outlet tube 44. Although the humidifier is shown in FIGS. 6-11 in various tilted conditions, it should be appreciated that the tilt control labyrinth 24 prevents water flowing into the inlet or outlet tubes 42, 44 in positions intermediate to those shown in FIGS. 6-11, for example at all positions intermediate the positions shown in FIGS. 7 and 10, and at all positions intermediate the positions shown in FIGS. 8 and 9.

Referring to FIGS. 12-18, a humidifier 50 according to another example comprises an inner reservoir or inner tub 56 configured to be received in an outer tub or tub base 60. A cavity 55 is provided between the inner tub 56 and the outer tub 60 (see FIGS. 17 and 18). Water stored in the inner tub 56 may flow through a water feed nozzle 70 provided in the inner tub 56 into the cavity 55. The outer tub 60 may have a heat conductive base or heater plate 64 provided at the bottom of the outer tub 60 to heat the water in the cavity 55. A tub seal 75 may be provided between the inner tub 56 and the outer tub 60. A lid 52 may be pivotably connected to the outer tub 60. A lid seal 54 may be provided on the lid 52 and an inner seal 74 may be provided on the inner tub 56. The seals 75, 54 and 74 seal the outer tub 60 and the inner tub 56 and the inner tub 56 and the lid 52, respectively.

A rocker valve (or rocker arm) 58 is provided in the inner tub 56 to control the flow of water from the inner tub 56 through the water feed nozzle 70 into the cavity 55. The rocker valve 58 (or rocker arm) comprises an axle 78 that is engaged with rocker valve supports 76 provided in the inner tub 56. The axle 78 may snap into the rocker valve supports 76 and be removable, for example to clean the rocker valve 58 and the inner tub 56. The rocker valve 58 may also include a handle 84 to permit the lift and carry of the inner reservoir or inner tub 56 out of the outer tub 60. The handle 84 may also serve as a water level indicator.

The rocker valve 58 is pivotable in the inner tub 56 about the axle 78. A rocker valve biasing element 80 is provided to the rocker valve 58 to bias the rocker valve 58 into a closed position shown in FIG. 17 when the lid 52 is in an open position. It should be appreciated that the rocker valve biasing element 80 may be a resilient element that is, for example, integrally formed with the rocker valve 58, or provided separately, such as a leaf spring or a coil spring that is provided in the inner tub 56 for engagement with the rocker valve 58. In the valve closed position, a valve element 82 of the rocker valve 58 is engaged with a valve seat 86 in the inner tub 56 to close the water feed nozzle 70. When the lid 52 is pivoted from the open position shown in FIG. 17 to the closed lid position shown in FIG. 18, the lid 52 engages the top 88 of the rocker valve 58 and pivots the rocker valve 58 from the valve closed position shown in FIG. 17 to the valve open position shown in FIG. 18. In the valve open position shown in FIG. 18, water may flow from the inner tub 56 through the water feed nozzle 70 into the cavity 55. A flow of breathable gas may enter the cavity 55 through an air flow inlet or inlet tube 62 and the humidified air flow may exit the humidifier through an outlet tube 66.

The inner tub 56 comprises a breather tube 72 to maintain the air lock between the water in the inner reservoir or inner tub 56 and the lid 52. The breather tube 72 also provides for air to travel to the top air pocket portion of the reservoir instead of bubbling through the water volume, when the air lock is broken to release water into the cavity 55. This may be advantageous as air bubbling through the water volume may be noisy and cause patient discomfort. The inner tub 56 also comprises a tilt control labyrinth 68 around the nozzle 70 that prevents water in the cavity 55 from flowing out through the air flow inlet or inlet tube 62 and/or outlet tube 66 in a manner similar to that disclosed with respect to FIGS. 6-11.

Figure 6:
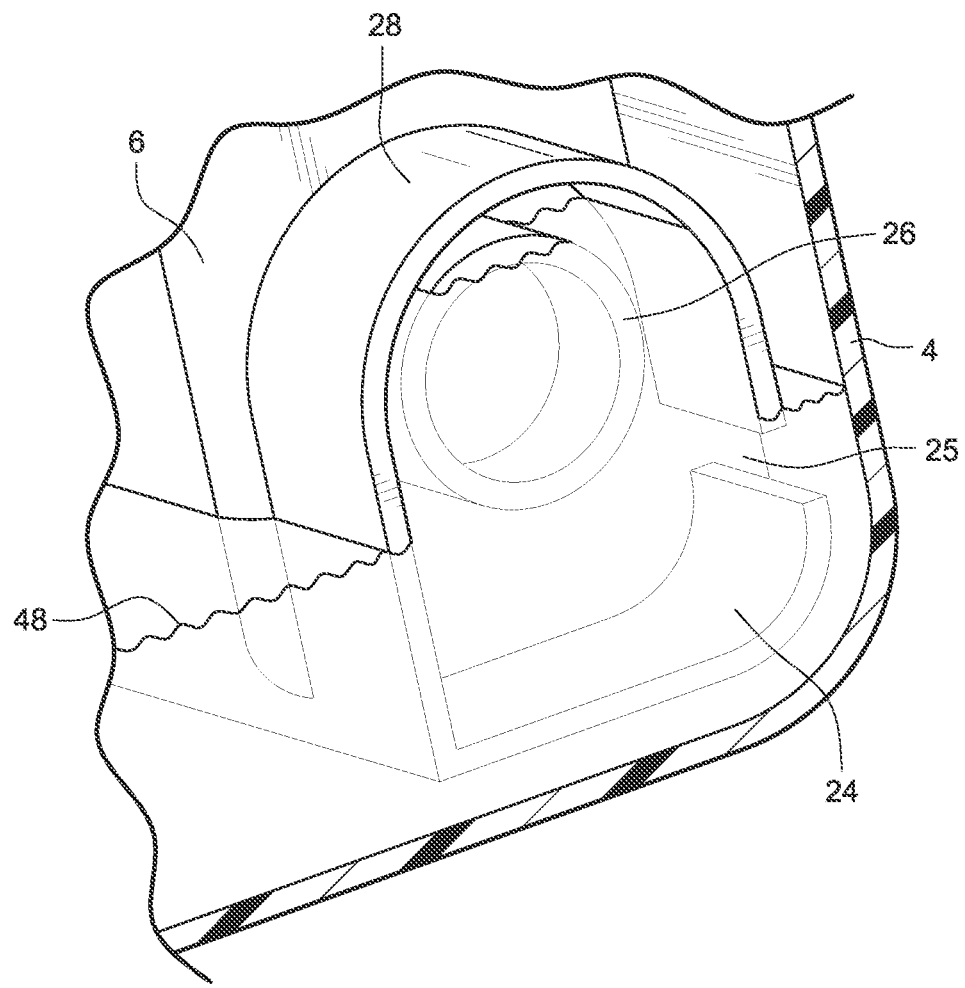
FIG. 6 is a cross section view of the bottom of the outer tub or tub base exposing the primary nozzle, the secondary nozzle, and the tilt control labyrinth of the inner reservoir or tub.
Figure 7:
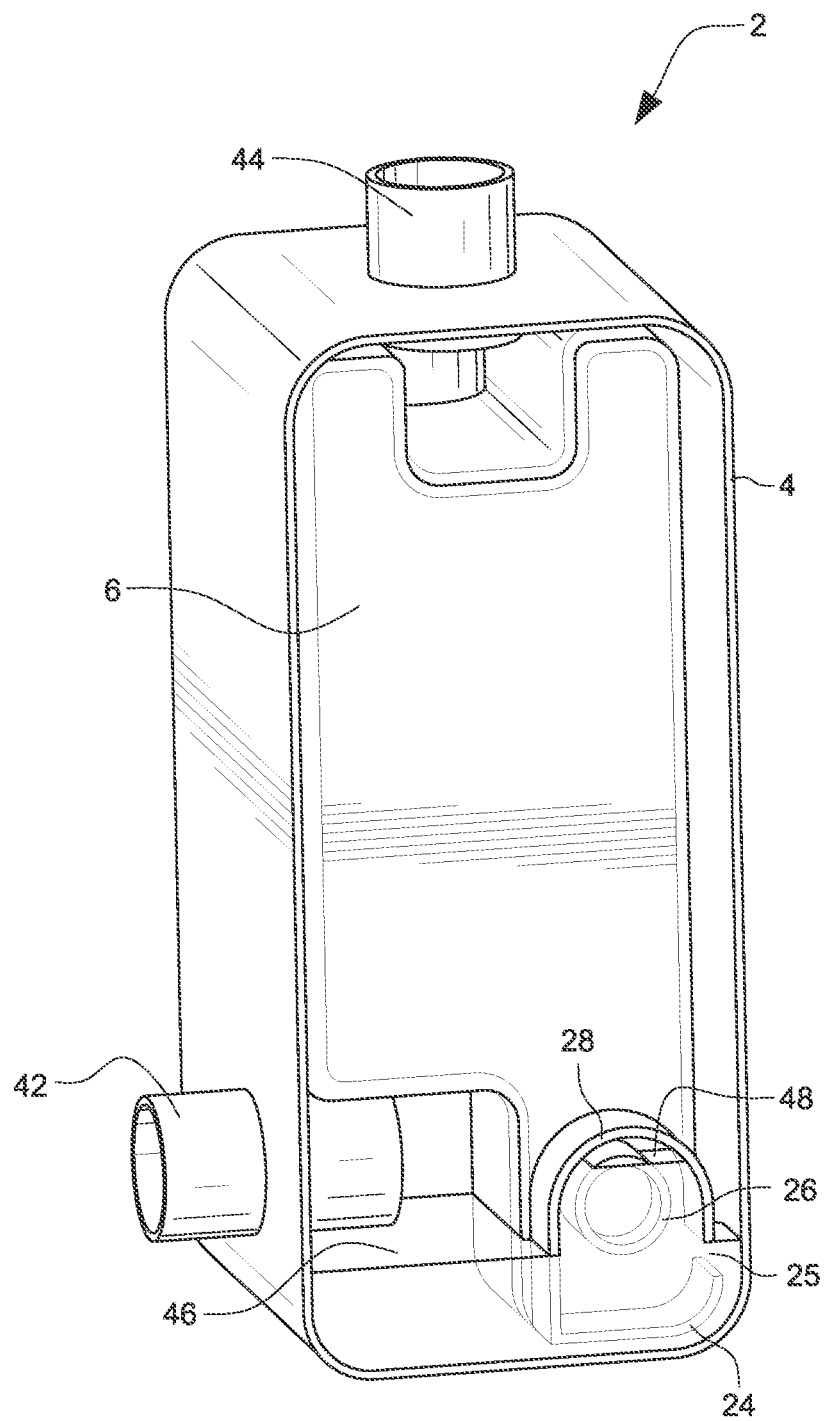
FIG. 7 is a view of the humidifier of FIG. 1 tilted in a first orientation.
Figure 13:
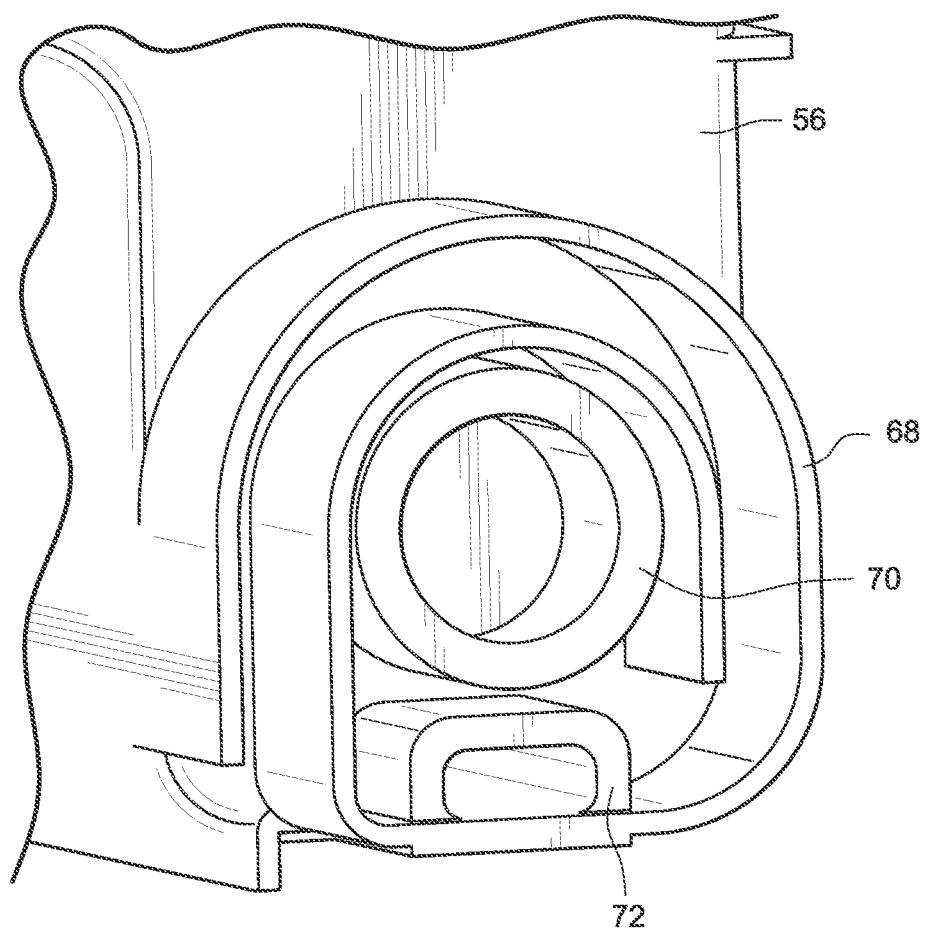
FIG. 13 is a view of a water feed nozzle, breather tube and tilt control labyrinth of the humidifier of FIG. 12.
Figure 14:
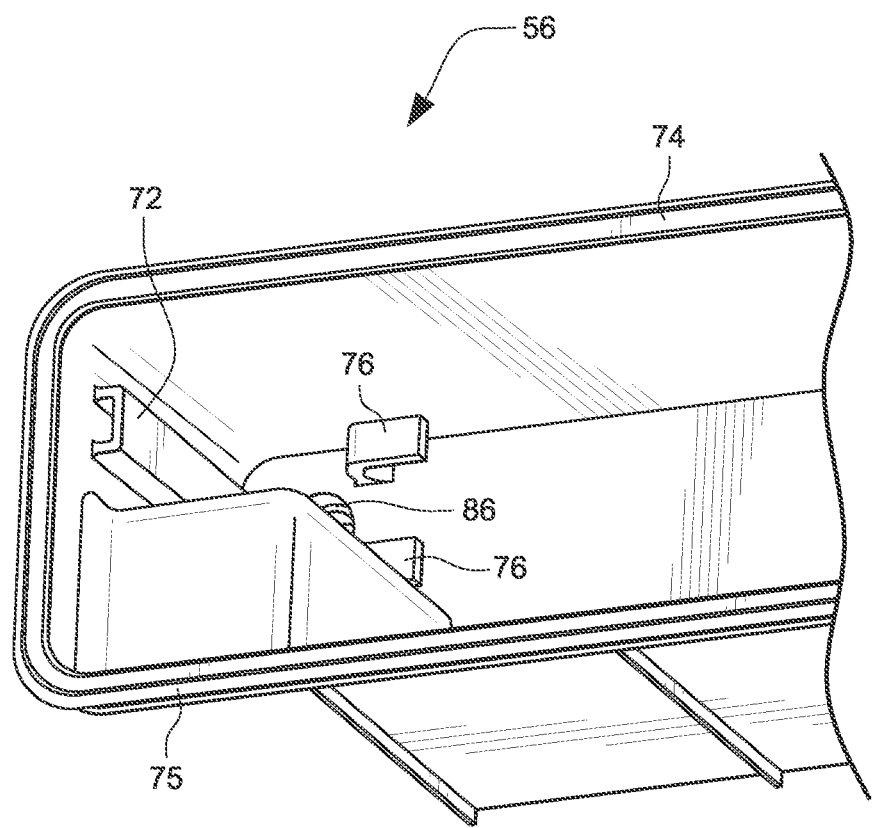
FIG. 14 is a view of an inner reservoir or tub of the humidifier of FIG. 12.
Figure 15:
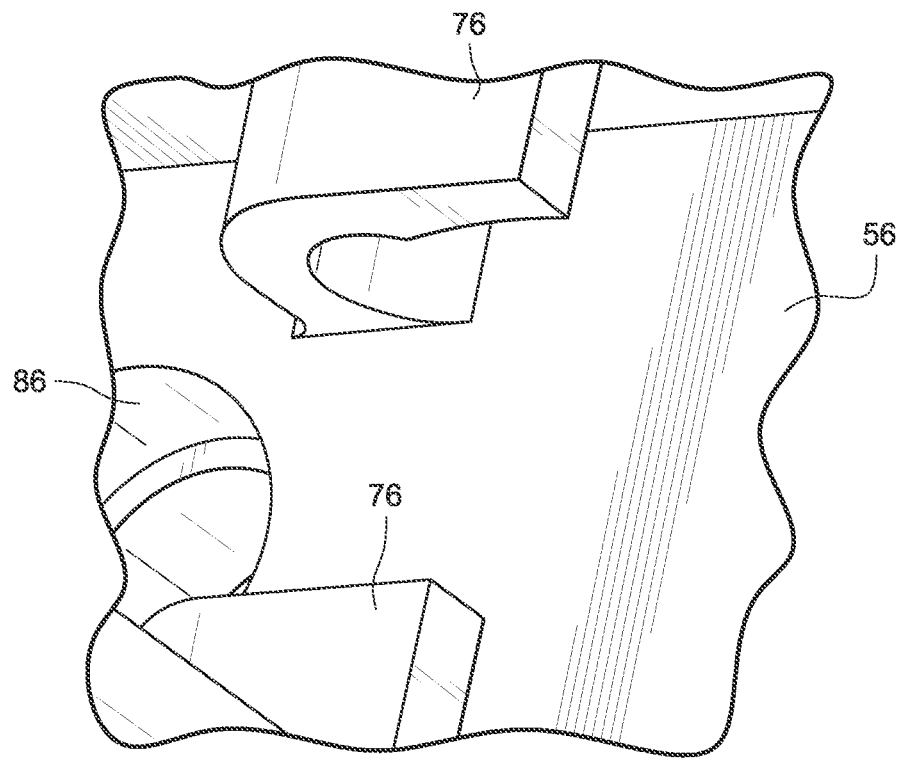
FIG. 15 is a detailed view of a valve support of the inner reservoir or tub of FIG. 14.
Figure 16:
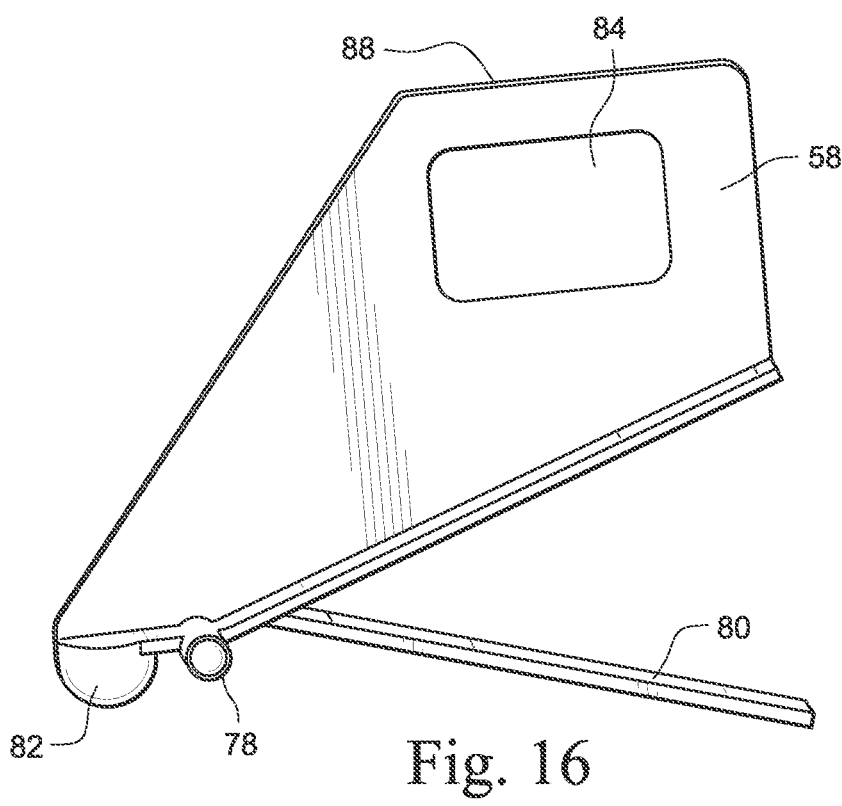
FIG. 16 is a view of a rocker valve of the humidifier of FIG. 12.
Figure 17:
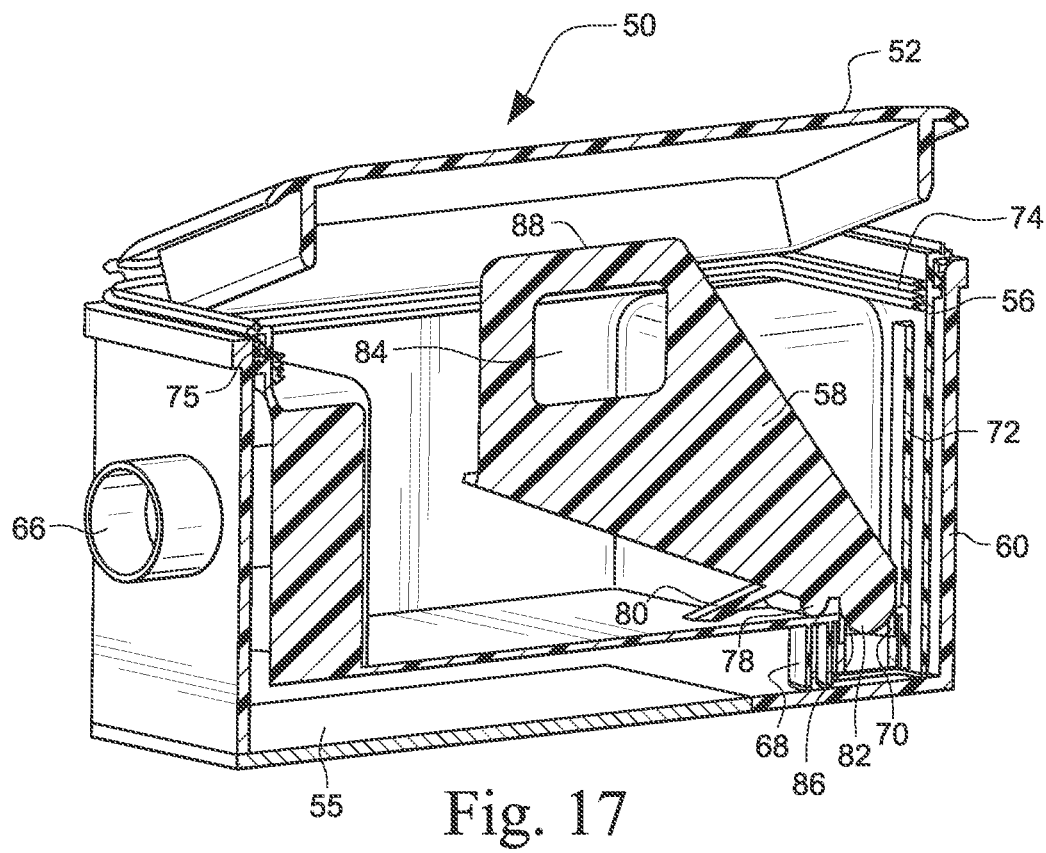
FIG. 17 is a cross section view of the humidifier of FIG. 12 with the lid in an open position and the valve closing the water feed nozzle.
Figure 18:
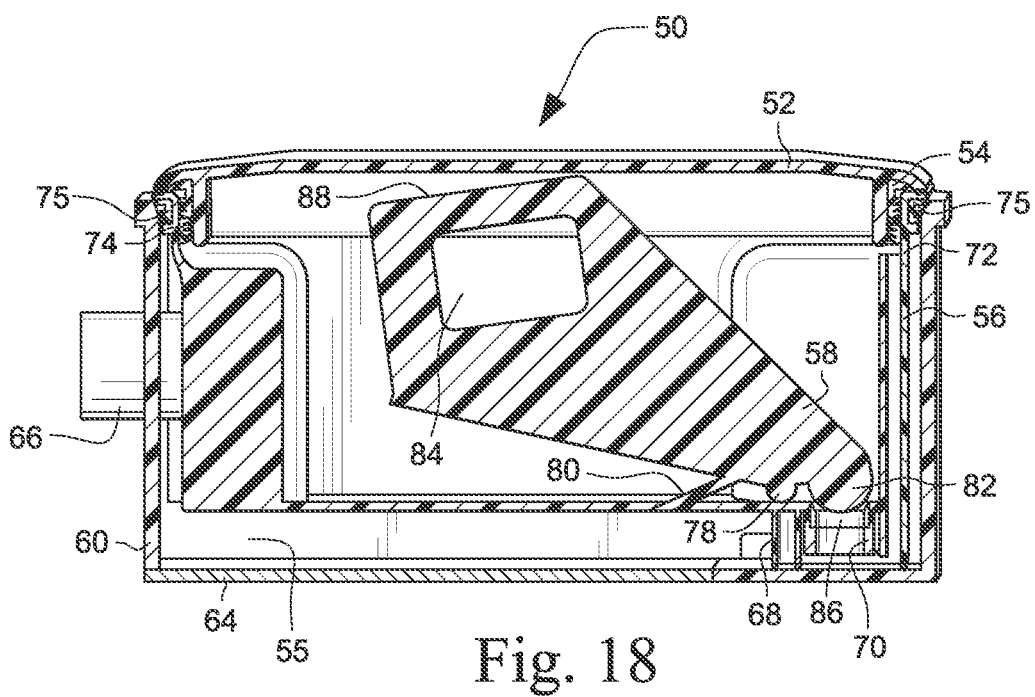
FIG. 18 is a cross section view of the humidifier of FIG. 12 with the lid in a closed position and the valve opening the water feed nozzle.

As shown in FIGS. 6 and 13, walled portions are provided surrounding the primary nozzle 26 or water feed nozzle 70. In FIG. 6, the walled portion comprises second nozzle 28 and tilt control labyrinth 24. In FIG. 13, the walled portion comprises tilt control labyrinth 68. The walled portions provide a means for trapping water and preventing water from flowing out, for example when the humidifier is tilted. The walled portions may comprise a plurality of walls, or a singular wall extending in a generally circular configuration as shown in FIG. 13 to surround the water feed nozzle 70. It is envisaged that the walled portions may be of the same height extending from the bottom of the inner tub 56, or alternatively may have differing heights along its length. Alternatively, the walled portions may extend from the outer tub 60 towards the inner tub 56 and surrounding the primary nozzle 26 or water feed nozzle 70. Other alternative configurations of walled portions for trapping water and/or providing tilt protection are also envisaged.

Humidifier with Floating Tubes Tilt Control

Figure 19:
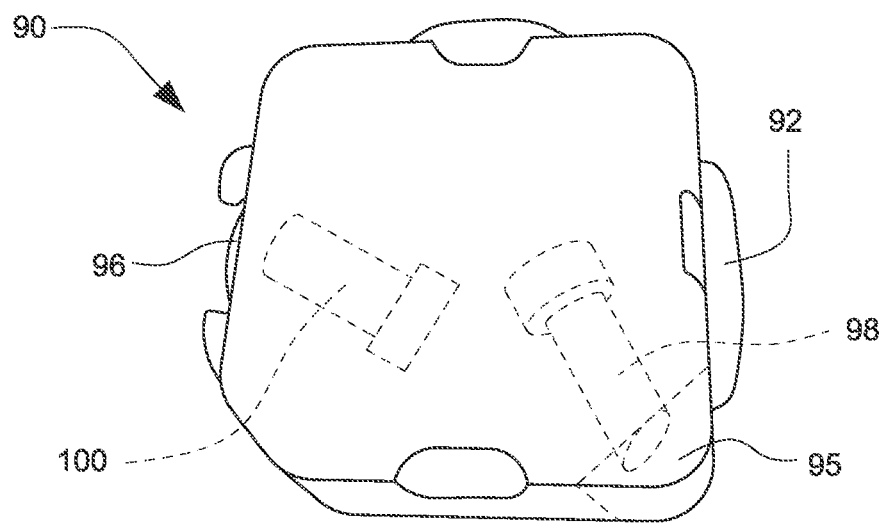
FIG. 19 is a view of a tub lid including a pair of floating tubes of a humidifier according to another example of the technology.
Figure 21:
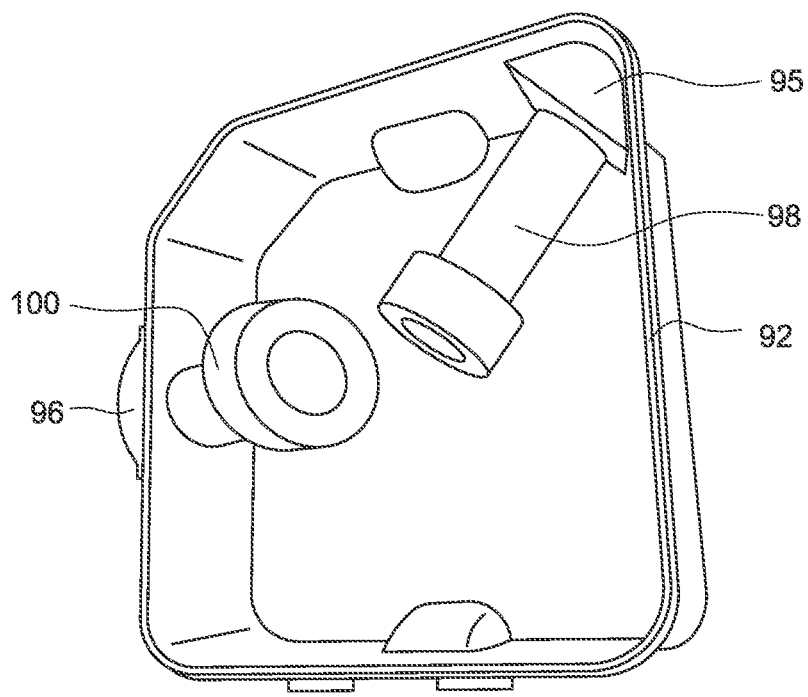
FIG. 21 is a perspective view of the tub lid and floating tubes of FIG. 19.
Figure 22:
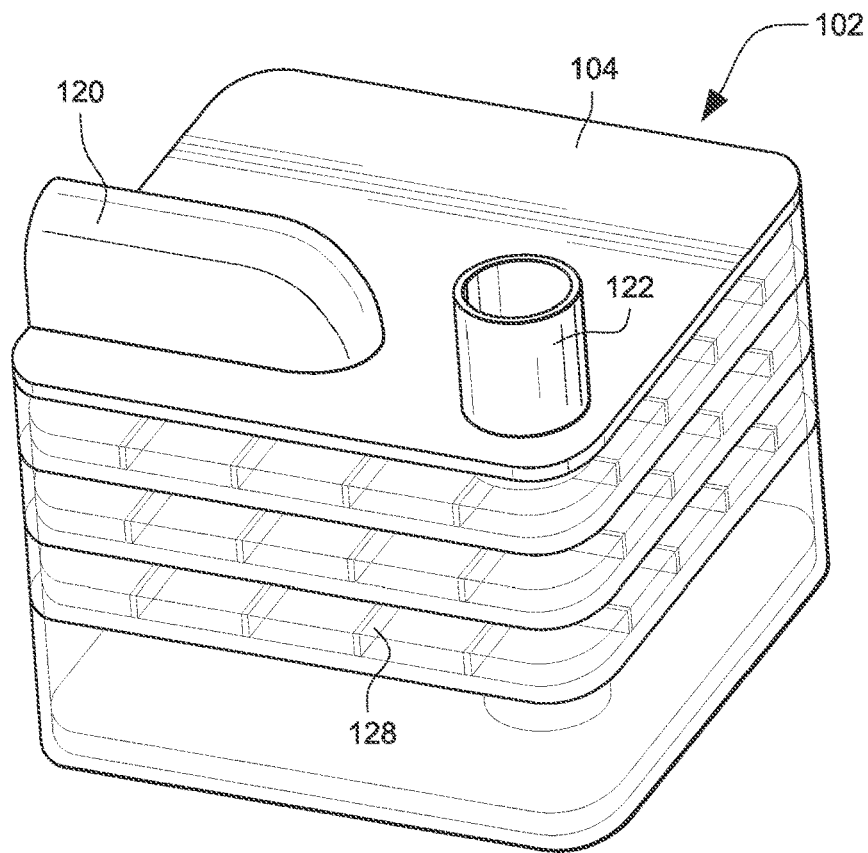
FIG. 22 is a perspective view of a multi-layer passover humidifier according to another example of the technology.
Figure 23:
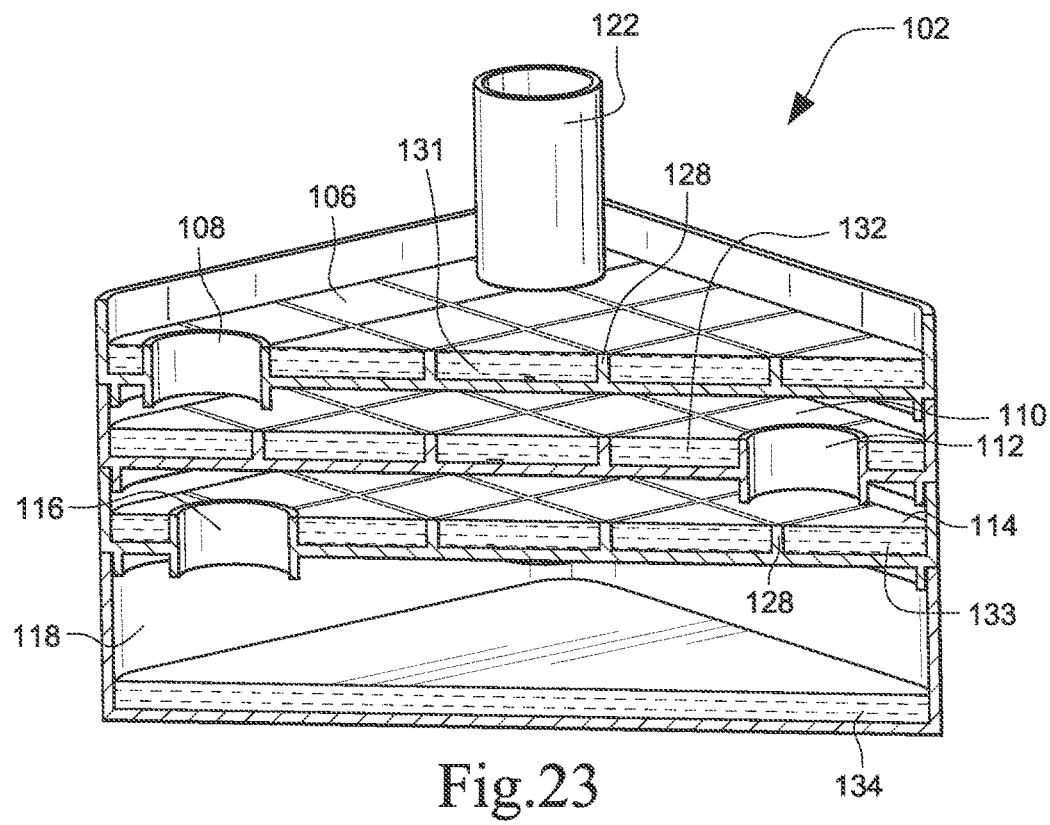
FIG. 23 is a cross section view of the humidifier of FIG. 22.

Referring to FIGS. 19-21, a humidifier comprises a humidifier tub 90 including a tub base 94 and a tub lid 92. The humidifier tub base and tub lid may be similar to the tub base and tub lid disclosed and described in, for example, U.S. 2011/0155132 A1 and U.S. Application 61/522,763, filed Aug. 12, 2011, the entire contents of both being incorporated herein by reference. In the tub 90, the inlet 95 and the outlet 96 of the tub lid 92 are connected to inlet and outlet tubes 98, 100, respectively, which extend inside the tub 90. The inlet tube 98 and the outlet tube 100 are flexible and/or pivotable, and at least a portion of the inlet tube 98 and the outlet tube 100 are configured to float on a surface of the supply of water contained in the tub 90 and prevent a flow of water back through the inlet 95 and/or the outlet 96 if the tub 90 is tilted and/or rotated. The inlet tube 98 and the outlet tube 100 may have at their opening end, floatable material 97, 99 (e.g. styrofoam), respectively. Alternatively, the entire inlet tube 98 and/or outlet tube 100 may be formed of a floatable material or may be coupled to floatable material to allow the inlet tube 98 and/or the outlet tube 100 to float. When the tub 90 is filled with water, the open ends of the inlet tube 98 and the outlet tube 100 will always stay afloat on the water surface no matter how the tub 90 is tilted. Accordingly, water is not able to flow back through the inlet 95 or the outlet 96 and spill into the flow generator or the air delivery conduit (i.e. the patient tube). In an alternative arrangement only the inlet tube 98 may be configured to float on a surface of the supply of water contained in the tub 90 to prevent a flow of water back through the inlet 95 and into the flow generator.

Multi-Layer Passover Humidifier

Figure 27:
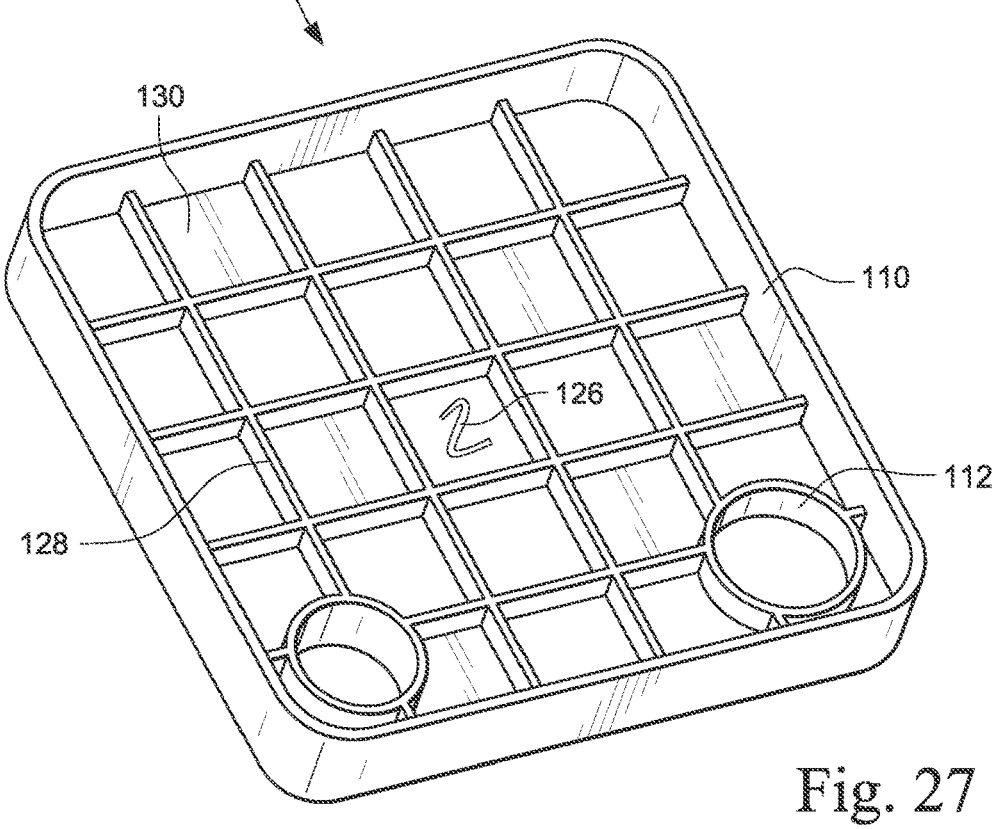
FIG. 27 is a perspective view of the second intermediate level of the humidifier of FIG. 22.
Figure 29:
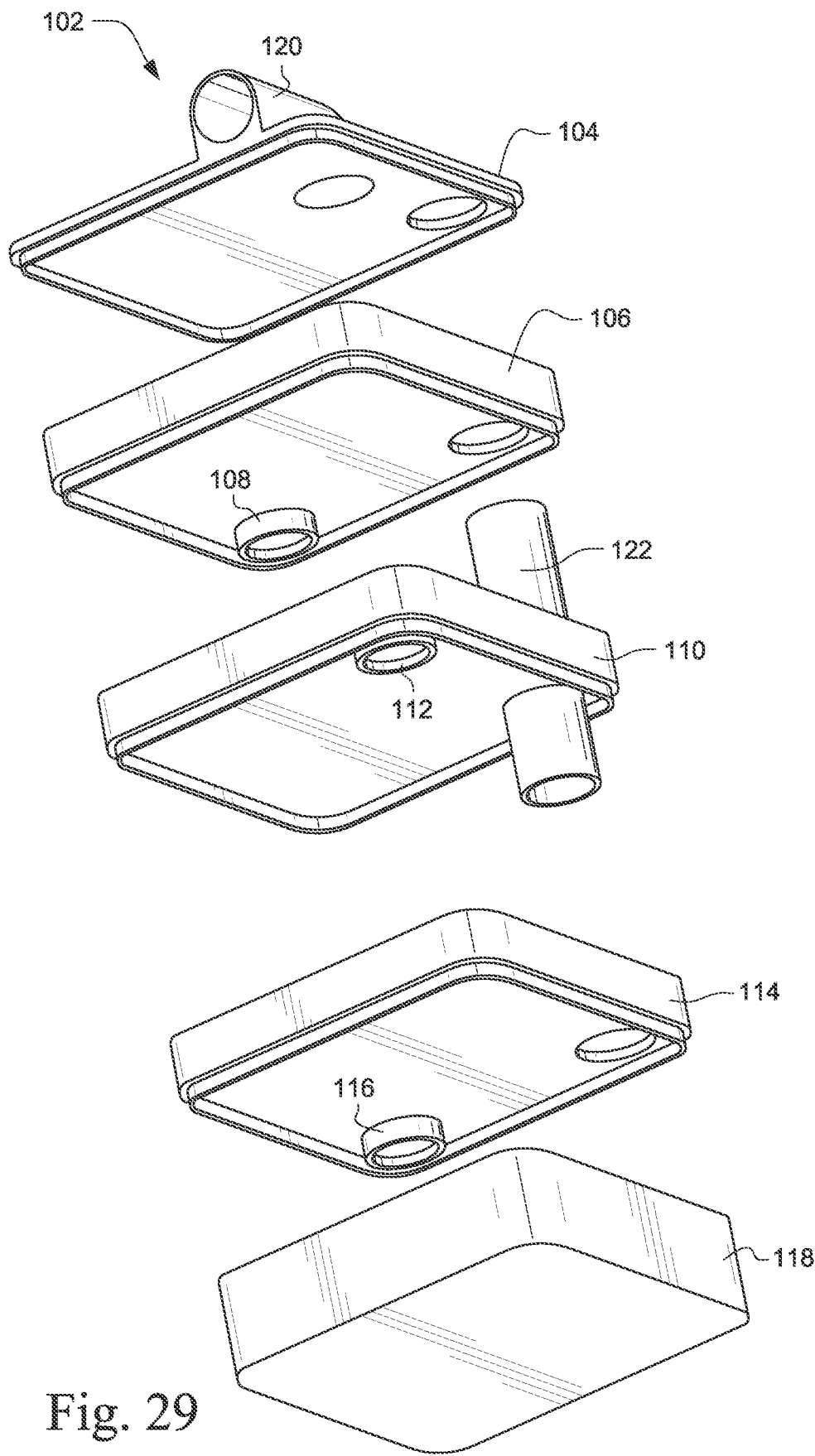
FIG. 29 is another exploded assembly view of the humidifier of FIG. 22.
Figure 30:
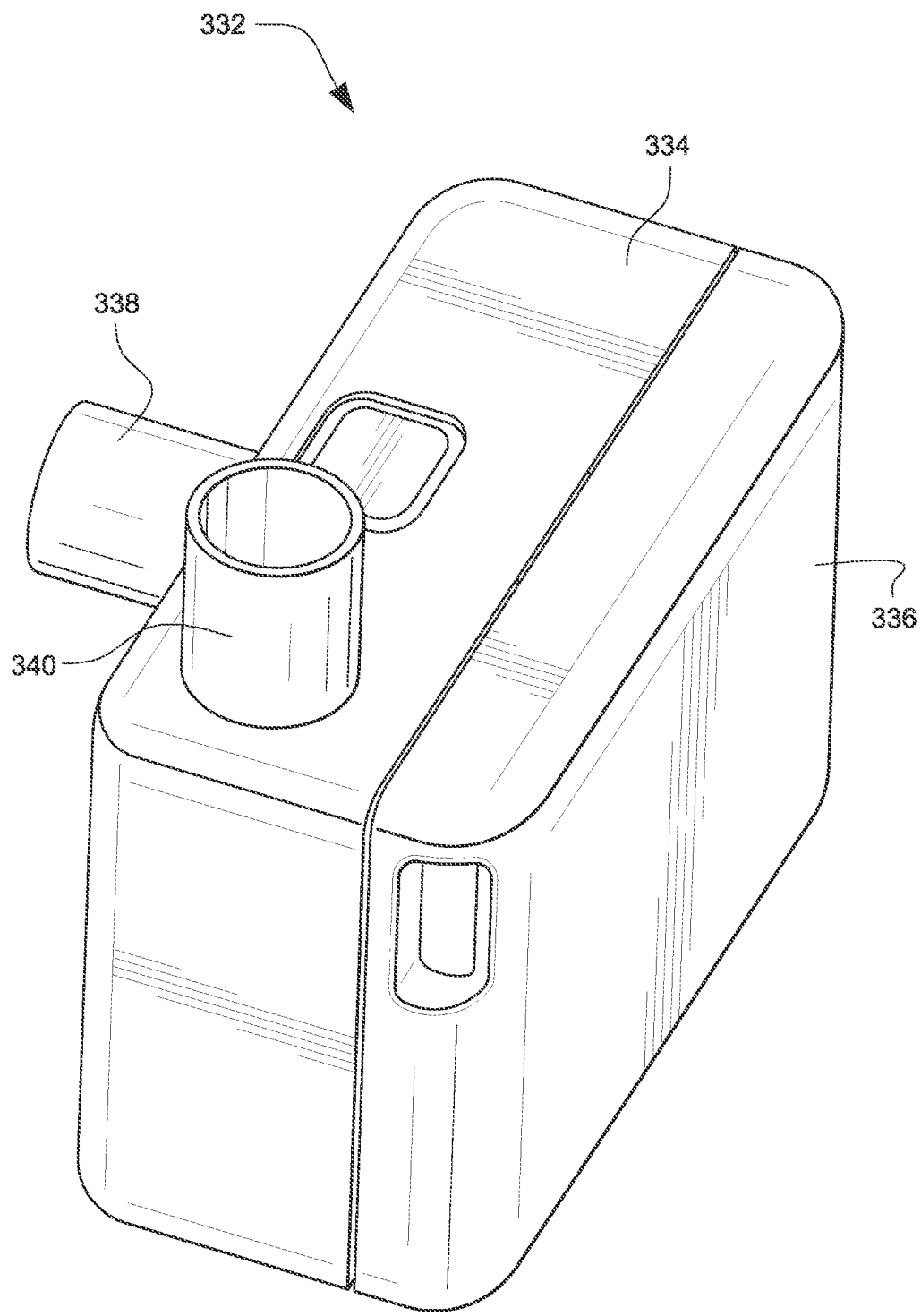
FIG. 30 is a view of a variable size humidifier according to another example of the technology.
Figure 31:
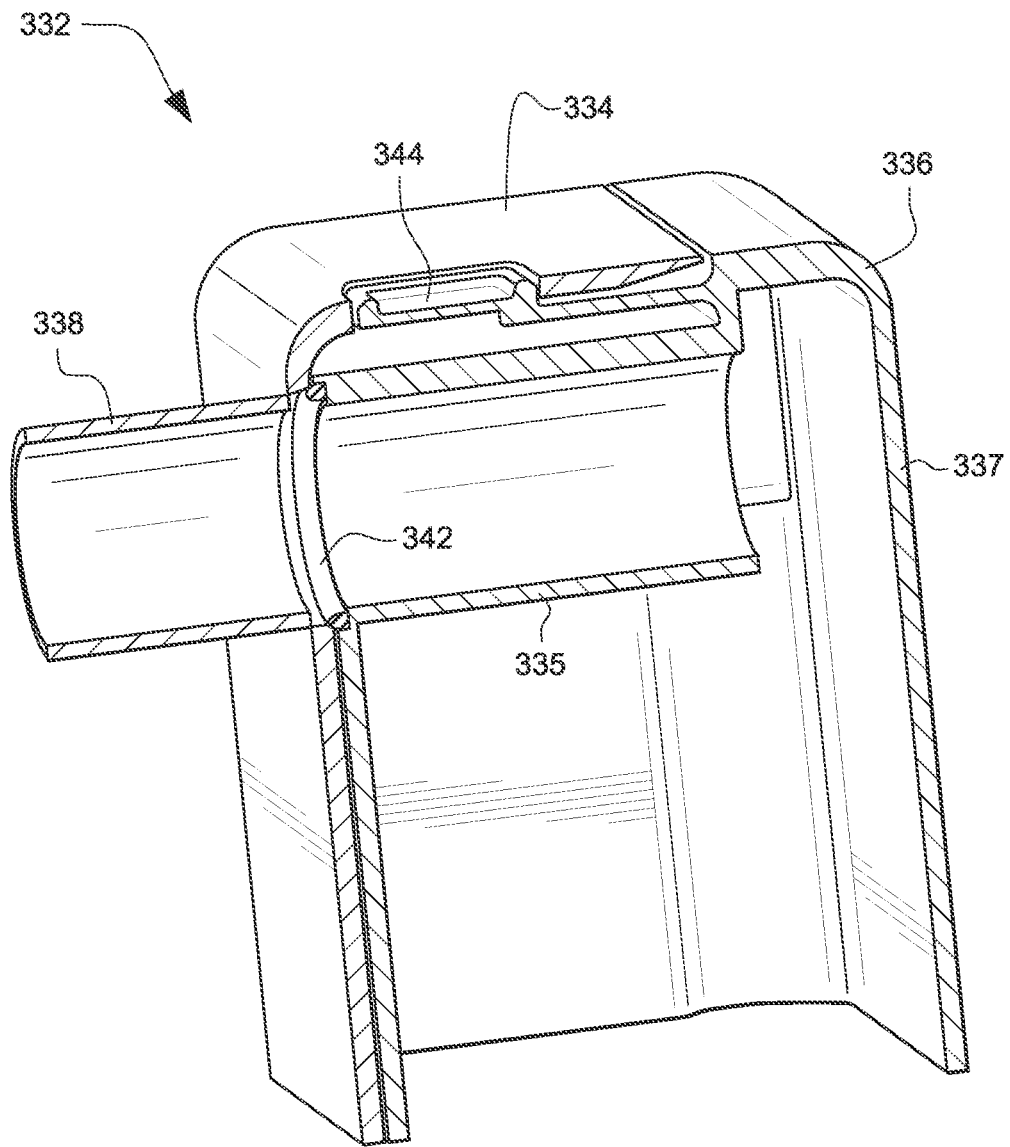
FIG. 31 is a cross section view of the humidifier tub of FIG. 30.
Figure 32:
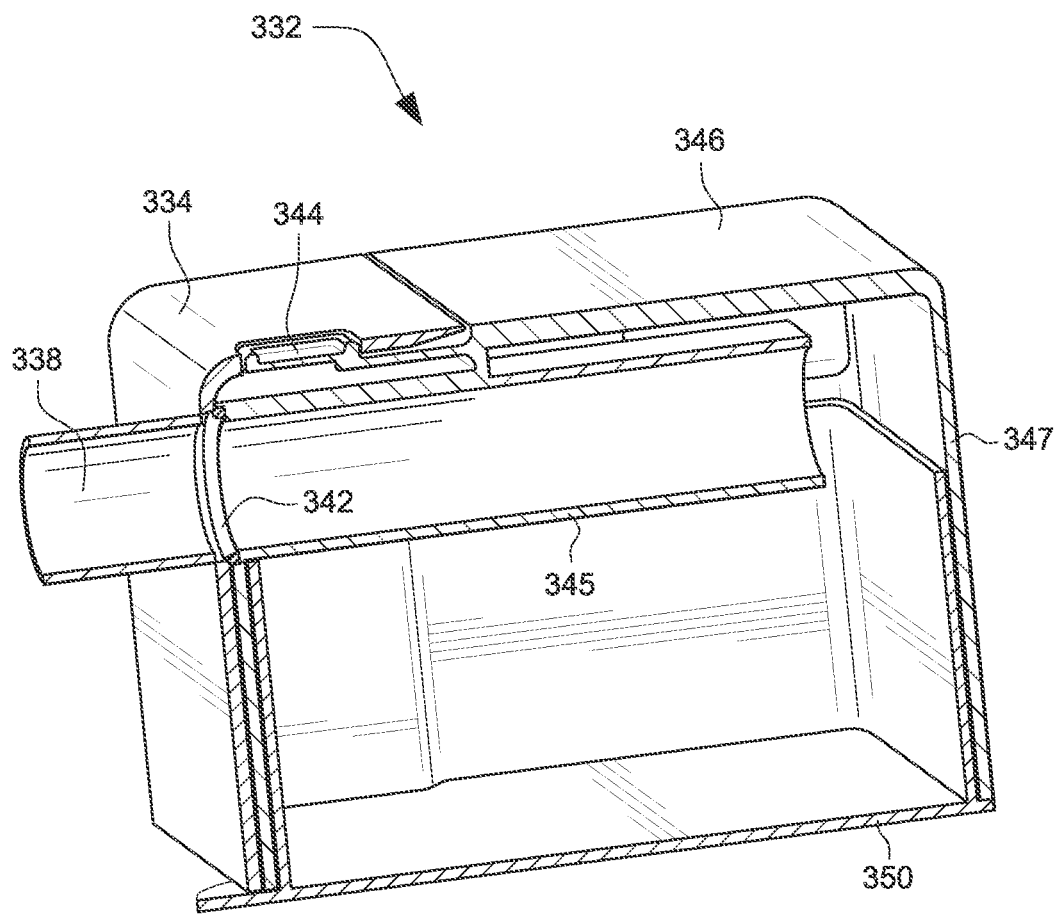
FIG. 32 is a cross section view of another humidifier tub with the humidifier of FIG. 30.
Figure 33:
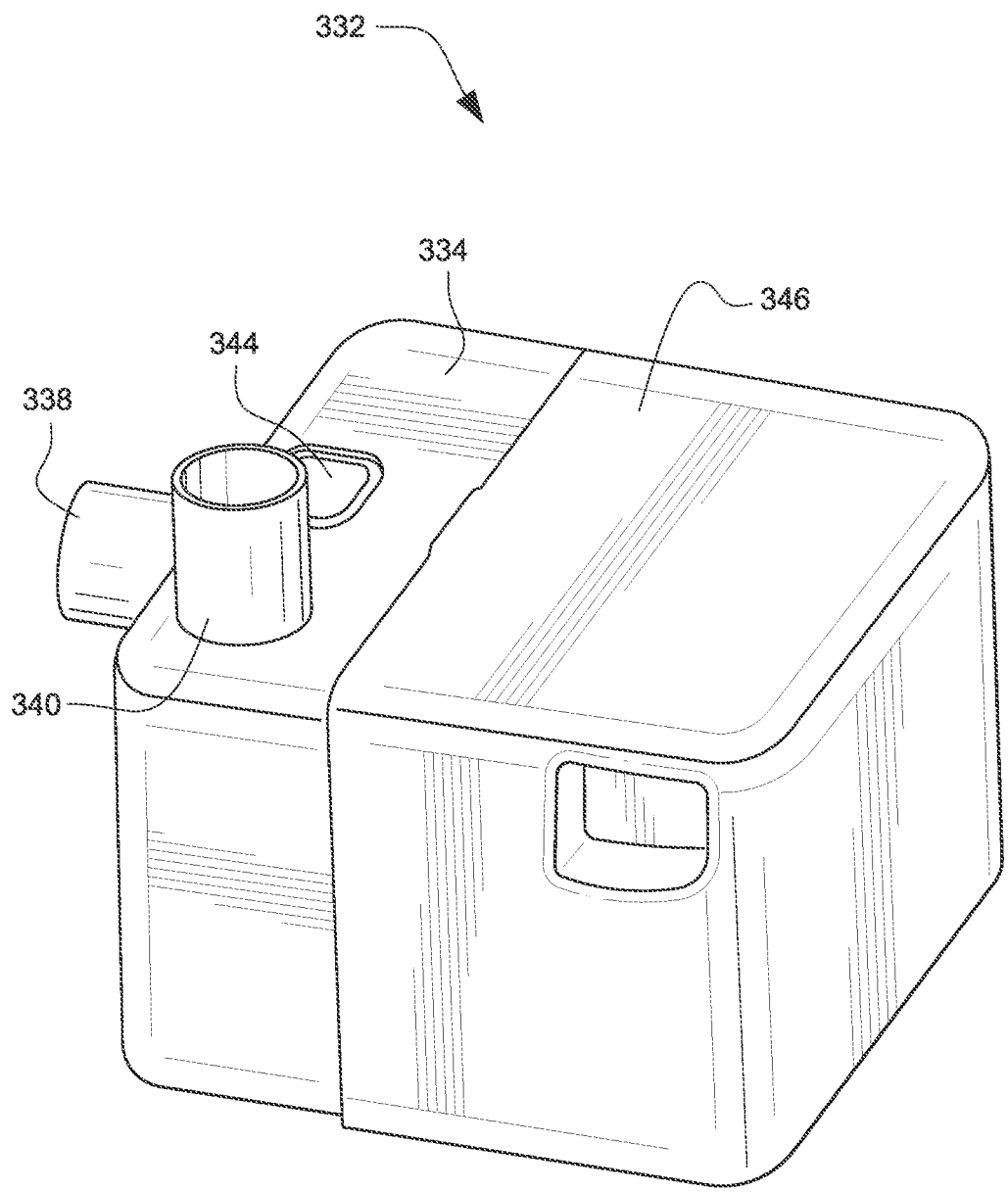
FIG. 33 is a perspective view of the humidifier tub of FIG. 32 with the humidifier of FIG. 30.
Figure 34:
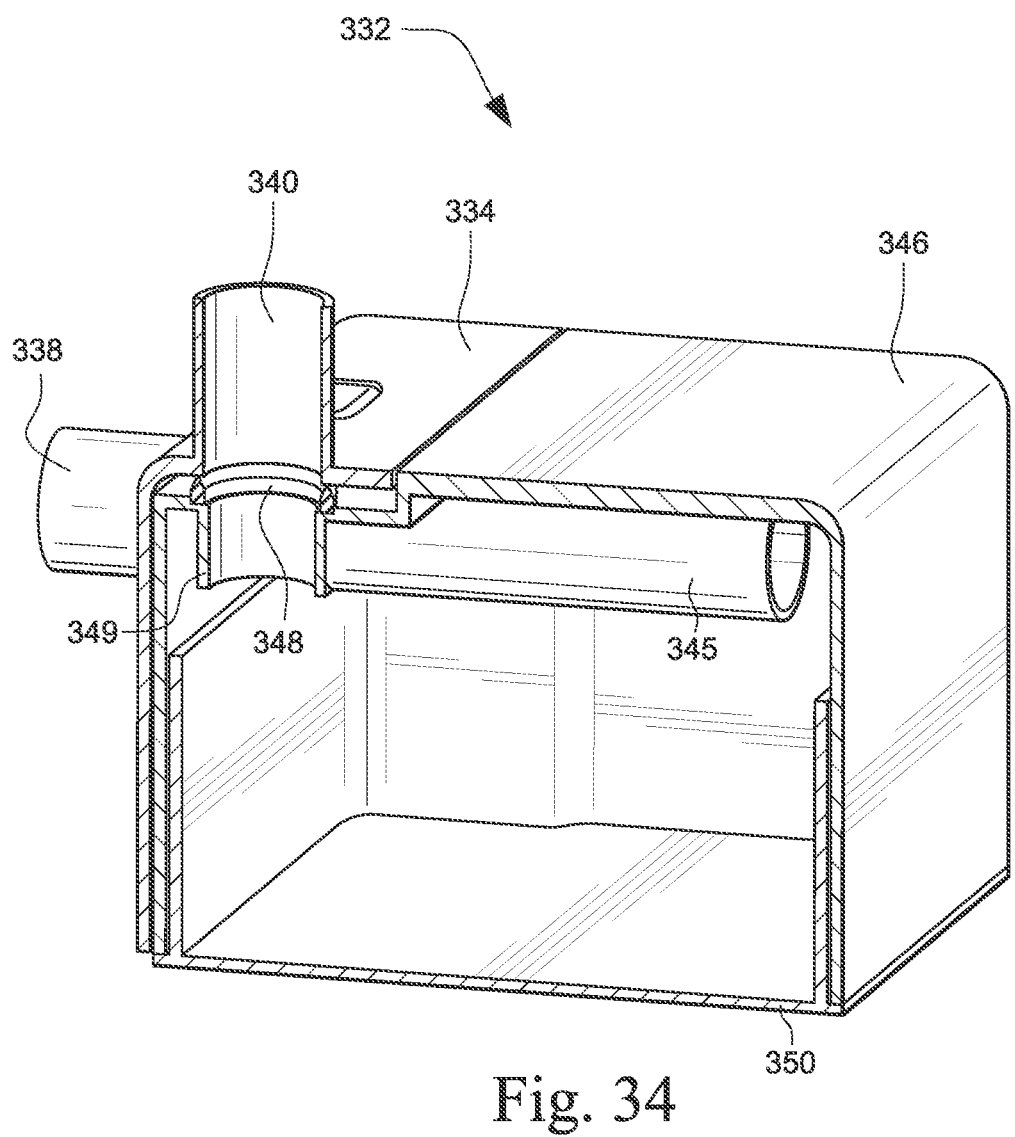
FIG. 34 is another cross section view of the humidifier tub of FIG. 32 with the humidifier of FIG. 30.
Figure 35:
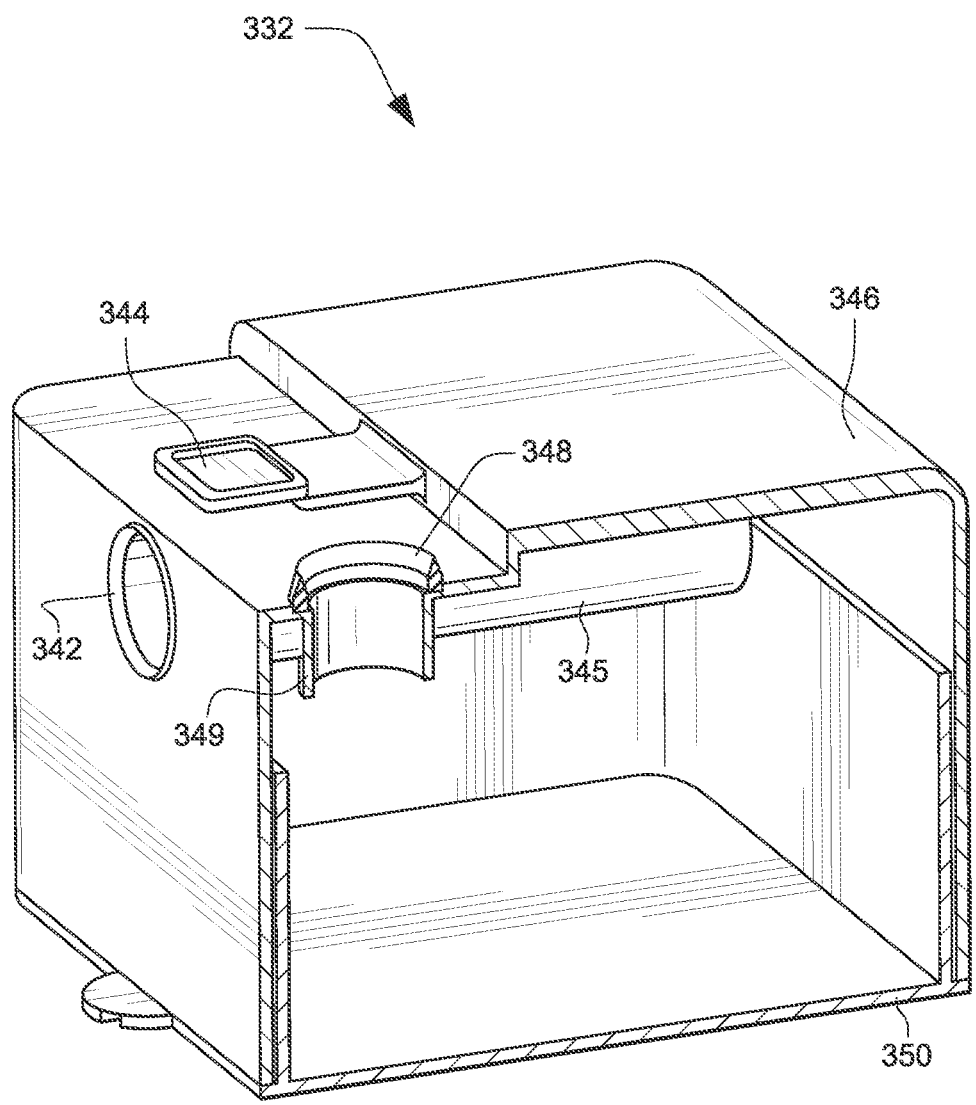
FIG. 35 is yet another cross section view of the humidifier tub of FIG. 32 with the humidifier of FIG. 30.
Figure 36:
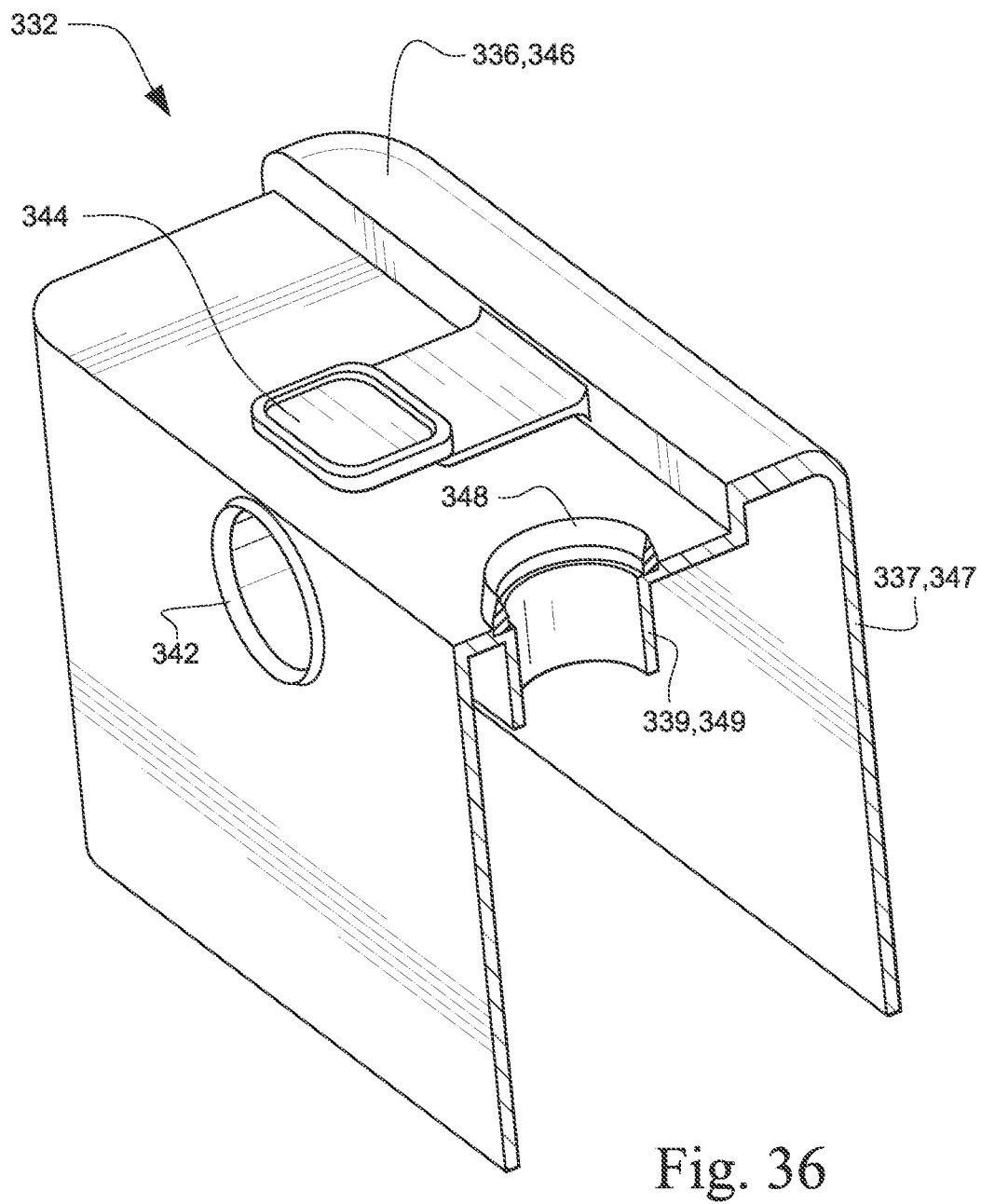
FIG. 36 is another cross section view of the humidifier of FIG. 30.
Figure 37:
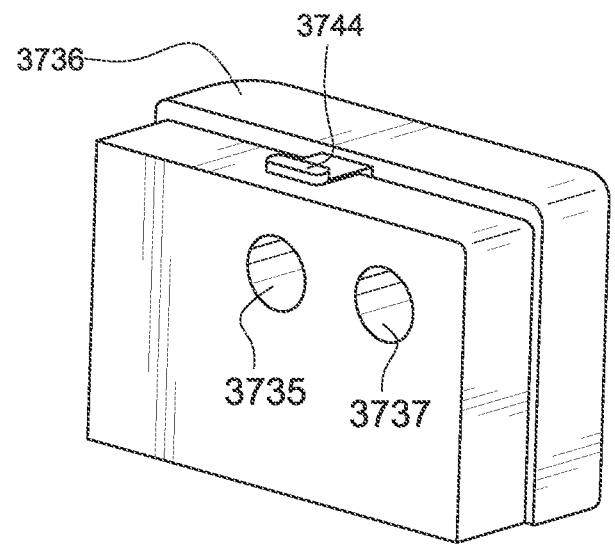
FIG. 37 is a view of a variable size humidifier according to another example of the technology.
Figure 38:
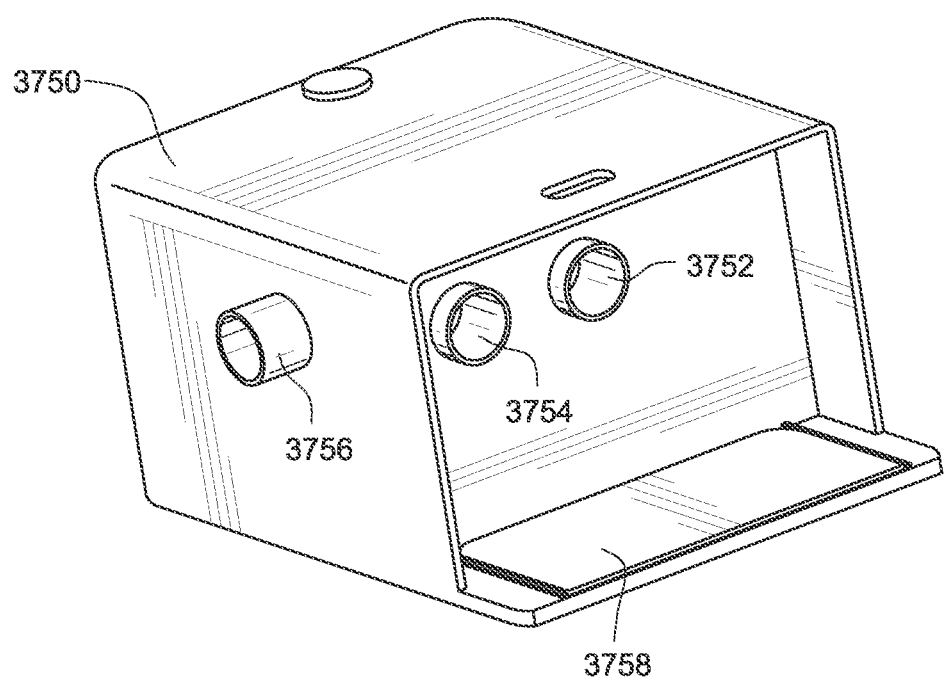
FIG. 38 is a view of a flow generator used with the humidifier of FIG. 37.

Referring to FIGS. 22-29, a humidifier 102 comprises a lid 104, at least one intermediate level, such as a top or first level 106, a second level 110, a third level 114, etc., and a bottom level or bottom chamber 118. Multiple intermediate levels may be provided between the lid 104 and the bottom chamber 118, such as 1, 2, 3, 4, 5 or more intermediate levels. The multiple intermediate levels 106, 110, 114 and the bottom chamber 118 increase the surface area to increase the humidity output of the humidifier 102. The humidifier 102 may be powered (i.e. heated) or non-powered. For example the humidifier may be provided with a lower powered heater (e.g. 10W) operated by, for example a battery. By increasing the surface area of the water contained by the humidifier 102, the humidifier 102 may be smaller than current humidifiers and thus be more suited for travel. The lid 104, the intermediate levels 106, 110, 114 and the bottom chamber 118 may be formed, for example, by moulding plastic material which would provide a relatively low cost humidifier. The lid 104, the intermediate levels 106, 110, 114, and the bottom chamber 118 may be sealed to each other with, for example, overmoulded seals provided around the perimeters of the lid 104, levels and bottom chamber 118. The bottom chamber 118 includes a heat conductive material, such as a heat conductive base, to allow the water within the tub 90 to be heated by coupling of a heat conductive base to a heating plate. As shown in FIG. 27, the intermediate levels 106, 110, 114 may be designated by indicia 126 and/or may include complementary engagement features that aid in assembly or prevent re-assembly of the lid 104, and the intermediate levels 106, 110 and 114 in an incorrect configuration.

The lid 104 includes an air flow inlet or inlet tube 120 and a humidified air flow outlet or outlet tube 122. As shown by the arrows in FIG. 24, the flow of breathable gas enters the humidifier 102 through the inlet 120 and flows across a surface of water 131 in the first level 106, through a first filler conduit 108, across a surface of water 132 in the second level 110, through a second filler conduit 112, across a surface of water 133 in the third level 114, through a third filler conduit 116, and across the surface of the water 134 in the bottom chamber 118. Thus, the conduit of each intermediate level is configured to direct the flow of breathable gas across the surface of the water of the next level. The humidified flow of breathable gas exits the humidifier through the outlet 122.

In order to fill the humidifier 102 with water, the lid 104 is removed and water is poured into the first level 106. Each intermediate level may comprise a grid pattern 128 forming a plurality of grids 130 in each level. The grid pattern 128 and the grids 130 make the humidifier 102 fairly tolerant of tipping when filling the humidifier 102 as the water is locally contained to a degree within each grid 130. Additional containment walls may be provided to contain the water from flowing down the filler conduits 108, 112, 116 when the humidifier 102 is tilted.

The water poured into the first level 106 continues to fill the grids 130 of the first level 106 until the water level reaches the level of the first filler conduit 108. As water is continued to be poured into the first level 106, the additional water flows through the first filler conduit 108 into the second level 110 until it fills the grids 130 of the second level 110 and reaches the level of the second filler conduit 112. As more water is added, the water flows through the second filler conduit 112 and flows into the third level 114. Once the grids 130 of the third level 114 are filled and the water level reaches the level of the third filler conduit 116, the water flows through the third filler conduit 116 into the bottom chamber 118. The bottom chamber 118 has a capacity large enough for all of the water in the event that the water from all the preceding intermediate levels, e.g. the first three levels, is spilled into the bottom level. A water level indicator may be provided at the bottom chamber 118 so the humidifier tub 102 would not be overfilled as to obstruct air flow passage exiting through the outlet 122.

Figure 24:
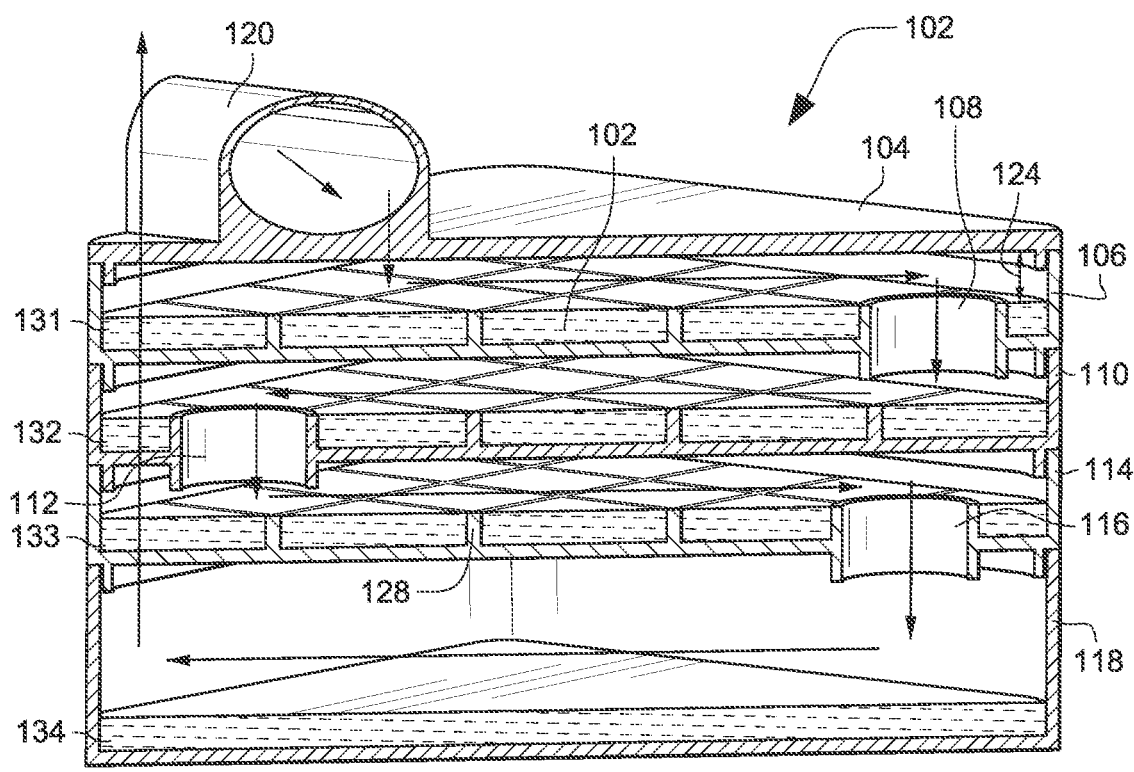
FIG. 24 is a another cross section view of the humidifier of FIG. 22.
Figure 25:
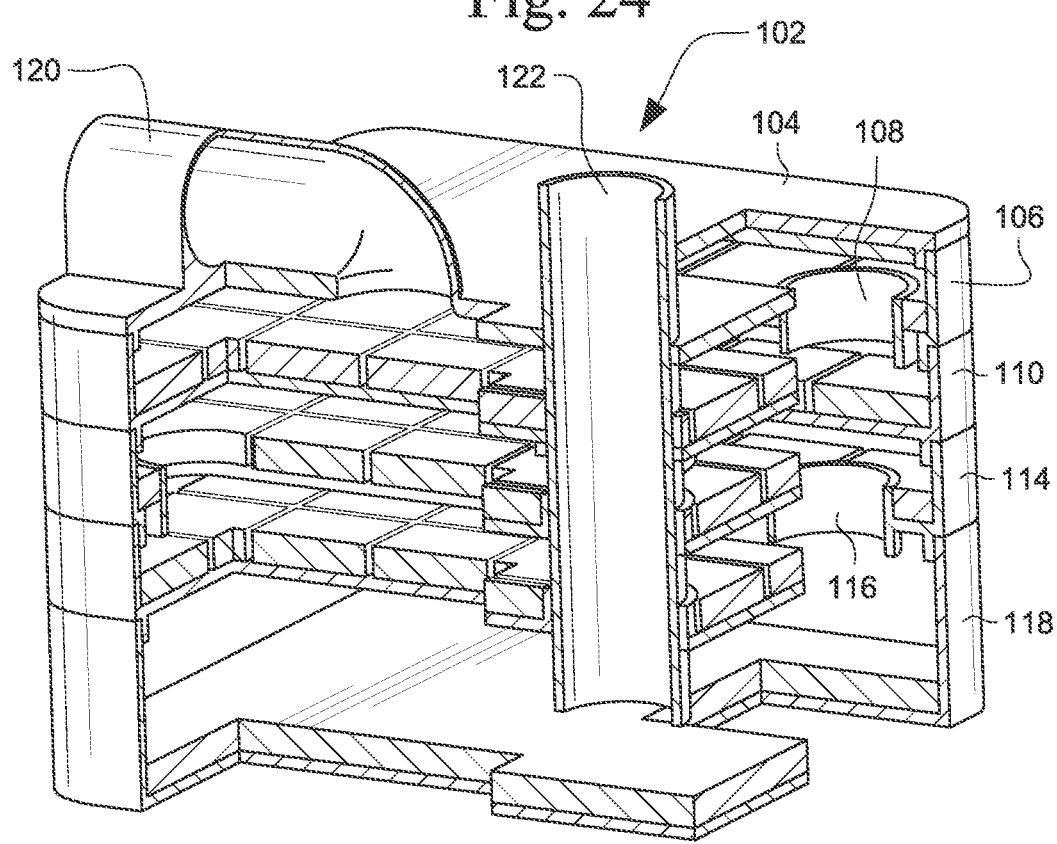
FIG. 25 is still another cross section view of the humidifier of FIG. 22.
Figure 26:
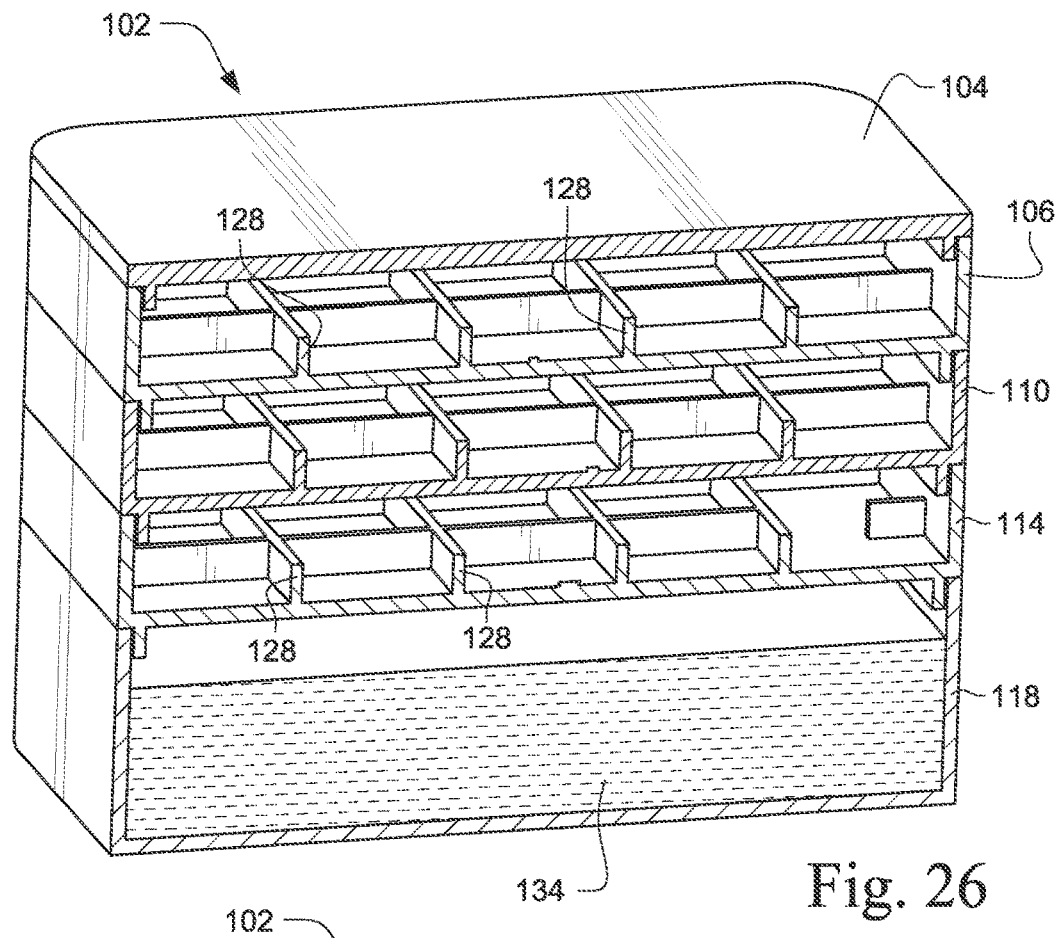
FIG. 26 is a yet another cross section view of the humidifier of FIG. 22.

The pressure drop of the flow of breathable gas through the humidifier 102 may be modified by adjusting the diameters of the filler conduits 108, 112, 116. For example, the pressure drop may be reduced by increasing the diameter of some or all of the filler conduits. It should also be appreciated that the pressure drop may be varied by changing the number of intermediate levels of the humidifier. As shown in FIG. 24, an air gap height 124 may be chosen so as not to have spitting due to a high speed air flow.

Humidifier with Variable Size Tubs

Referring to FIGS. 30-36, a humidifier 332 comprises a first tub 336 and a dock 334 configured to receive the first tub 336. The dock 334 may be part of a flow generator of, for example, a CPAP apparatus or a separate component that is coupled to a flow generator either directly or via a conduit. An air flow dock inlet 338 is connected to the dock 334, and an inlet seal 342 may be provided to seal the connection between the dock inlet 338 and the dock 334. It should be appreciated that the dock inlet 338 and the dock 334 may be integrally formed. The first tub 336 comprises a first tub inlet tube 335 in the form of, for example, a tube conduit that is in communication with the dock inlet 338 and sealed to the dock 334 and the air flow dock inlet 338 by the inlet seal 342. The dock 334 also includes a dock outlet 340 connected to the dock 334 and an outlet seal 348 that seals the connection. It should also be appreciated that the dock outlet 340 may be integrally formed with the dock 334.

The first tub 336 includes an end inner wall 337 that is opposed to the end of first tub inlet tube 335. The first tub inlet tube 335 directs the inlet airflow to the end inner wall 337 of the first tub 336 thus directing the air to flow across the whole water surface before flowing out a first tub outlet tube 339 that is in communication with the dock outlet 340 of the dock 334. The first tub inlet tube 335 has a length that provides tilt protection to prevent or reduce the amount of water flowing out of the dock inlet 338, for example into the flow generator, if the humidifier 332 is tilted. The first tub 336 may also comprise a latch 344 that provides a snap connection to the dock 334.

A second tub 346 sized differently from the first tub 336 may be connected to the dock 334. The second tub 346 may be larger than the first tub 336 to enable the second tub 346 to hold more water than the first tub 336. The second tub 346 includes a second tub inlet 345 similar to the first tub inlet 335 of the first tub 336, but having a greater length. The second tub inlet 345 also directs the inlet air flow against the end inner wall 347 of the second tub 346 to direct the air flow across the whole water surface before flowing out the second tub outlet 349 that is in communication with the dock outlet 340 of the dock 334. The second tub inlet 345 of the second tub 346 also provides tilt protection in the same manner as the first tub inlet 335 of the first tub 336. The second tub 346 may also comprise the latch 344 for connecting the second tub 346 to the dock 334.

The inlet and outlet seals 342, 348 may be overmoulded to the dock 334 and/or the tubs 336, 346. In the case where the dock 334 is part of a flow generator, the tub 336, 346 may replace an outlet muffler connected to the flow generator. The first and second tubs 336, 346 may be configured to be clipped or snapped into the same position as the outlet muffler. Thus at least one of the first tub 336 and the second tub 346 may have a same configuration as the outlet muffler of the flow generator. The first tub 336 and the second tub 346 may also include a heater element 350 in the base of the tub to heat the water contained in the tub.

With the humidifier 332 with variable tub size, the patient or clinician can choose to dock a large or smaller sized water reservoir or tub, depending on portability, water usage, and desired size requirements. The components of the humidifier are also easy to mould and/or assemble. The locations of the inlet tubes 335, 345 and the outlets of the tubs 336, 346 provide good airflow direction across the surface of the water and spillback tilt protection. There may be a range of differently sized tubs available to meet differing humidification and/or portability requirements.

Referring to FIGS. 37-40, a variant of the humidifier includes a tub 3736 having a tube inlet 3735, a tub outlet 3737, and a flange. As shown in FIGS. 37-40, the tub inlet and outlets 3735, 3737 of the tub 3736 are horizontal which provides easier connection of the tub 3736 to the flow generator 3750, and the same face sealing direction is applied for both the inlet and outlet. The tub 3736 may have a latch 344, such as a snap latch, configured to releasably connect the tub 3736 to a cradle or dock which may be, for example, a flow generator 3750. The tub 3736 may be one of a plurality of tubs of varying size.

The flow generator 3750 may comprise a housing, a divider, and a flow generator outlet 3752 for a flow of breathable gas generated by the flow generator 3750 configured to be in communication with the tub inlet 3735 of the tub 3736 and a humidified flow inlet 3754 configured to be in communication with the tub outlet 3737 of the tub 3736. A tubing connector 3756 is configured to be connected to a delivery tube, hose or conduit configured to be connected to a patient interface for delivery of the humidified flow of breathable gas. The flow generator 3750 may also include a heater element 3758 configured to heat the supply of water or liquid in the tub 3736.

Figure 39:
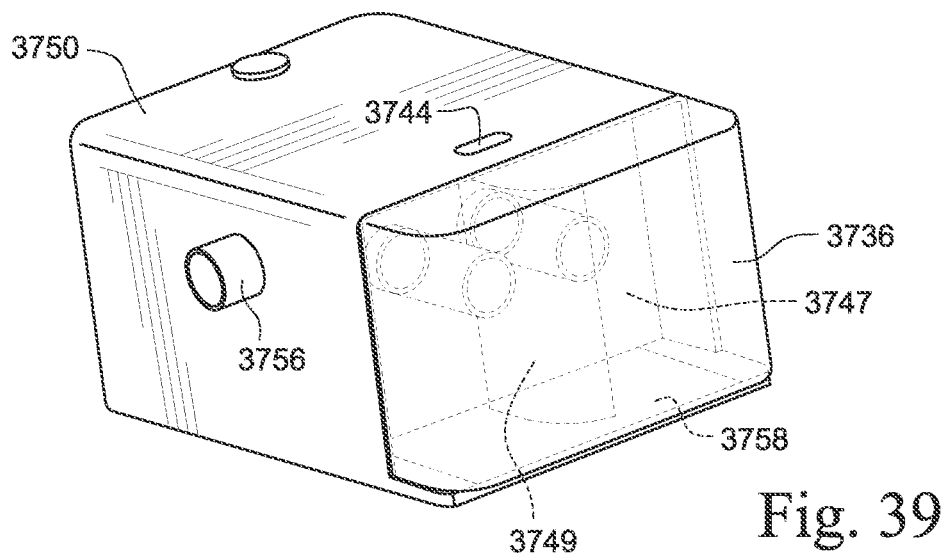
FIG. 39 is an assembly view of the humidifier and flow generator of FIGS. 37 and 38.
Figure 40:
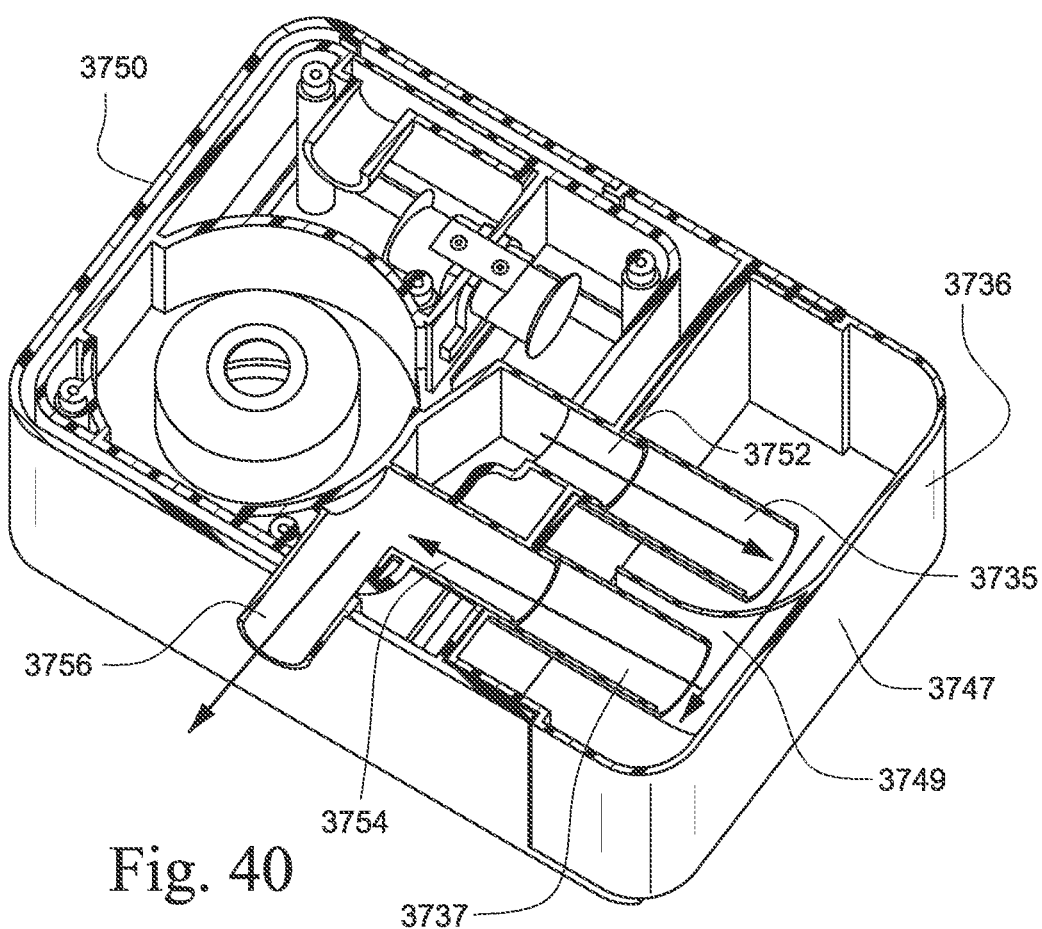
FIG. 40 is a cross section view of the humidifier and flow generator of FIG. 39.

As shown in FIGS. 39 and 40, the tub 3736 has an end inner wall 3747 to direct the air flow across the whole water surface before flowing out the outlet 3737. A curved wall or baffle 3749 may also be provided to direct the flow across the water surface.

Figure 40A:
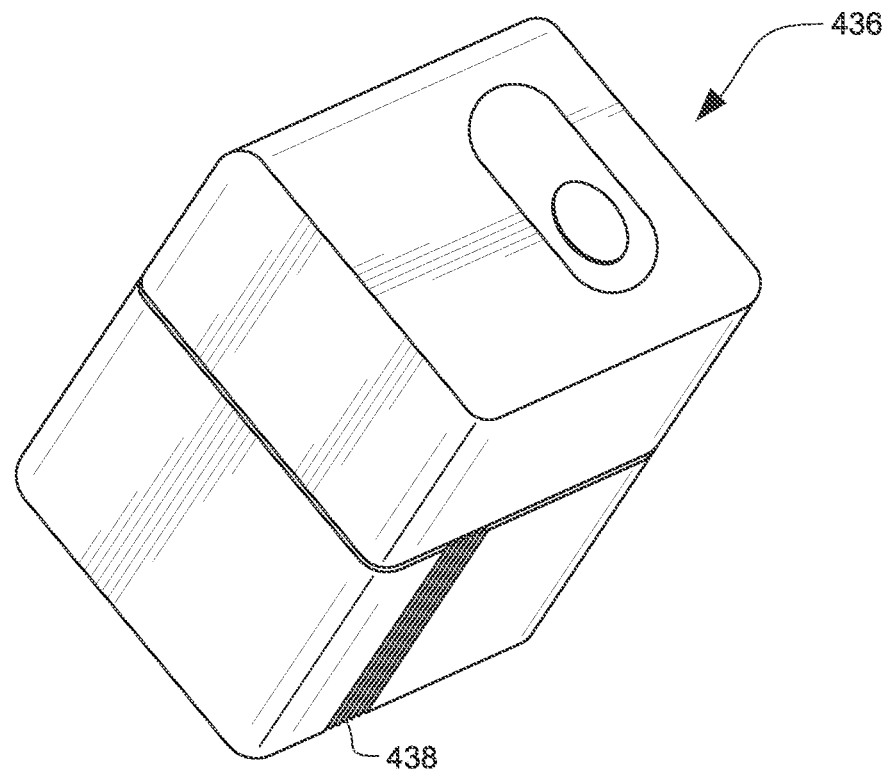
FIG. 40A is a perspective view of a variable size humidifier tub for the variable size humidifier of FIG. 37.
Figure 40B:
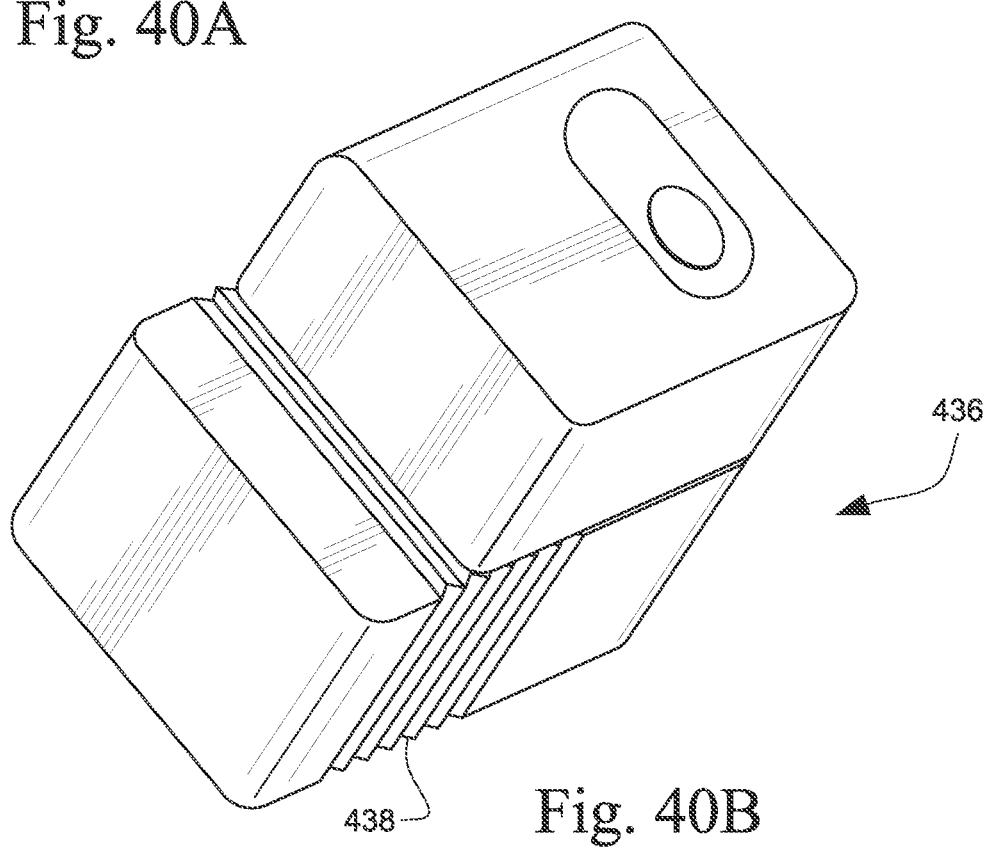
FIG. 40B is another perspective view of the humidifier tub of FIG. 40A.
Figure 40C:
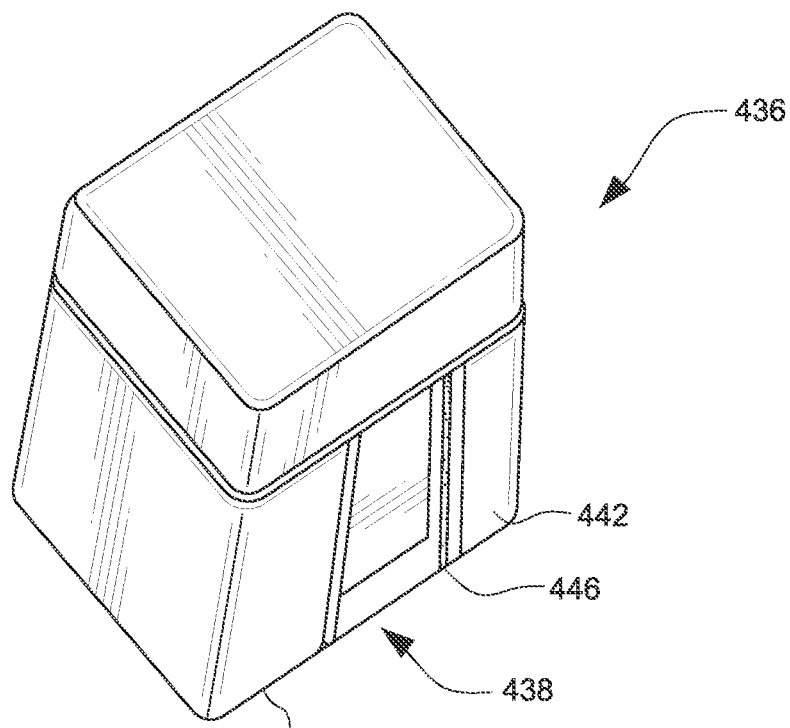
FIG. 40C is a perspective view of another variable size humidifier tub for the variable size humidifier of FIG. 37.
Figure 40D:
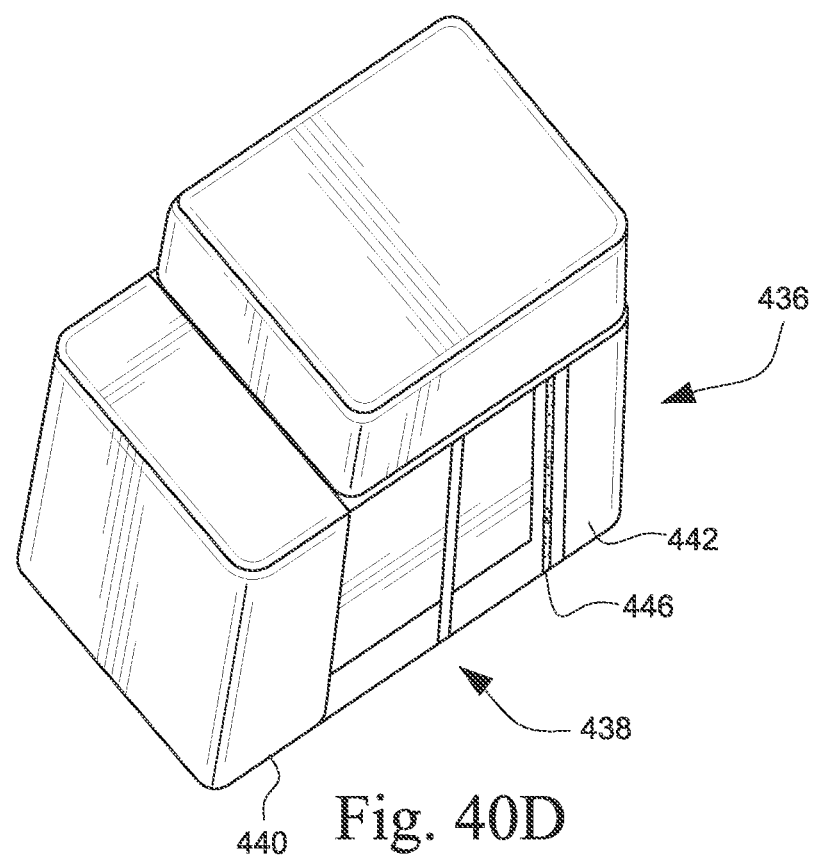
FIG. 40D is another perspective view of the humidifier tub of FIG. 40C.
Figure 40E:
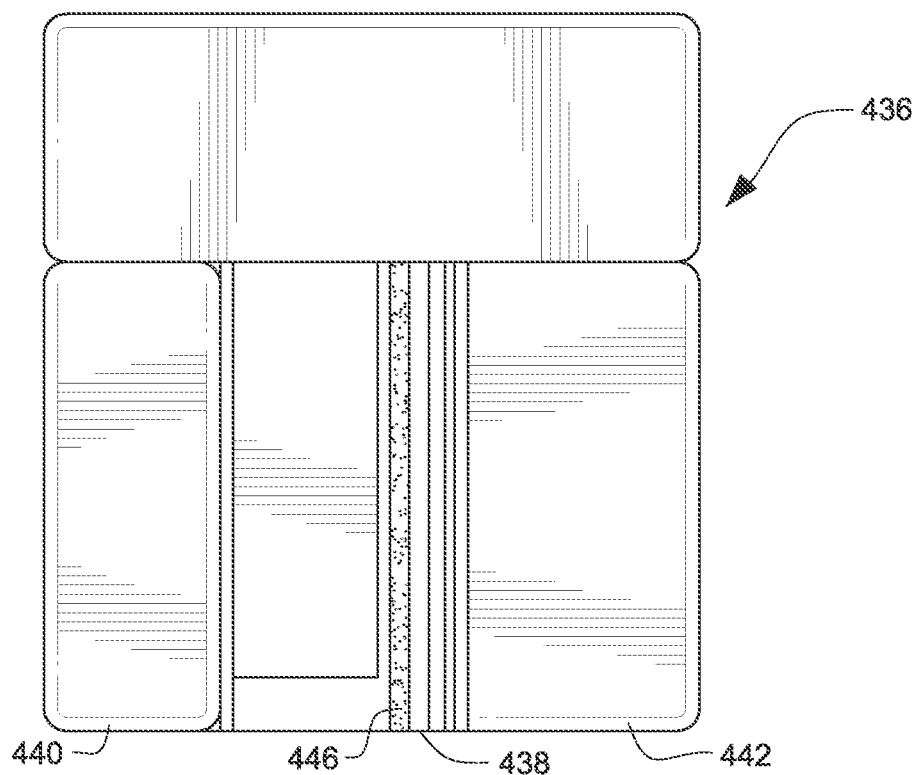
FIG. 40E is a side view of the humidifier tub of FIG. 40C.
Figure 40F:
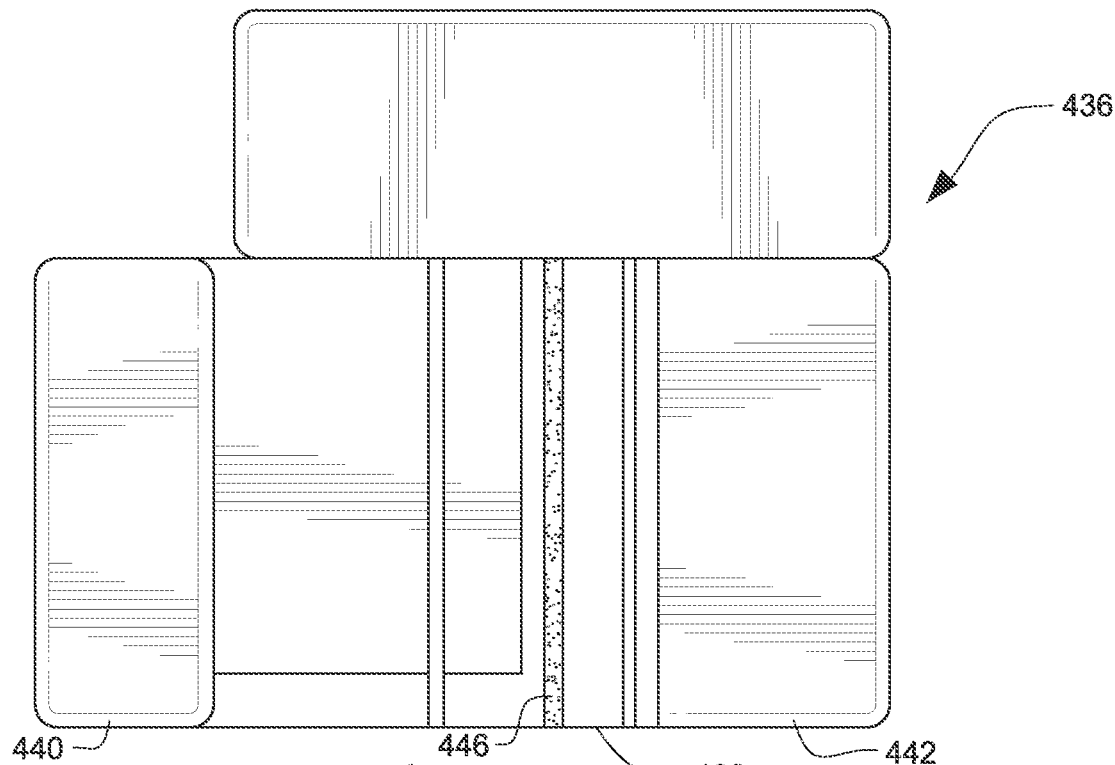
FIG. 40F is another side view of the humidifier tub of FIG. 40C.
Figure 40G:
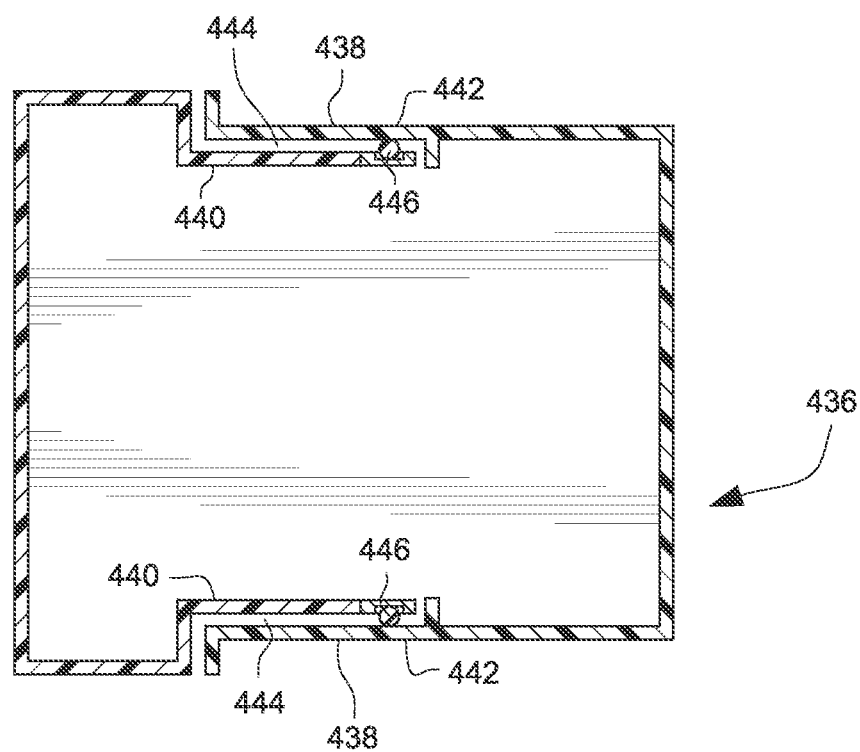
FIG. 40G is a top view of the humidifier tub of FIG. 40C.

In another arrangement (see FIGS. 40A-40G) a tub 436 may include an adjustable portion 438 that is configured to be expanded or contracted to adjust the size of the tub 436. The tub 436 may be fixed or locked in a range of different sizes to adjust to the humidification and/or portability needs of the user. For example the tub 436 may include a concertina-type section or collapsible and expandable folds (FIGS. 40A-40B). The concertina-type section and the other portions of the tub 436 may be made from the same or different materials. For example, the concertina-type section may be made from a rigid plastic material or a flexible material such as silicone. In addition, the walls in the concertina-type section may have a different thickness or the same thickness as the walls of the other portions of the tub 436. Thinner walls may increase the expandable capacity of the tub 436.

The adjustable portion 438 may be a sliding portion (FIGS. 40C-40G). When the adjustable portion 438 is a sliding portion, the tub 436 may include an expansion portion 440 and a base portion 442. The expansion portion 440 and the base portion 442 may overlap each other and may be separated by a gap 444. The gap 444 may serve to minimize wear to the opposing surfaces of the expansion portion 440 and the base portion 442 caused by movement between the expansion portion 440 and the base portion 442. A gap seal 446 may be positioned between the expansion portion 440 and the base portion 442 to prevent liquid from leaking through the gap 444. The gap seal 446 may be affixed to and may move with the expansion portion 440. In addition, the gap seal 446 may be, for example, an o-ring or an overmold seal. The expansion portion 440 and the base portion may be made from the same or different materials.

In certain arrangements the tub 436 may be fixed or locked into one of a plurality of sizes by clamping a protrusion or lug into one of a range of different recesses or apertures provided on the tub 436. In another arrangement an adjustable length latch may fix the tub 436 to form the different size tubs. The tub 436 may be formed of a plastic material or may include a combination of materials including a plastic material and a flexible material such as silicone. The flexible material may be configured to expand and contract.

The adjustable portion 438 may increase the capacity of the tub 436 by between about 10-100% (e.g., 20%, 30%, 40% 50%, 60%, 70%, 80%, 90%). In addition, the adjustable portion 438 may increase a volume of the tub 436 by predetermined discrete increments such as, for example, 5 mL, 10 mL, 20 mL, or more. Alternatively, the adjustable portion 438 may increase the volume of the tub 436 by an infinite number of increments. Furthermore, the adjustable portion 438 may be a combination of one or more of the arrangements disclosed above (e.g., a combination of a sliding section and a concertina-type section).

In certain arrangements a size of an inlet tube may also be configured to adjust by expanding and contracting in combination with the size of the tub to maintain the tilt protection feature and prevent spillback into the flow generator as described above in relation to FIGS. 30 to 36.

Humidifier with Mechanical Humidity Control

Figure 41:
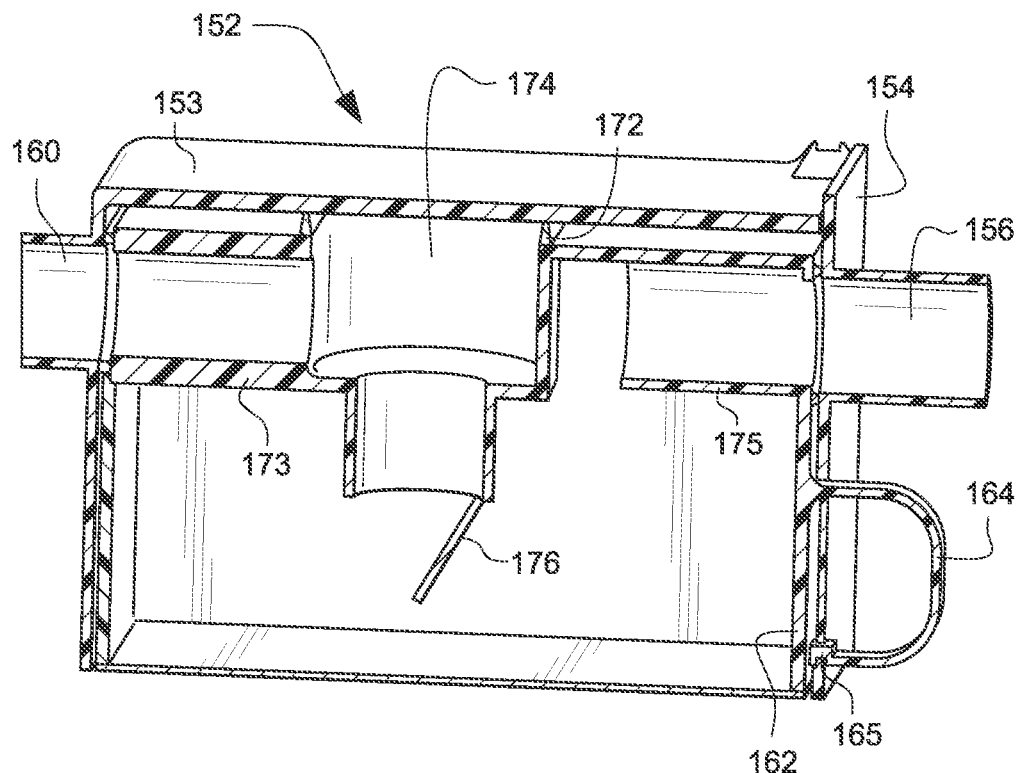
FIG. 41 is a cross section view of a humidifier including a tub and a cradle.
Figure 42:
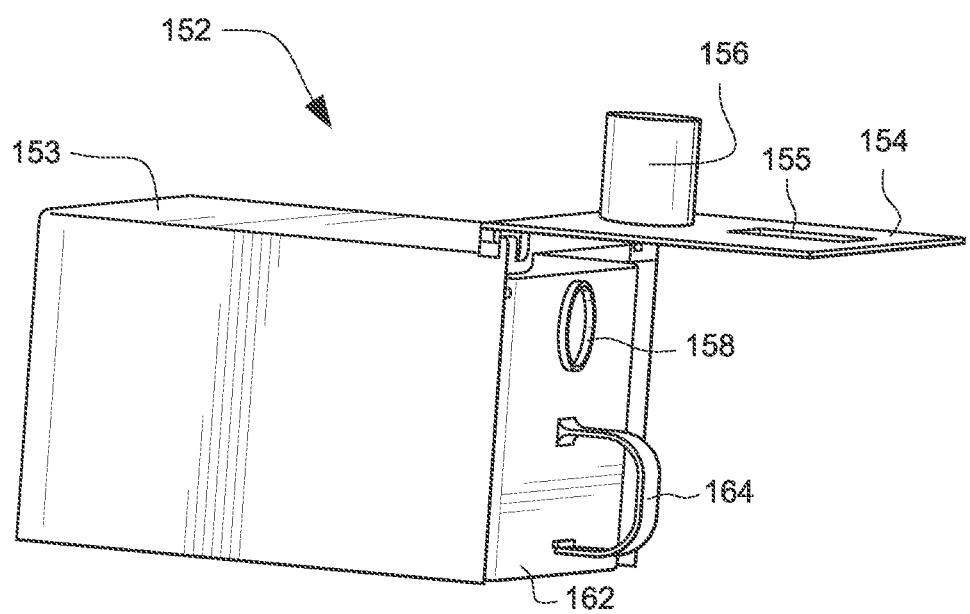
FIG. 42 is a perspective view of the humidifier of FIG. 41.
Figure 43:
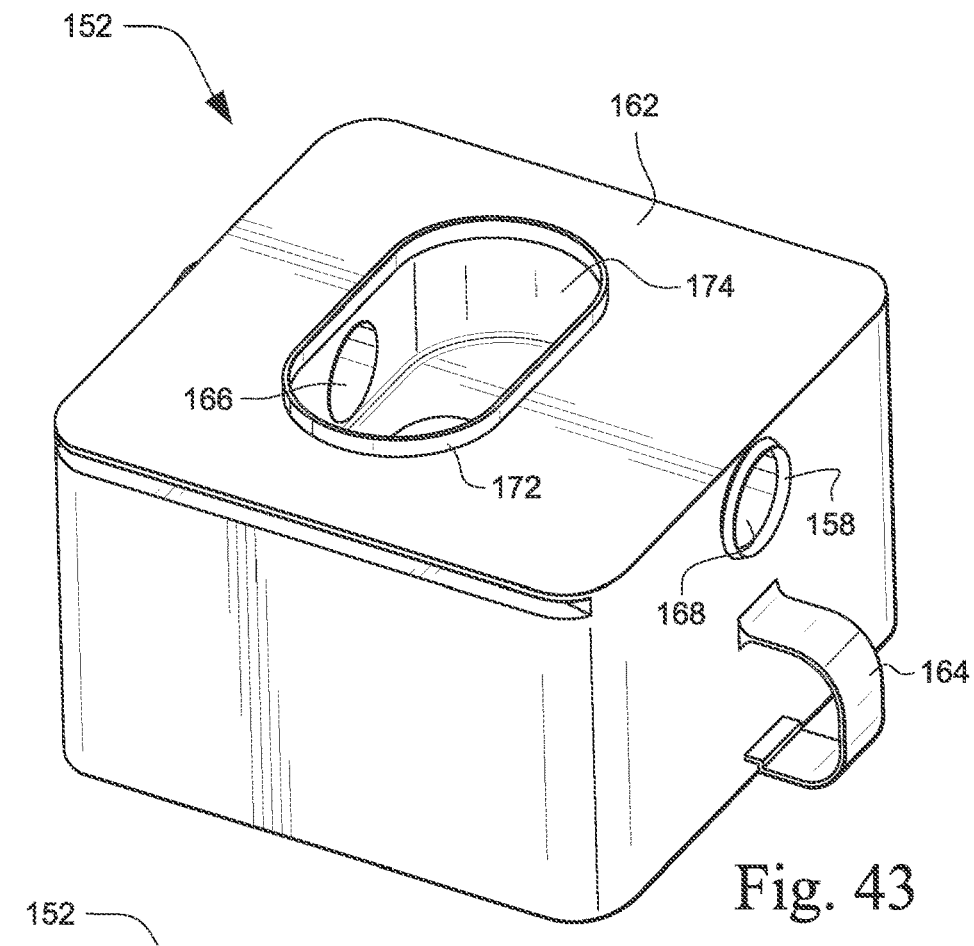
FIG. 43 is a front perspective view of the tub of the humidifier of FIG. 41.
Figure 44:
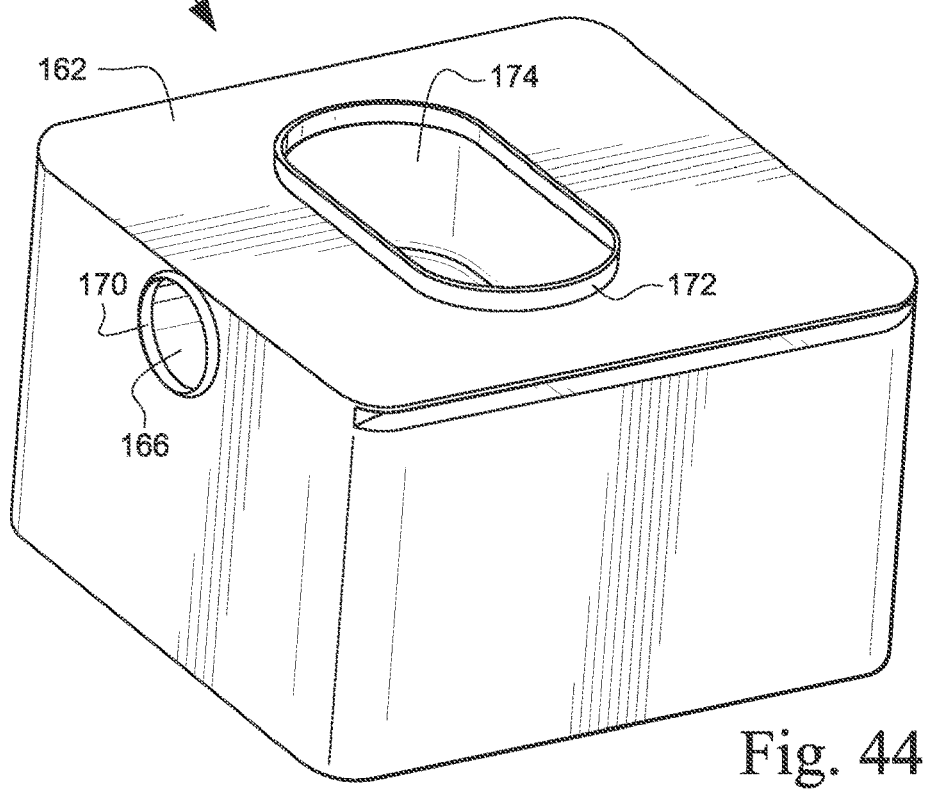
FIG. 44 is a rear perspective view of the tub of the humidifier of FIG. 41.

Referring to FIGS. 41-44, a humidifier 152 comprises a tub 162. The tub 162 may be similar to the tubs disclosed and described in WO 2010/031126 A1 and U.S. Application 61/522,763, filed Aug. 12, 2011, the entire contents of both being incorporated herein by reference. The tub 162 may be placed in a cradle or dock 153. The cradle or dock 153 may have a hinged lid 154 that is pivotable between a closed position (FIG. 41) and an open position (FIG. 42). The hinged or pivotable lid 154 may have an opening 155 and a handle 164 of the tub 162 may extend through the opening 155 when the lid 154 is in the closed position. The handle 164 may also include a latch 165 that engages the pivotable lid 154 in the closed position to releasably secure the pivotable lid 154 in the closed position. The handle 164 may be resilient to allow the latch 165 to be repeatedly engaged and disengaged with the lid 154 to allow for repeated opening and closing of the lid 154 and removal and reinsertion of the tub 162 into the cradle or dock 153.

The tub 162 comprises a tub inlet 173 in communication with an air flow inlet 160 of the cradle or dock 153. An inlet seal 170 may be provided around the inlet aperture 166 to seal with the cradle or dock inlet 160. It should be appreciated that the inlet seal 170 may be overmoulded to the inlet aperture 166, or to the cradle or dock inlet 160 of the cradle or dock 153, or provided separately between the cradle or dock inlet 160 and the inlet aperture 166. The tub 162 may also include an outlet seal 158 at the outlet aperture 168 of a tub outlet 175 of the tub 162. The outlet seal 158 seals with a cradle or dock outlet 156 of the cradle or dock 153. It should be appreciated that the outlet seal 158 may be overmoulded to the tub 162 and/or the cradle or dock outlet 156 of the cradle 153, or provided separately between the two.

The tub 162 comprises a filling area, or sump, 174 into which water may be poured to fill the tub 162. A water level indicator 176 may be provided to indicate the water level in the tub 162. As shown in FIG. 41, the water level indicator may be angled. The angled water level indicator 176 may also direct the inlet air flow across the surface of the water in the tub 162. A filling seal 172 may be provided around the filling area 174 to seal the tub 162 against the tub of the cradle or dock 153. The filling seal 172 prevents water from flowing out of the tub and into the dock 153 if the humidifier is tilted, and also prevents the inlet air flow from the tub inlet 173 from flowing past the filling area 174.

Figure 45:
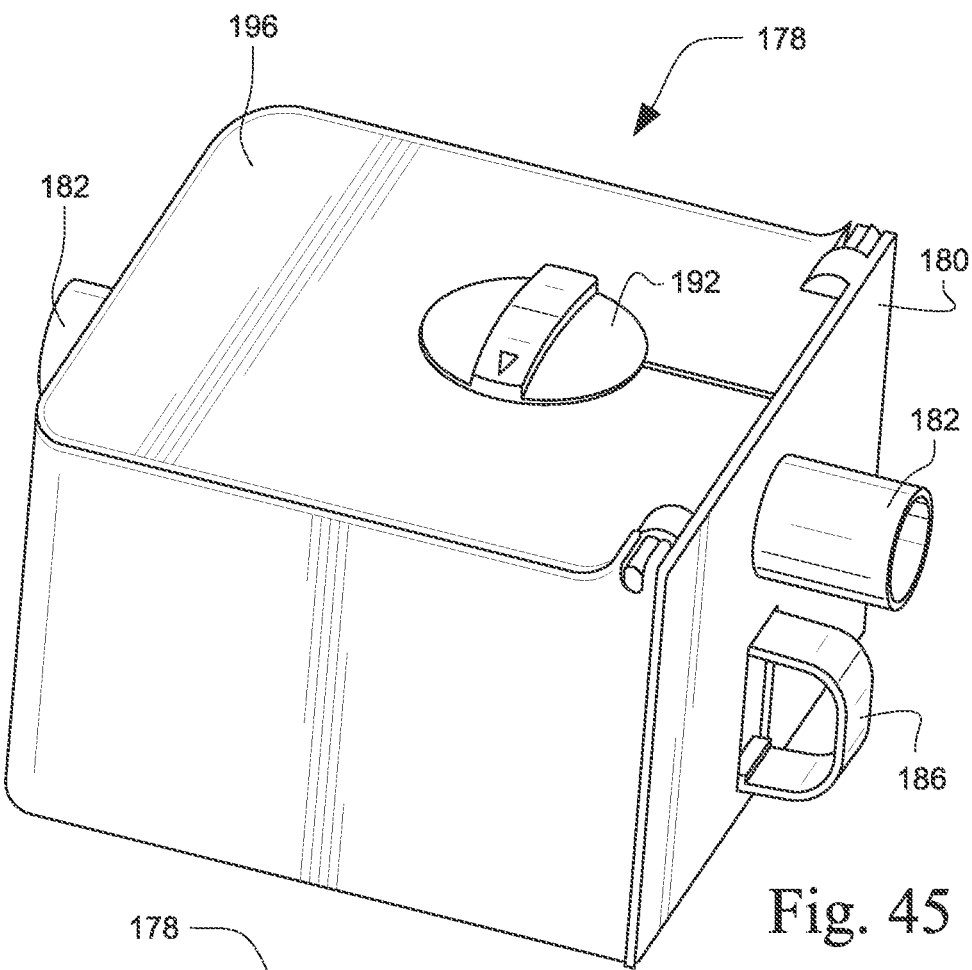
FIG. 45 is a view of a humidifier according to another example.
Figure 46:
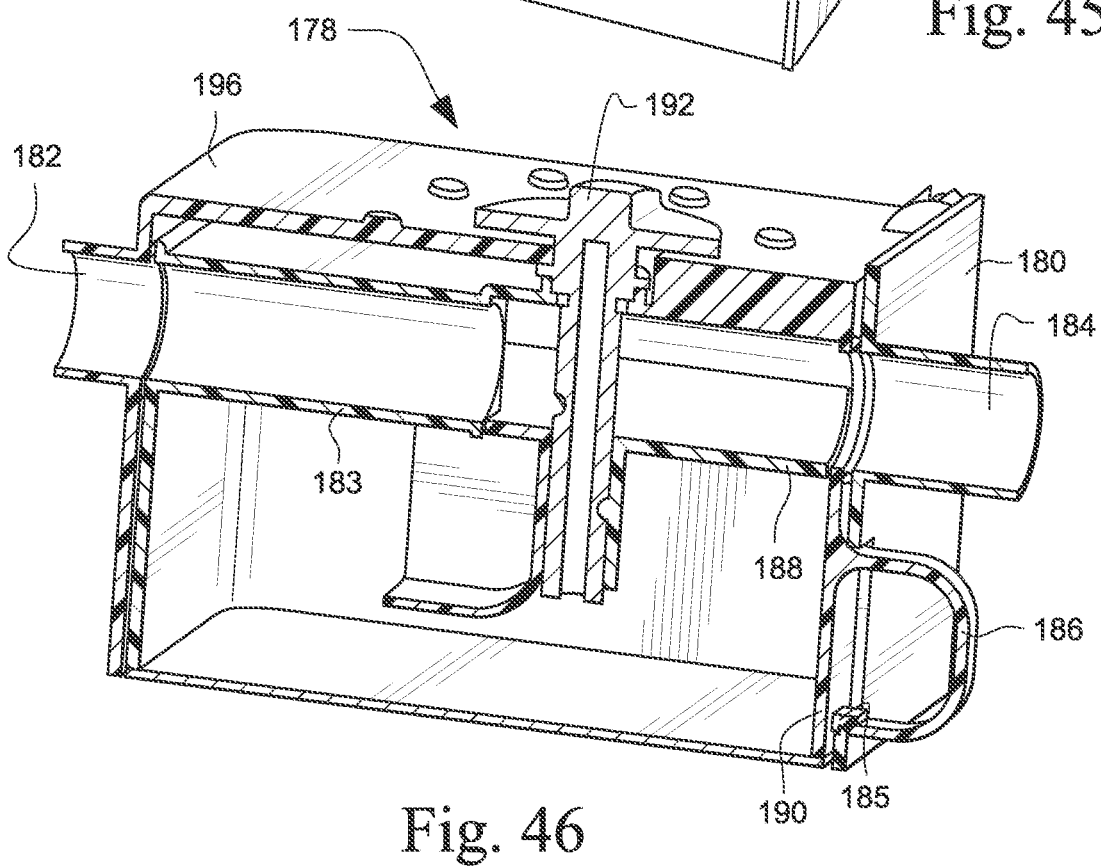
FIG. 46 is a cross section view of the humidifier of FIG. 45.
Figure 47:
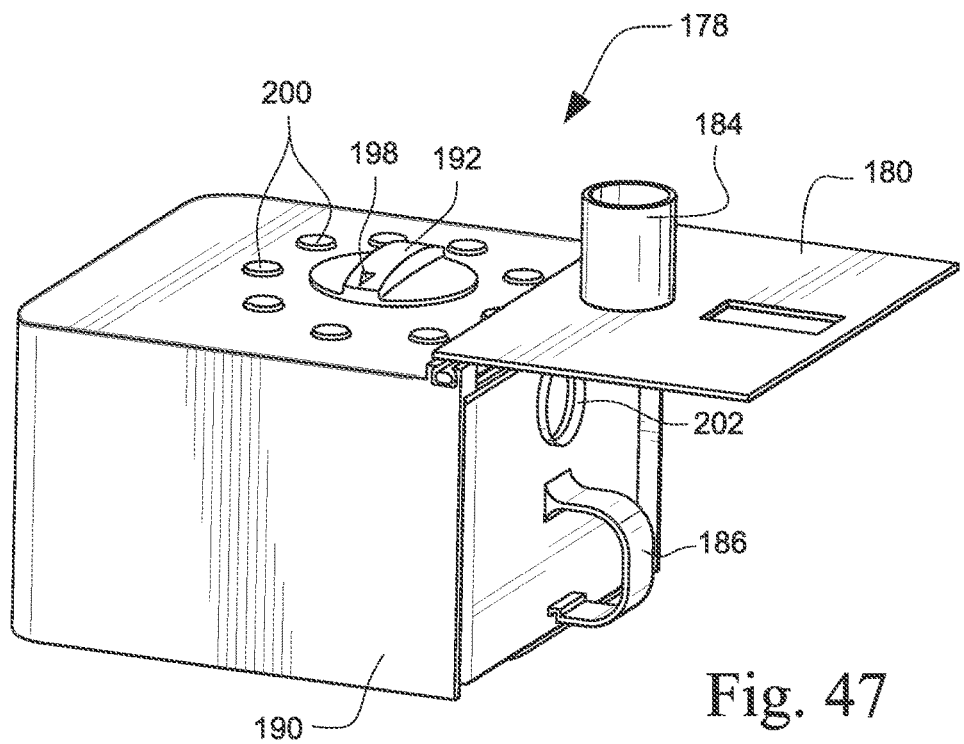
FIG. 47 is a view of the humidifier of FIG. 45 with a lid of the cradle in an open position.
Figure 48:
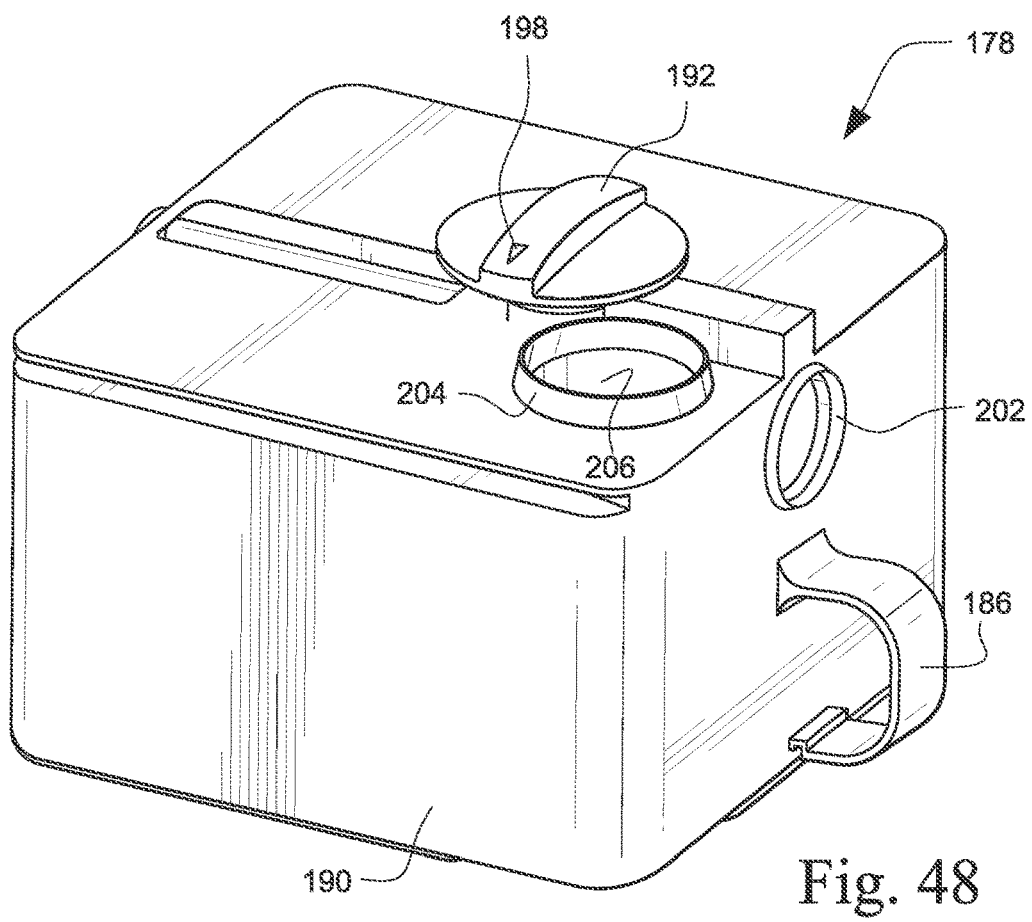
FIG. 48 is a view of the tub of the humidifier of FIG. 45.
Figure 49:
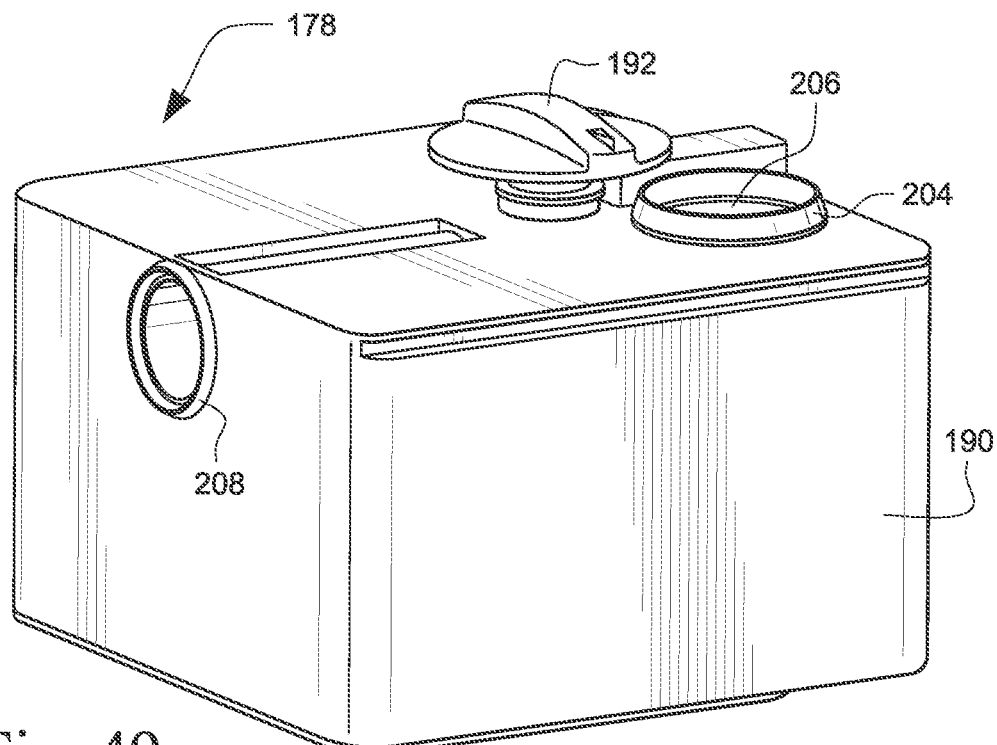
FIG. 49 is a rear perspective view of the tub of FIG. 45.

Referring to FIGS. 45-54, a humidifier 178 according to another example comprises a tub 190 provided in a cradle or dock 196. The cradle or dock 196 includes a hinged lid 180 and the tub 190 includes a handle 186 having a latch 185 for releasably retaining the hinged lid 180 in the closed position (FIGS. 45 and 46).

The tub 190 has a tub inlet 183 in communication with a cradle or dock inlet 182 of the cradle or dock 196. An inlet seal (e.g. an overmoulded seal) 208 is provided between the inlets 182, 183. The tub also has a tub seal (e.g. an overmoulded seal) 202 at the outlet that is in communication with a humidified air flow outlet 184 of the cradle or dock 196. A filling seal 204 is provided around a filling hole 206 to seal against the top of the cradle or dock 196.

Figure 53:
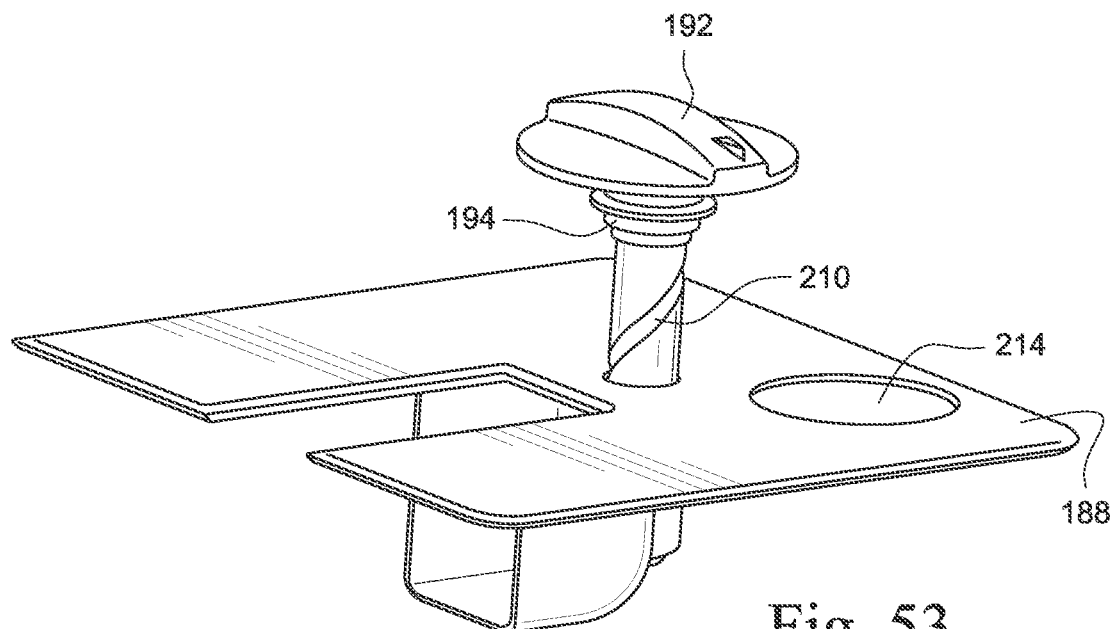
FIG. 53 is a view of elements of the flow adjustment mechanism of FIGS. 50-52.

A vane 188 is adjustably supported in the tub 190 by a vane adjuster 192. The vane adjuster 192 has a screw thread 210 on which the vane 188 is adjustably supported as shown in FIG. 53. The position of the vane 188 is adjusted by turning the vane adjuster 192 and the vane 188 moves up and down along the screw thread 210 to provide either continuous movement or to move in discrete amounts. A vane seal 194 is provided between the adjuster 192 and the tub 190. The tub inlet 183 has straight sides configured to seal with the movable vane 188. The vane adjuster 192 has an alignment mark 198 that indicates the position of the adjuster 192 relative to indicia 200 on the tub 190, and thus the position of the vane 188 relative to the interior of the tub 190.

Figure 50:
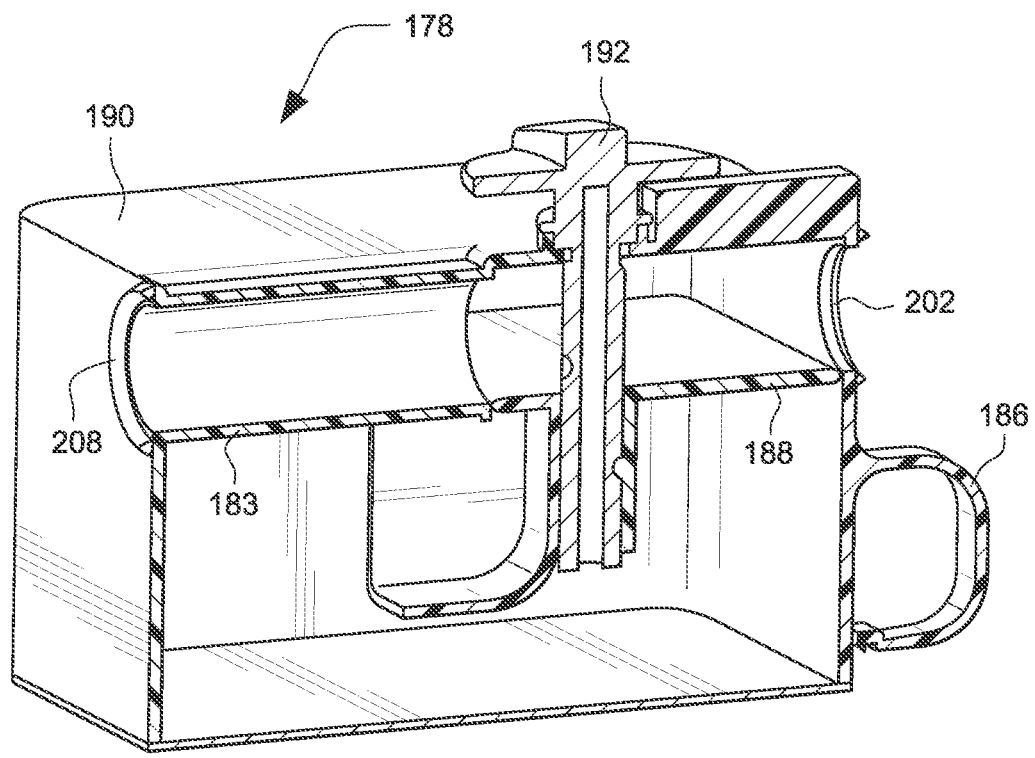
FIG. 50 is a cross section view of the tub of the humidifier of FIG. 45 with a flow adjustment mechanism in a first position.
Figure 51:
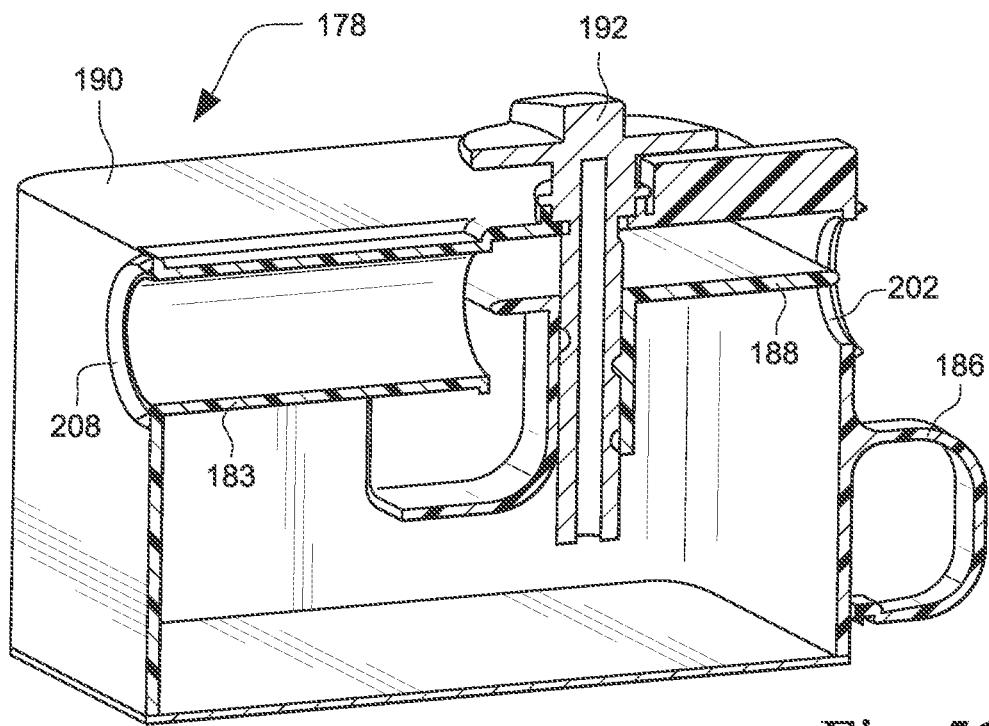
FIG. 51 is a cross section view of the tub of the humidifier of FIG. 45 with the flow adjustment mechanism in a second position.
Figure 52:
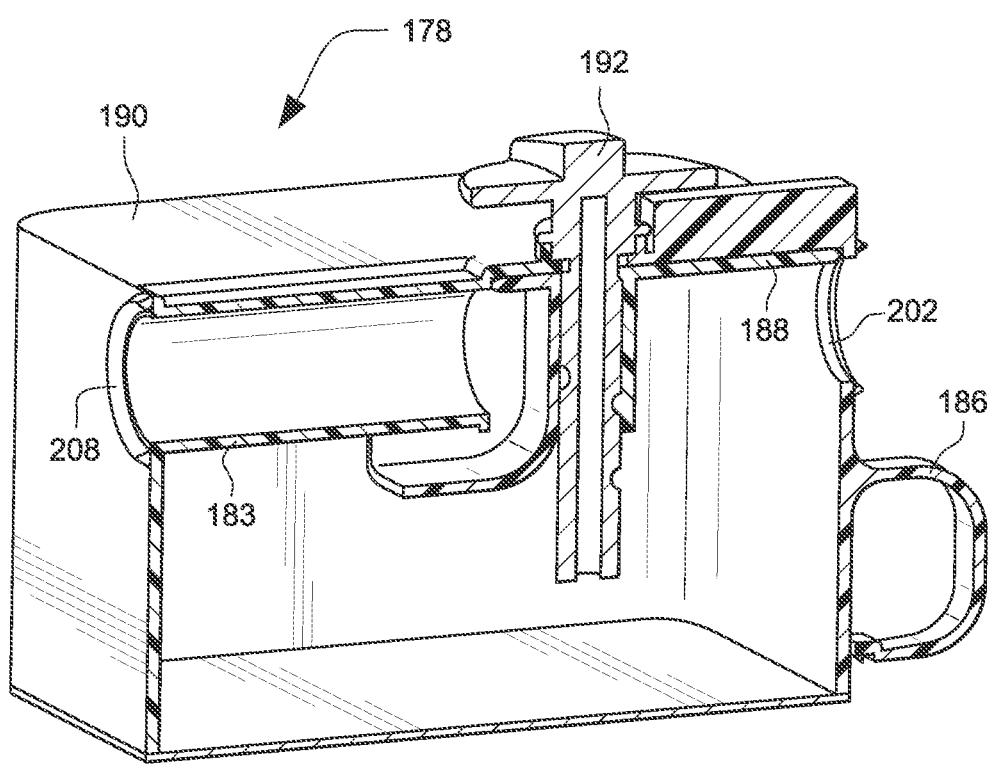
FIG. 52 is a cross section view of the tub of the humidifier of FIG. 45 with the flow adjustment mechanism in a third position.

Referring to FIG. 50, the vane 188 is in the lowest position in the tub 190. The entire air flow in the tub inlet 183 is diverted to the outlet 184 without contacting the surface of the water in the tub 190. In FIG. 51, the vane is in a middle position and a portion (e.g. 50%) of the air flow from the tub inlet 183 is diverted to the tub outlet 184 and the remainder (e.g. 50%) of the air flow from the tub inlet 183 is diverted by the vane into the tub 190 and across the surface of the water, and then through the tub outlet 184 of the cradle or dock 196. This provides a portion of the humidifier's output to the patient. Thus, the movable vane 188 is arranged to direct between 0% and 100% of the flow of breathable gas from the inlet 183 to the outlet 184 without contacting a surface of the supply of water. The indicia 200 on the tub 190 may be labeled to indicate what portion of the inlet air flow is being humidified. FIG. 52 shows the vane 188 in the highest position where the entire air flow from the inlet 183 is diverted into the tub 190 and across the surface of the water. This provides the entire output of the humidifier to the patient.

Figure 54:
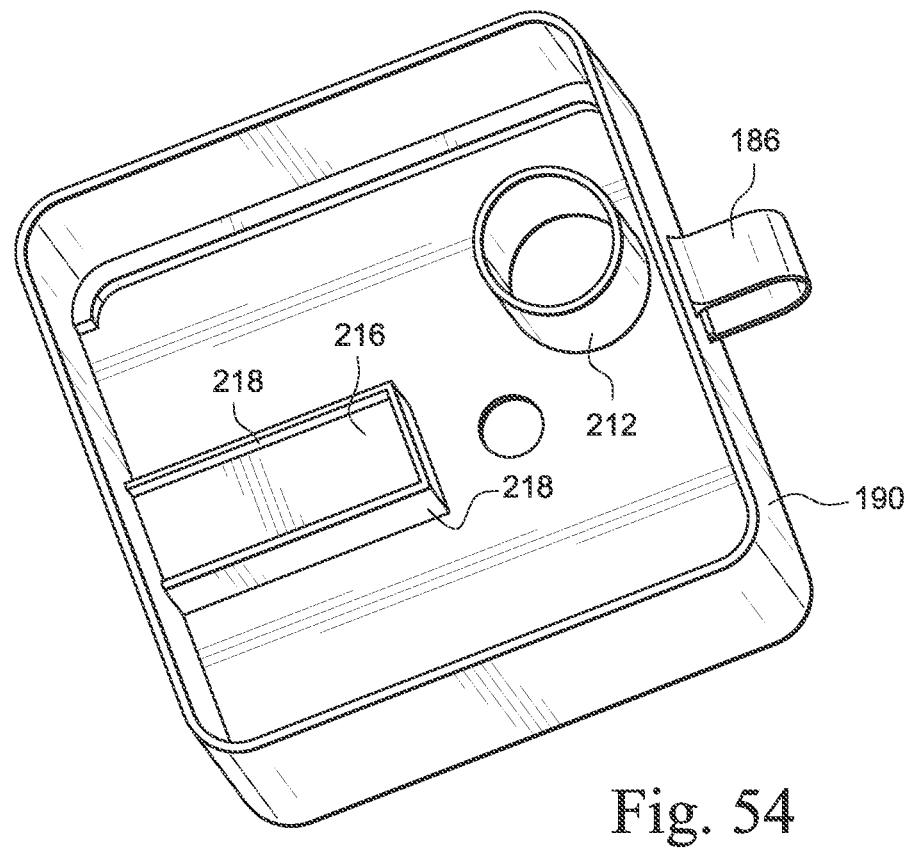
FIG. 54 is a perspective view of a tub base of the tub of the humidifier of FIG. 45.
Figure 55:
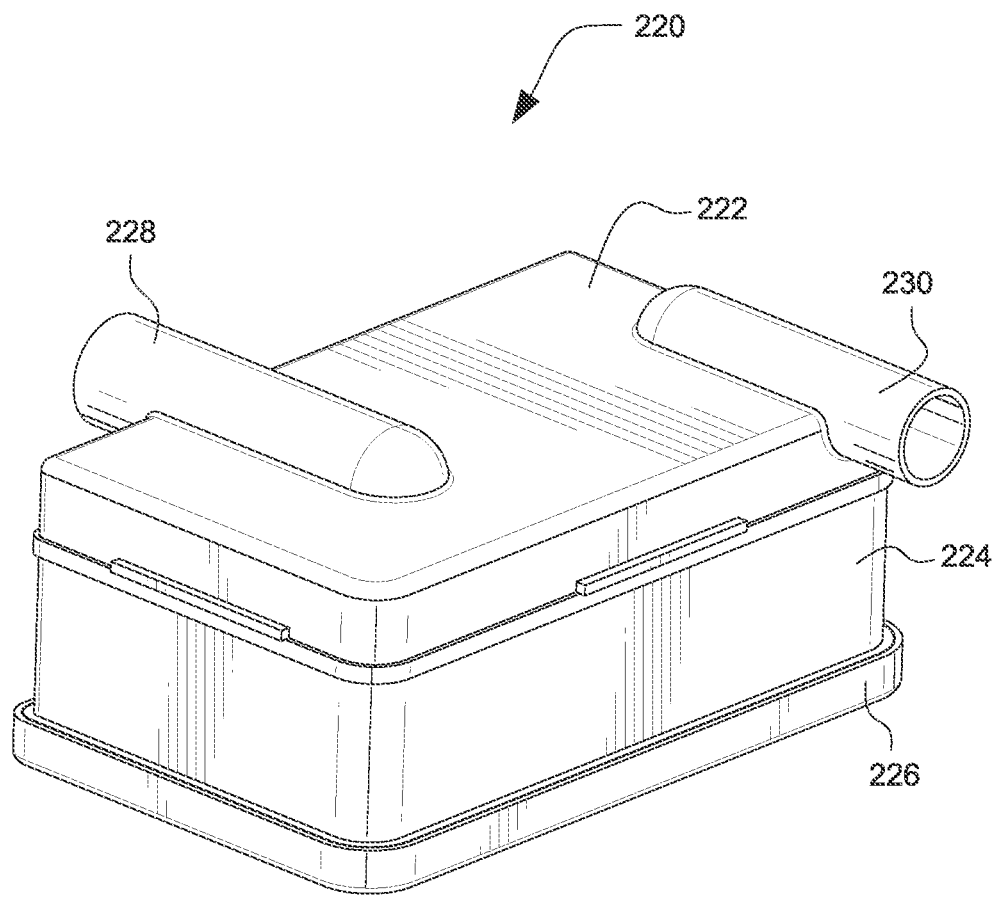
FIG. 55 is a perspective view of a humidifier according to another example of the technology.
Figure 56:
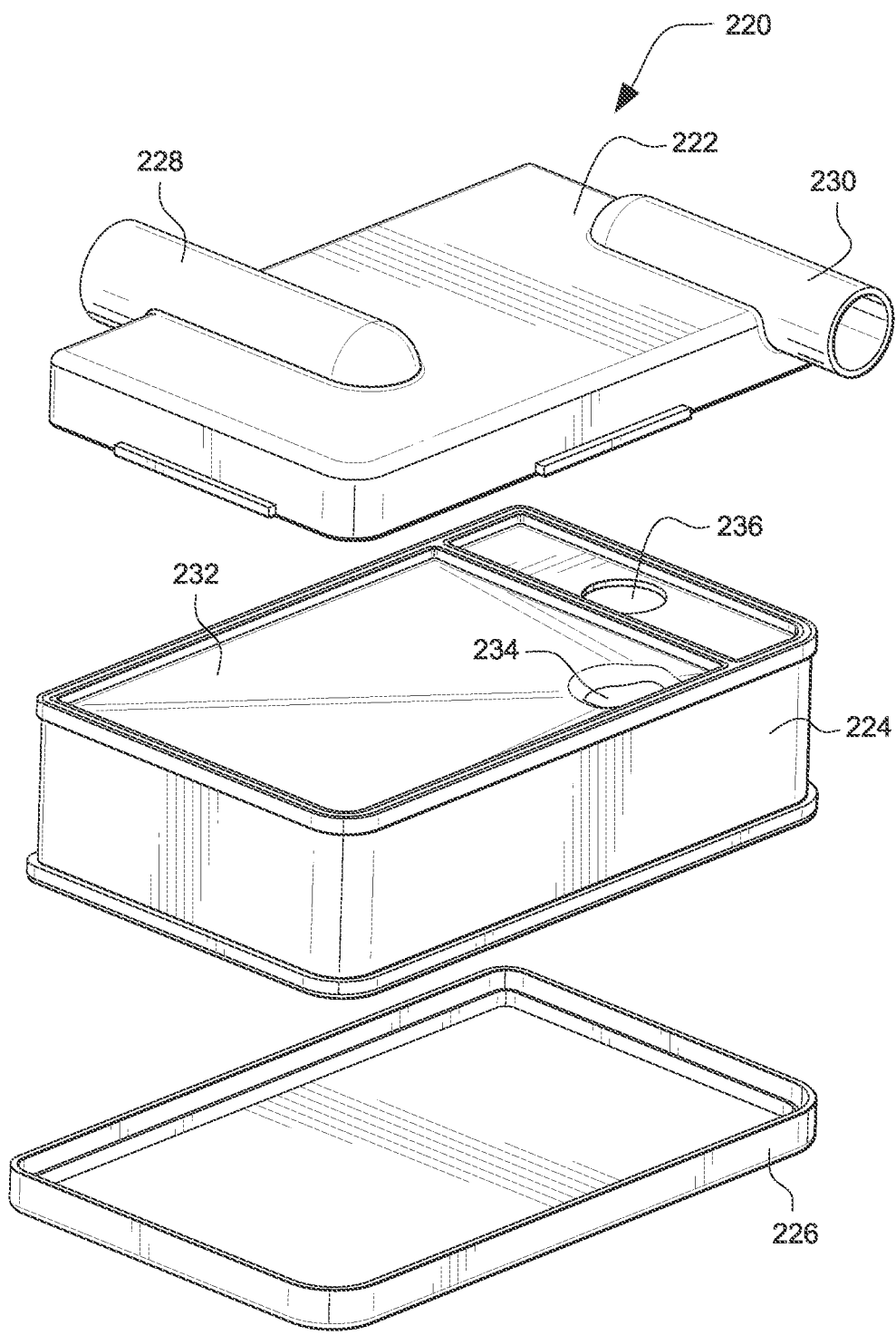
FIG. 56 is an exploded assembly view of the humidifier of FIG. 55.
Figure 57:
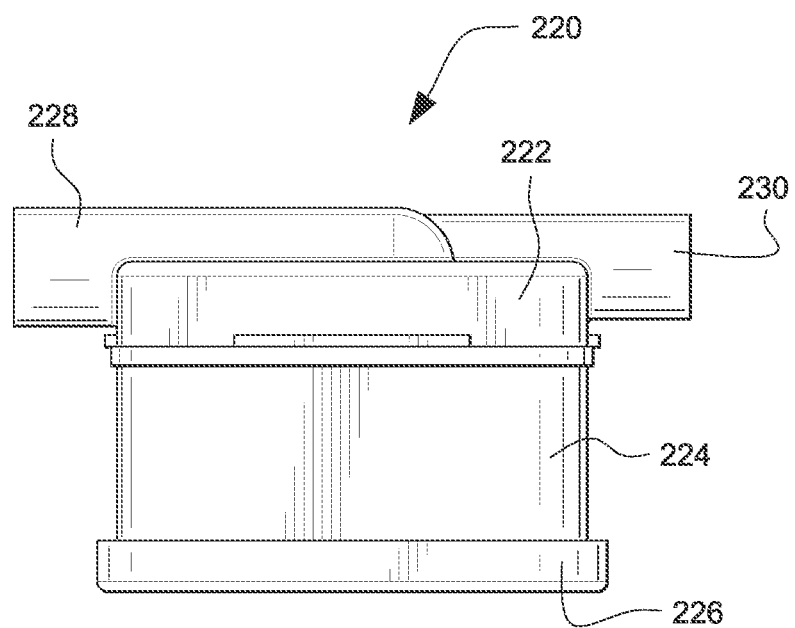
FIG. 57 is a side view of the humidifier of FIG. 55.
Figure 58:
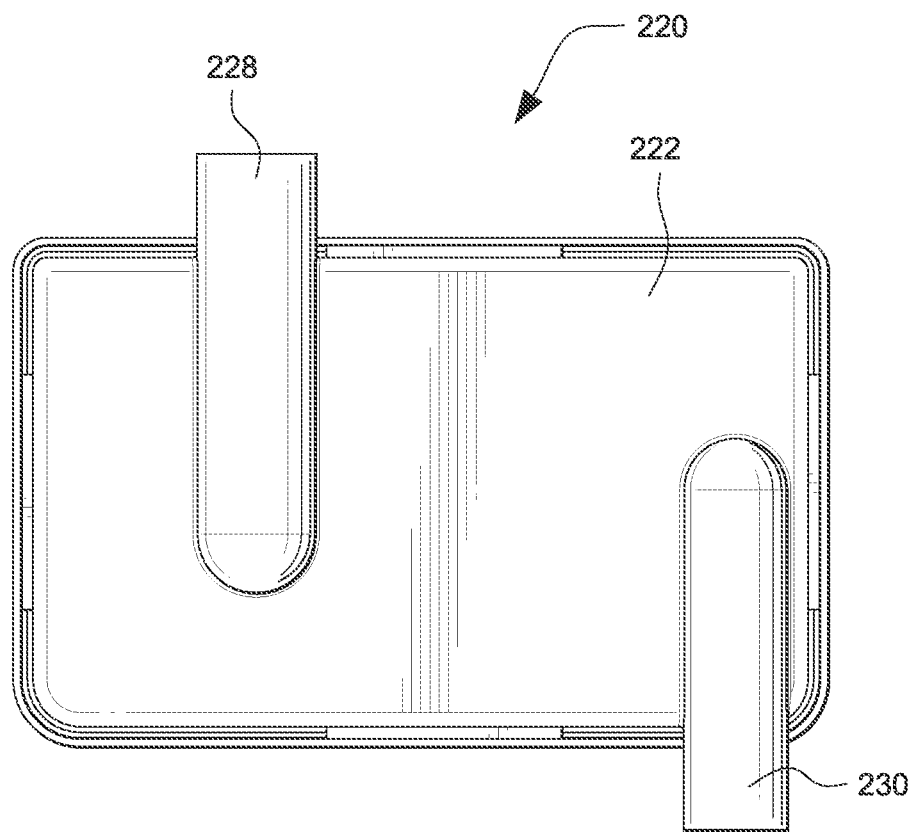
FIG. 58 is a plan view of the humidifier of FIG. 55.
Figure 59:
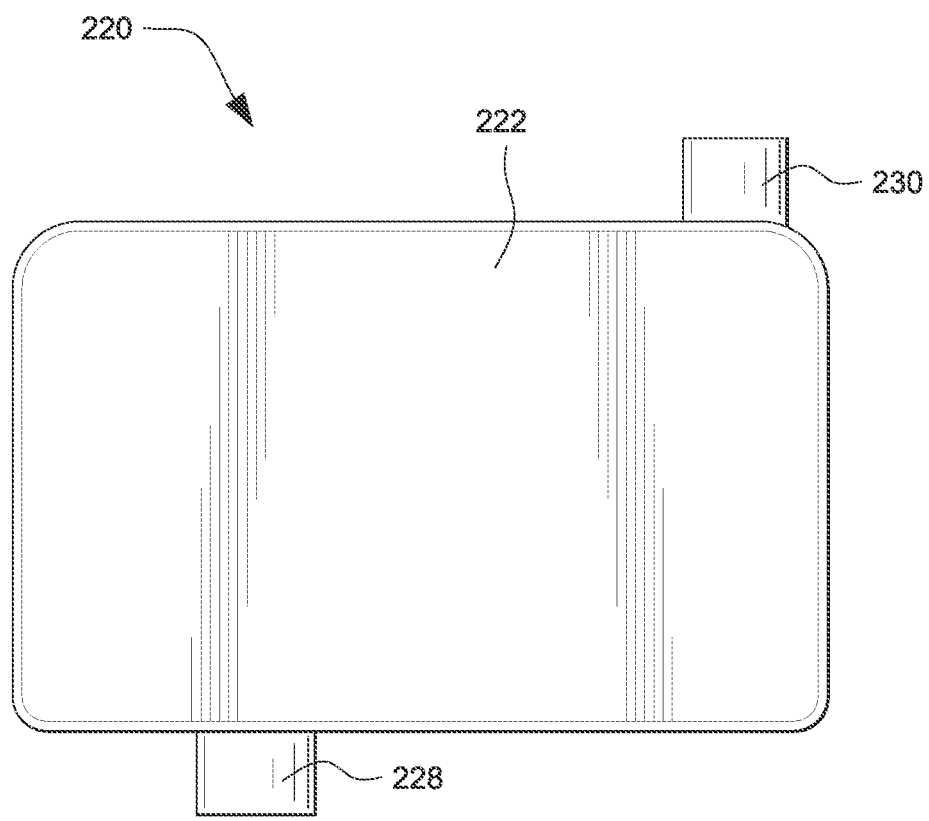
FIG. 59 is a bottom view of the humidifier of FIG. 55.
Figure 60:
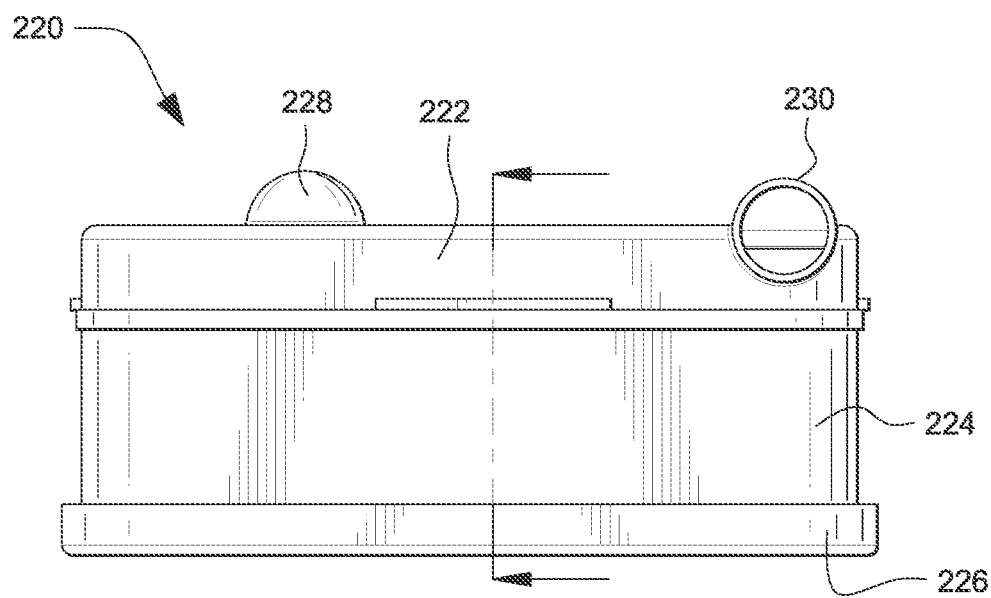
FIG. 60 is a rear view of the humidifier of FIG. 55.
Figure 61:
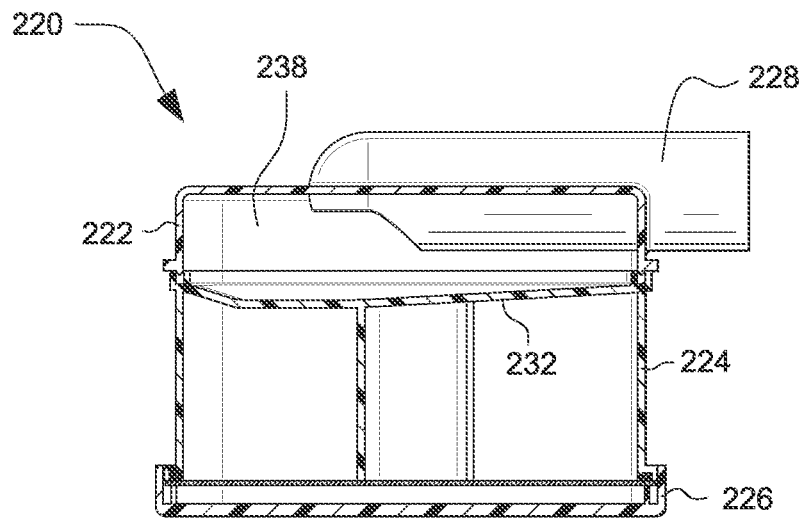
FIG. 61 is a cross section view of the humidifier of FIG. 55.
Figure 62:
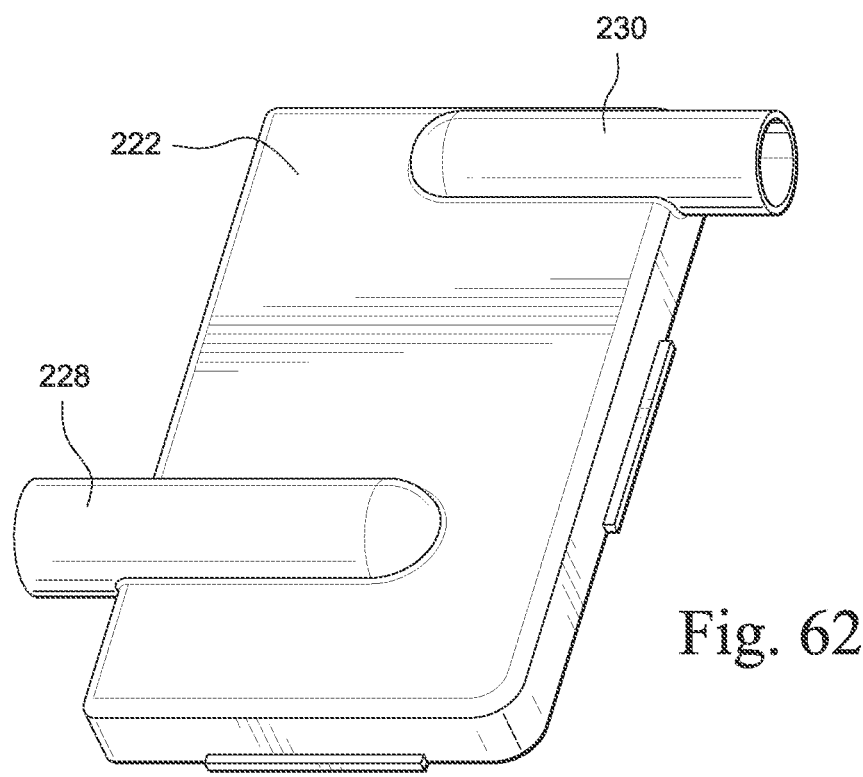
FIG. 62 is perspective view of a top lid portion of the humidifier of FIG. 55.
Figure 63:
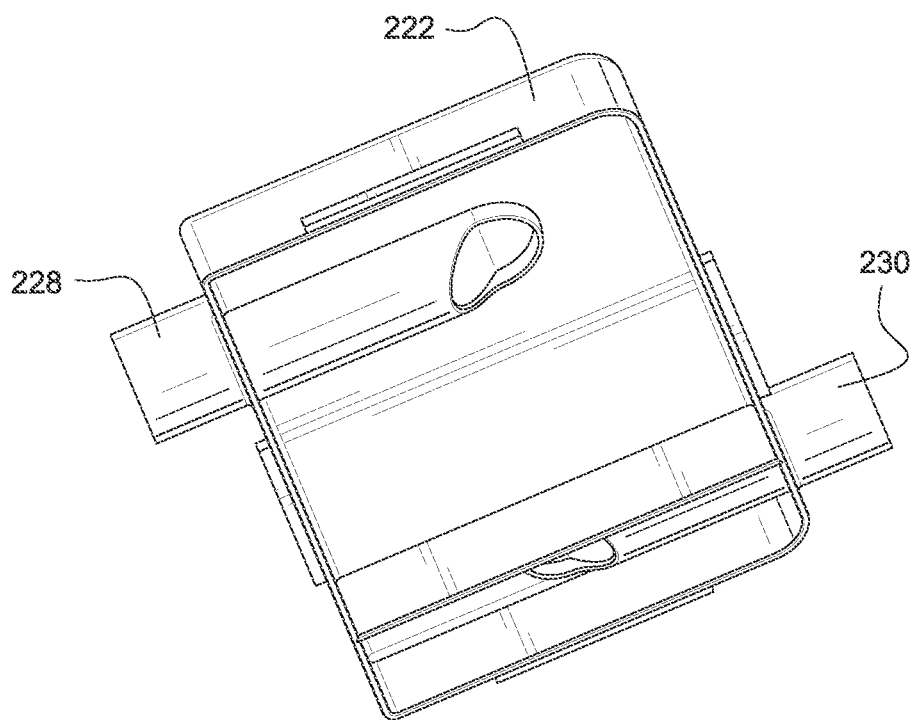
FIG. 63 is a bottom perspective view of the top lid portion of FIG. 62.
Figure 64:
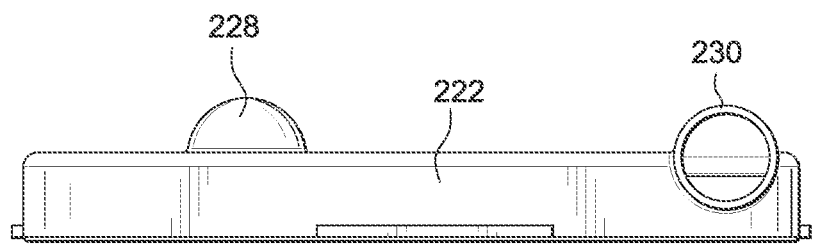
FIG. 64 is rear view of the top lid portion of FIG. 62.
Figure 65:
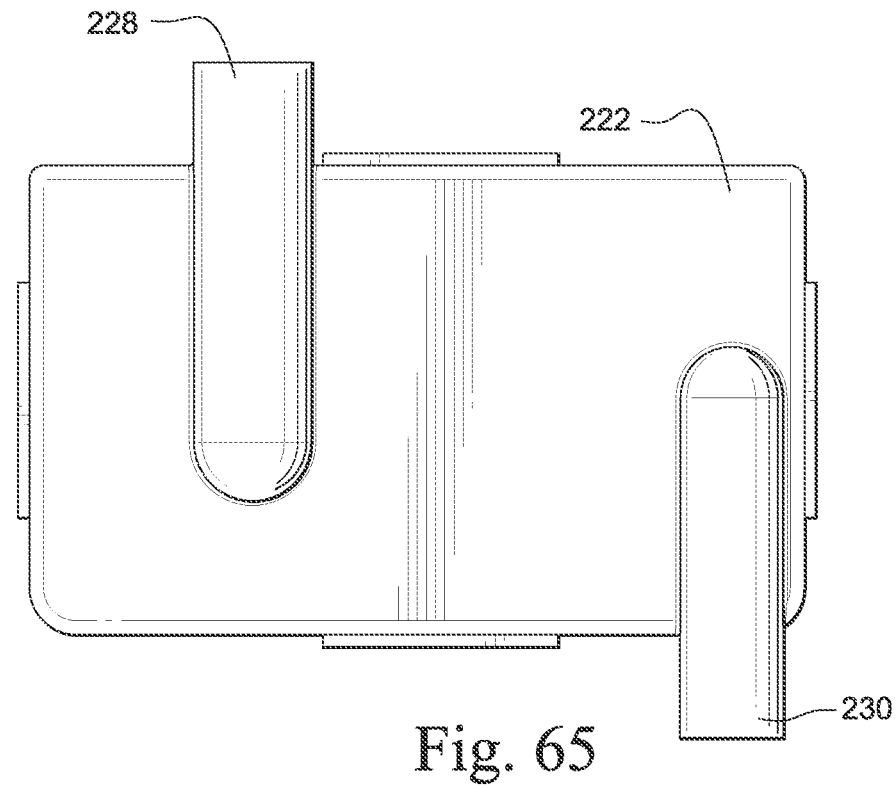
FIG. 65 is a plan view of the top lid portion of FIG. 62.
Figure 66:
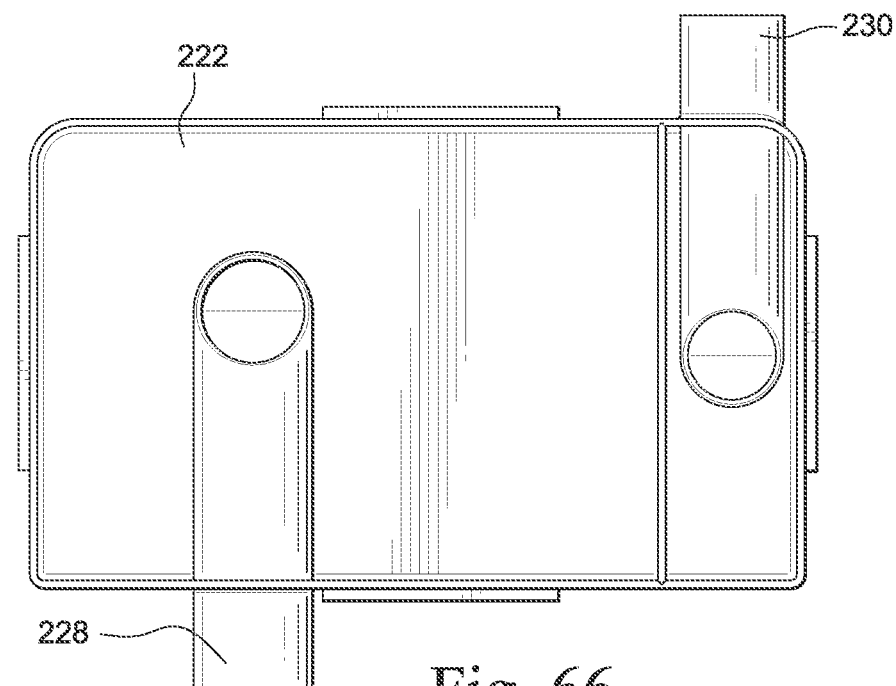
FIG. 66 is a bottom view of the top lid portion of FIG. 62.
Figure 67:
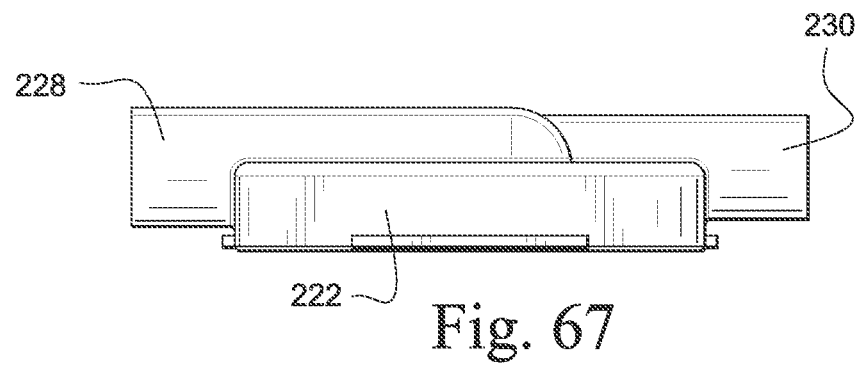
FIGS. 67 and 68 are side views of the top lid portion of FIG. 62.
Figure 68:
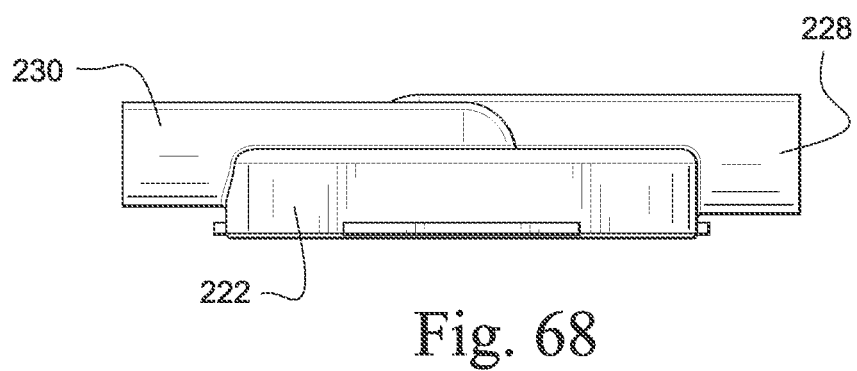
Figure 69:
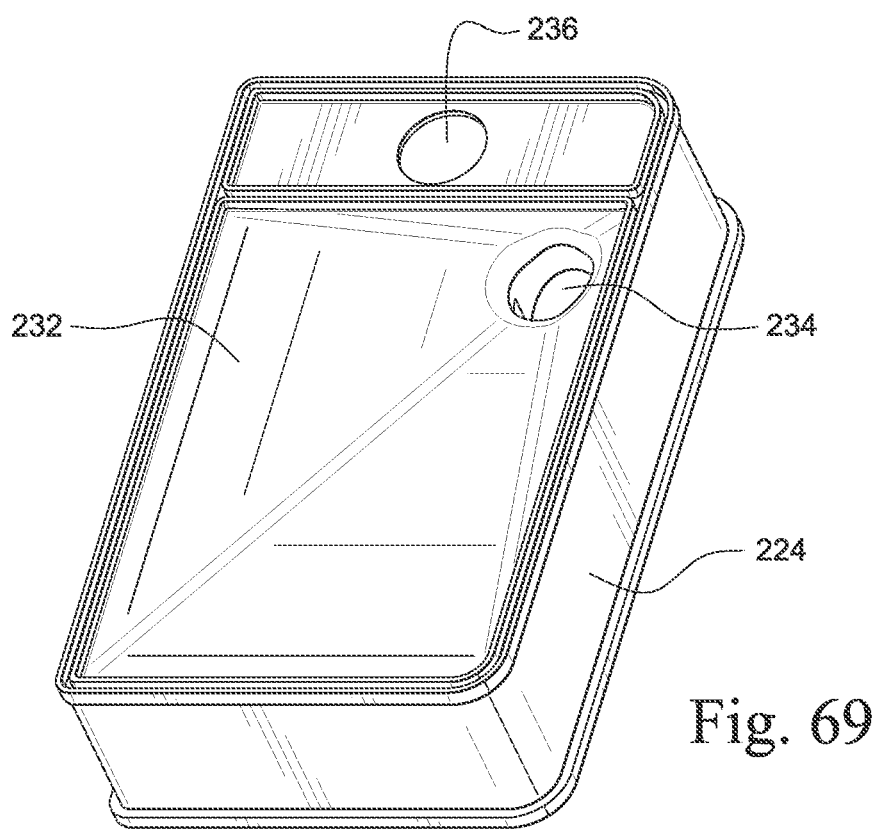
FIG. 69 is a top perspective view of a middle portion of the humidifier of FIG. 55.

Referring to FIGS. 53 and 54, the tub inlet 183 of the tub 190 may have flat sides 218 to allow a close seal to the vane 188. Although a small gap may exist between the tub inlet 183 and the vane 188, the air flow through the gap is negligible compared to the flow through the outlet. The tub inlet 183 may also be positioned in the tub 190 to prevent or reduce spillback of water from the tub through the tub inlet 183 into the cradle or dock inlet 182 of the cradle or dock 196. The filling tube 212 may extend through the hole 214 in the vane 188 as the position of the vane is adjusted in the tub 190.

The water in the tub 190 may be maintained at a constant temperature. The control of the humidity mechanically through the adjustable vane 188 reduces the cost compared to electronic temperature control. It should be appreciated, however, that a low cost PTC heater may be provided to the humidifier.

The adjustment of the vane 188 allows very fine increments of humidity output, for example between 0 (ambient) and 100% humidity can be achieved. Although the drawings show a discrete number of indicia 200 indicating the position of the vane 188, it should be appreciated that the position of the vane 188 is continuously adjustable within the tub 190 and the vane may assume an essentially infinite range of positions within the tub. By providing the water at an elevated temperature, bacteria and germs within the water may be eliminated from the humidified air delivered to the patient.

Humidifier with Two Chambers

Referring to FIGS. 55-75, a humidifier 220 includes a tub that has three portions. The top lid portion 222 has an inlet conduit 228 for an incoming air flow (e.g. from a flow generator) and an outlet conduit 230 for the humidified air flow. Both inlet and outlet conduits 228, 230 are located on the top lid portion 222 of the tub. The middle and bottom portions 224, 226 form a reservoir chamber which holds water. The bottom portion 226 may include a heating base, or alternatively it may include a heat conductive base adapted to be in contact with a heating base, to transfer heat to the water held inside the reservoir. The top 232 of the middle portion 224 and the locations of an air flow inlet hole 234 and a humidified air flow outlet hole 236 function to keep the water in the reservoir chamber separated from the top chamber 238 where the air flow enters in and out from the inlet and outlet conduits 228, 230. Accordingly, the humidifier 220 provides spill back protection so water is prevented from spilling back into the inlet and outlet conduits 228, 230. Similarly, the humidifier 220 also provides protection against water being spilled out if the tub is tilted or bumped or shook.

Figure 70:
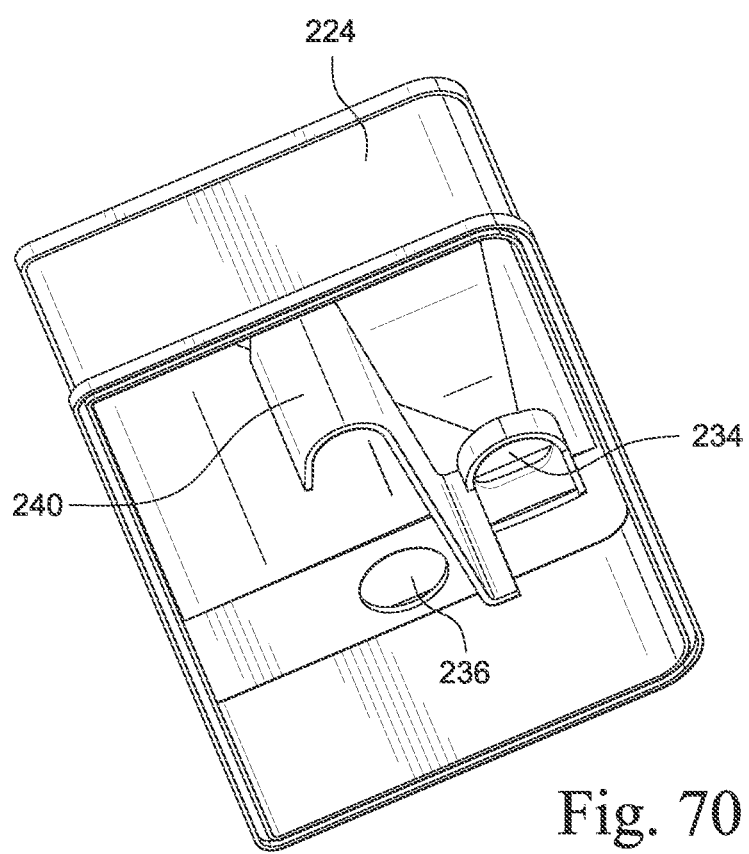
FIG. 70 is a bottom perspective view of the middle portion of FIG. 69.
Figure 71:
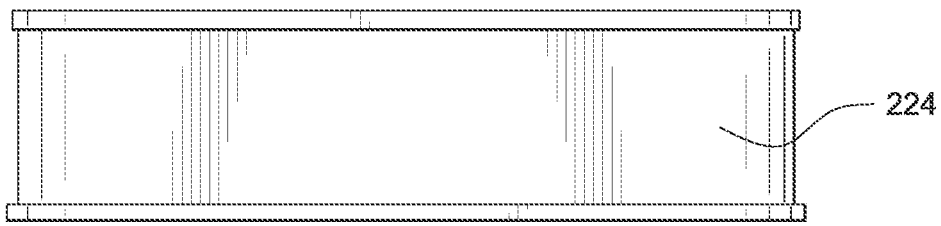
FIG. 71 is a side view of the middle portion of FIG. 69.
Figure 72:
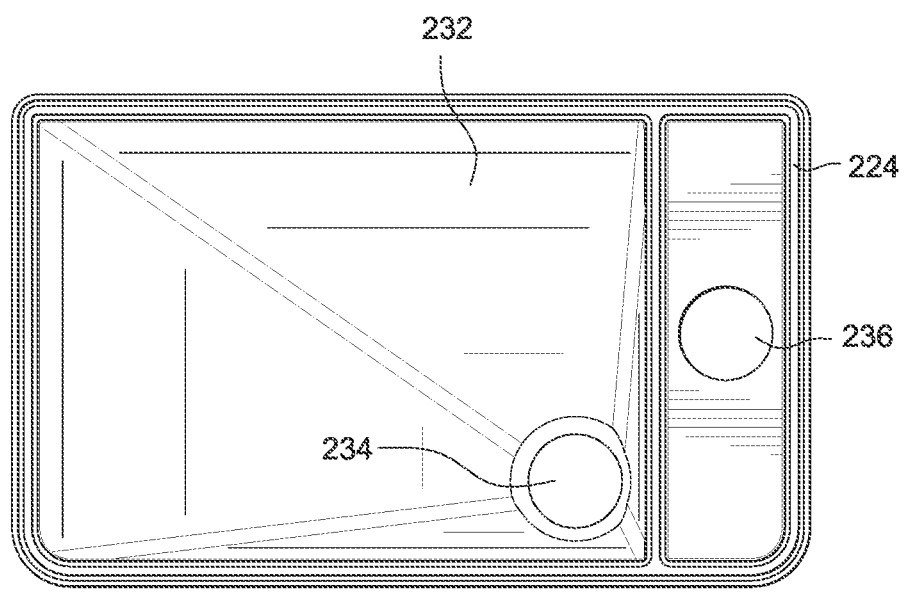
FIG. 72 is a plan view of the middle portion of FIG. 69.
Figure 73:
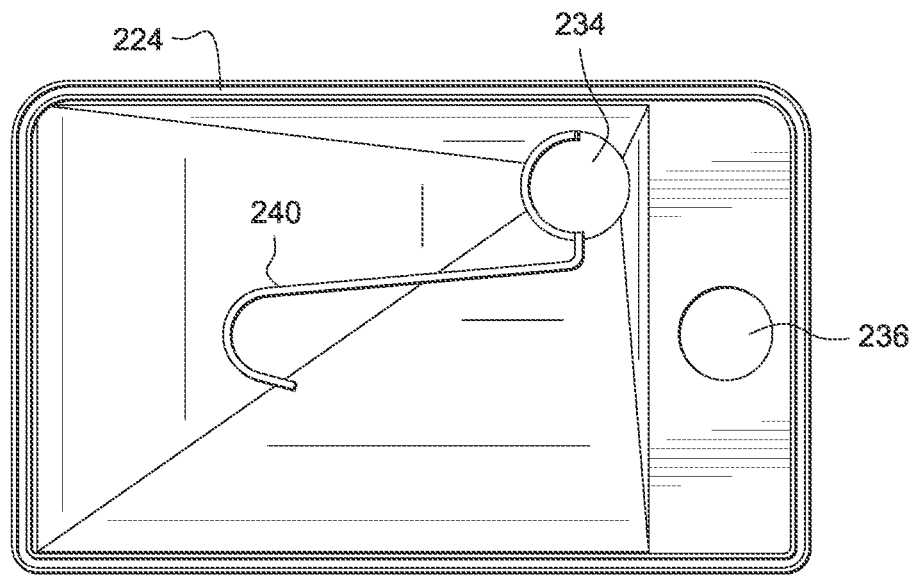
FIG. 73 is a bottom view of the middle portion of FIG. 69.
Figure 74:
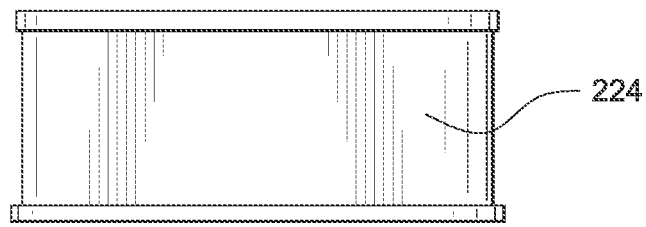
FIGS. 74 and 75 are side views of the middle portion of FIG. 69.
Figure 75:
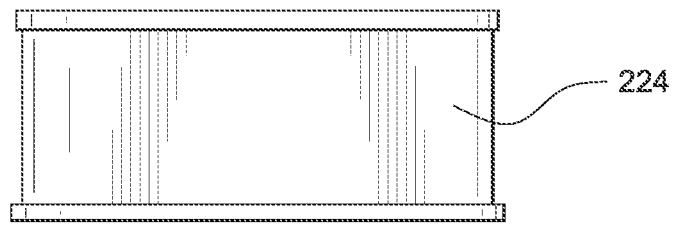

As shown in FIGS. 70 and 73, a baffle 240 may be provided at the inlet hole 234. The baffle may function similarly to the baffle, or wall, disclosed and described in U.S. Application 61/522,763, filed Aug. 12, 2011, the entire contents of which are incorporated herein by reference, to direct airflow across the water surface. The humidifier 220 is also a simple design that is easy to mould and assemble.

While the technology has been described in connection with what are presently considered to be the most practical and preferred examples of the technology, it is to be understood that the technology is not to be limited to the disclosed examples, but on the contrary, are intended to cover various modifications and equivalent arrangements included within the spirit and scope of the technology. Also, the various examples described above may be implemented in conjunction with other examples, e.g., aspects of one example may be combined with aspects of another example to realize yet other examples of the technology. Further, each independent feature or component of any given assembly may constitute an additional example. Furthermore, each individual component of any given assembly, one or more portions of an individual component of any given assembly, and various combinations of components from one or more examples may include one or more ornamental design features. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

Table of items listed in figures

| ITEM | NUMBER in FIGURES |
|---|---|
| humidifier or humidifier tub | 2, 50, 102, 152, 178, 220, 332 |
| cradle | 3 |
| outer tub or tub base | 4, 60 |
| inner reservoir or inner tub | 6, 56 |
| tub | 6 |
| valve | 8 |
| spring stop | 9 |
| valve spring | 10 |
| valve stem | 12 |
| heat conductive base or heater plate | 14, 64 |
| lid | 16, 52, 154, 180 |
| air lock | 18 |
| water | 20, 131, 132,, 133, 134 |
| bottom | 22 |
| tilt control labyrinth | 24 |
| opening | 25 |
| primary nozzle or first nozzle | 26 |
| secondary nozzle or second nozzle | 28 |
| valve seat | 30 |
| first groove | 32 |
| second groove | 34 |
| lid rib or lid projection | 36 |
| tub rib or tub projection | 38 |
| cavity | 40, 55 |
| inlet aperture | 41 |
| inlet tube | 42, 62, 98,120 |
| outer tub outlet | 43 |
| outlet tube | 44, 64, 100, 122 |
| cavity water level | 46 |
| tilt labyrinth water level | 48, 68 |
| lid seal | 54 |
| rocker valve or rocker arm | 58 |
| water feed nozzle | 70 |
| breather tube | 72 |
| inner seal | 74 |
| tub seal | 75 |
| rocker valve supports | 76 |
| axle | 78 |
| rocker valve biasing element | 80 |
| valve element | 82 |
| handle | 84 |
| valve seat | 86 |
| top (of rocker valve) | 88 |
| Humidifier tub or tub | 90, 436, 3736 |
| tub lid | 92 |
| tub base | 94 |
| inlet or air flow inlet | 95, 120 |
| outlet | 96, 122 |
| floatable material | 97, 99 |
| lid | 104 |
| intermediate levels | 106, 110, 114 |
| first level | 106 |
| first filler conduit | 108 |
| second level | 110 |
| second filler conduit | 112 |
| third level | 114 |
| third filler conduit | 116 |
| bottom chamber | 118 |
| air gap height | 124 |
| indicia | 126 |
| grid pattern | 128 |
| grid | 130 |
| dock or cradle | 334, 153 |
| first tub inlet tube | 335 |
| first tub | 336 |
| end inner wall | 337, 3747 |
| dock inlet | 338 |

-continued

Table of items listed in figures

| ITEM | NUMBER in FIGURES |
|---|---|
| dock outlet | 340 |
| inlet seal | 342 |
| latch | 344, 3744 |
| second tub inlet | 345 |
| second tub | 346 |
| outlet seal | 348 |
| second tub outlet | 349 |
| heater element | 350, 3758 |
| lid | 154 |
| opening | 155 |
| cradle or dock outlet | 156 |
| outlet seal | 158 |
| cradle or dock inlet | 160 |
| tub | 162 |
| handle | 164 |
| latch | 165 |
| inlet aperture | 166 |
| outlet aperture | 168 |
| inlet seal | 170 |
| filling seal | 172 |
| tub inlet | 173 |
| filling area or sump | 174 |
| tub outlet | 175 |
| water level indicator | 176 |
| cradle or dock inlet | 182 |
| tub inlet | 183 |
| tub outlet | 184 |
| latch | 185 |
| handle | 186 |
| vane | 188 |
| tub | 190 |
| vane adjuster | 192 |
| seal | 194 |
| dock | 196 |
| alignment mark | 198 |
| indicia | 200 |
| tub seal | 202 |
| filling hole | 206 |
| inlet seal | 208 |
| screw thread | 210 |
| filling tube | 212 |
| hole | 214 |
| flat sides | 218 |
| top lid portion | 222 |
| middle portion | 224 |
| bottom portion | 226 |
| inlet conduit | 228 |
| outlet conduit | 230 |
| top (of middle portion) | 232 |
| inlet hole | 234 |
| outlet hole | 236 |
| top chamber | 238 |
| baffle | 240 |
| tub inlet | 3735 |
| tub outlet | 3737 |
| baffle | 3749 |
| flow generator | 3750 |
| flow generator outlet | 3752 |
| humidified flow inlet | 3754 |
| tubing connector | 3756 |
| heating element | 3758 |
| adjustable portion | 438 |
| expansion portion | 440 |
| base portion | 442 |
| gap | 444 |
| gap seal | 446 |

What is claimed is:

1. A positive airway device configured to deliver a pressurized flow of humidified respiratory gas to a patient's airways, the positive airway device comprising:
 a flow generator comprising:
  a blower portion comprising a blower configured to pressurize the flow of respiratory gas;

a docking portion laterally adjacent to the blower portion, the docking portion being separated from the blower portion by a divider, the docking portion comprising a cavity bound by the divider, a lower wall extending horizontally from the divider, an upper wall opposite the lower wall, and a pair of opposing side walls adjacent to the divider and extending to the upper wall, the cavity being open on a lateral side opposite the divider;

a blower outlet opening in the divider that is pneumatically connected to the blower;

a heater plate on a lower side of the docking portion;

a housing for the blower portion and the docking portion;

an air delivery tube connector on a lateral side of the housing; and a humidified flow conduit with a humidified flow inlet adjacent to the blower outlet opening, the humidified flow inlet being configured to convey the pressurized flow of humidified respiratory gas from the docking portion to the air delivery tube connector; and a humidifier tub configured to be laterally received by the docking portion through the open lateral side of the cavity, the humidifier tub comprising:

a first tub subsection comprising an air inlet opening and an air outlet opening;

a second tub subsection laterally adjacent to the first tub subsection;

a flange extending outwardly from an outer surface of the humidifier tub to form a transition between the first and second tub subsections, the humidifier tub being configured so that when the humidifier tub is fully received by the docking portion, the first tub subsection is enclosed within the cavity and the second tub subsection remains outside the cavity;

a tub base forming a bottom side of the humidifier tub and comprising a heat conducting base plate configured to engage the heater plate of the docking portion when the humidifier tub is received within the cavity; and a latching projection located on a top side of or above the first tub subsection, wherein the docking portion comprises a recess and the latching projection of the humidifier tub is configured to engage the recess of the docking portion to releasably secure the humidifier tub to the docking portion, wherein the air inlet opening of the humidifier tub is configured to complete a sealed airpath from the blower, through the divider, and into the humidifier tub upon the humidifier tub being fully received by the docking portion, and wherein the air outlet opening of the humidifier tub is configured to complete a sealed airpath from the humidifier tub to the air delivery tube connector upon the humidifier tub being fully received by the docking portion.

2. The positive airway device of claim 1, wherein the blower outlet opening and the humidified flow inlet are laterally adjacent to each other.

3. The positive airway device of claim 1, wherein a humidified flow pathway extends through the divider.

4. The positive airway device of claim 1, wherein the blower outlet opening and the humidified flow inlet are positioned at the same height.

5. The positive airway device of claim 1, wherein the flange is configured to abut a rim of the open lateral side of the cavity when the humidifier tub is fully received by the docking portion.

6. The positive airway device of claim 1, wherein an outside surface of the second tub subsection is flush with an outside surface of the housing when the humidifier tub is fully received by the docking portion.

7. The positive airway device of claim 1, wherein the air delivery tube connector is located on a blower portion side of the flow generator.

8. The positive airway device of claim 1, wherein the air inlet opening of the humidifier tub is configured to receive the pressurized flow of respiratory gas in a horizontal direction, and wherein the air outlet opening of the humidifier tub is configured to discharge the pressurized flow of humidified respiratory gas in a horizontal direction.

9. The positive airway device of claim 1, wherein the humidifier tub further comprises an air inlet conduit extending laterally inwardly from the air inlet opening and an air outlet conduit extending laterally inwardly from the air outlet opening.

10. The positive airway device of claim 1, wherein the air outlet opening and the air inlet opening of the humidifier tub are located on the same planar side wall.

11. The positive airway device of claim 1, wherein the air inlet opening and the air outlet opening of the humidifier tub are coplanar.

12. The positive airway device of claim 1, wherein a central longitudinal axis of the air inlet opening of the humidifier tub is parallel to a central longitudinal axis of the air outlet opening.

13. The positive airway device of claim 1, wherein the heater plate is located on the lower wall of the cavity of the docking portion.

14. The positive airway device of claim 1, wherein the blower outlet opening and the humidified flow inlet are laterally adjacent to each other, wherein a humidified flow pathway extends through the divider, wherein the air delivery tube connector is located on a blower portion side of the flow generator, wherein the air inlet opening of the humidifier tub is configured to receive the pressurized flow of respiratory gas in a horizontal direction, wherein the air outlet opening of the humidifier tub is configured to discharge the pressurized flow of humidified respiratory gas in a horizontal direction, wherein the humidifier tub further comprises an air inlet conduit extending laterally inwardly from the air inlet opening and an air outlet conduit extending laterally inwardly from the air outlet opening, wherein the air outlet opening and the air inlet opening of the humidifier tub are located on the same planar side wall, wherein the air inlet opening and the air outlet opening of the humidifier tub are coplanar, wherein a central longitudinal axis of the air inlet opening of the humidifier tub is parallel to a central longitudinal axis of the air outlet opening, and wherein the heater plate is located on the lower wall of the cavity of the docking portion.

15. The positive airway device of claim 1, wherein the blower outlet opening and the humidified flow inlet are laterally adjacent to each other, wherein a humidified flow pathway extends through the divider, wherein the blower outlet opening and the humidified flow inlet are positioned at the same height,
wherein the flange is configured to abut a rim of the open lateral side of the cavity when the humidifier tub is fully received by the docking portion,
wherein an outside surface of the second tub subsection is flush with an outside surface of the housing when the humidifier tub is fully received by the docking portion,
wherein the air delivery tube connector is located on a blower portion side of the flow generator,
wherein the air inlet opening of the humidifier tub is configured to receive the pressurized flow of respiratory gas in a horizontal direction,
wherein the air outlet opening of the humidifier tub is configured to discharge the pressurized flow of humidified respiratory gas in a horizontal direction,
wherein the humidifier tub further comprises an air inlet conduit extending laterally inwardly from the air inlet opening and an air outlet conduit extending laterally inwardly from the air outlet opening,
wherein the air outlet opening and the air inlet opening of the humidifier tub are located on the same substantially planar side wall,
wherein the air inlet opening and the air outlet opening of the humidifier tub are coplanar,
wherein a central longitudinal axis of the air inlet opening of the humidifier tub is parallel to a central longitudinal axis of the air outlet opening, and
wherein the heater plate is located on the lower wall of the cavity of the docking portion.

16. The positive airway device of claim 1, wherein the blower outlet opening and the humidified flow inlet are laterally adjacent to each other,
wherein the flange is configured to abut a rim of the open lateral side of the cavity when the humidifier tub is fully received by the docking portion,
wherein an outside surface of the second tub subsection is flush with an outside surface of the housing when the humidifier tub is fully received by the docking portion,
wherein the air inlet opening of the humidifier tub is configured to receive the pressurized flow of respiratory gas in a horizontal direction,
wherein the air outlet opening of the humidifier tub is configured to discharge the pressurized flow of humidified respiratory gas in a horizontal direction,
wherein the humidifier tub further comprises an air inlet conduit extending laterally inwardly from the air inlet opening and an air outlet conduit extending laterally inwardly from the air outlet opening,
wherein the air outlet opening and the air inlet opening of the humidifier tub are located on the same planar side wall,
wherein the air inlet opening and the air outlet opening of the humidifier tub are coplanar,
wherein a central longitudinal axis of the air inlet opening of the humidifier tub is parallel to a central longitudinal axis of the air outlet opening, and
wherein the heater plate is located on the lower wall of the cavity of the docking portion.

17. The positive airway device of claim 1, wherein the blower outlet opening and the humidified flow inlet are laterally adjacent to each other,
wherein the flange is configured to abut a rim of the open lateral side of the cavity when the humidifier tub is fully received by the docking portion,
wherein an outside surface of the second tub subsection is flush with an outside surface of the housing when the humidifier tub is fully received by the docking portion,
wherein the air inlet opening of the humidifier tub is configured to receive the pressurized flow of respiratory gas in a horizontal direction,
wherein the air outlet opening of the humidifier tub is configured to discharge the pressurized flow of humidified respiratory gas in a horizontal direction,
wherein the humidifier tub further comprises an air inlet conduit extending laterally inwardly from the air inlet opening and an air outlet conduit extending laterally inwardly from the air outlet opening,
wherein a central longitudinal axis of the air inlet opening of the humidifier tub is parallel to a central longitudinal axis of the air outlet opening, and
wherein the heater plate is located on the lower wall of the cavity of the docking portion.

18. The positive airway device of claim 1, wherein a humidified flow pathway extends through the divider,
wherein the flange is configured to abut a rim of the open lateral side of the cavity when the humidifier tub is fully received by the docking portion,
wherein an outside surface of the second tub subsection is flush with an outside surface of the housing when the humidifier tub is fully received by the docking portion,
wherein the air delivery tube connector is located on a blower portion side of the flow generator,
wherein the air inlet opening of the humidifier tub is configured to receive the pressurized flow of respiratory gas in a horizontal direction,
wherein the air outlet opening of the humidifier tub is configured to discharge the pressurized flow of humidified respiratory gas in a horizontal direction,
wherein the humidifier tub further comprises an air inlet conduit extending laterally inwardly from the air inlet opening and an air outlet conduit extending laterally inwardly from the air outlet opening,
wherein the air outlet opening and the air inlet opening of the humidifier tub are located on the same planar side wall,
wherein the air inlet opening and the air outlet opening of the humidifier tub are coplanar, and
wherein a central longitudinal axis of the air inlet opening of the humidifier tub is parallel to a central longitudinal axis of the air outlet opening.

19. A positive airway device configured to deliver a pressurized flow of humidified respiratory gas to a patient's airways, the positive airway device comprising:
a flow generator comprising:
a blower portion comprising a blower configured to pressurize the flow of respiratory gas;
a docking portion laterally adjacent to the blower portion, the docking portion being separated from the blower portion by a divider, the docking portion comprising a cavity bound by the divider, a lower wall extending horizontally from the divider, an upper wall opposite the lower wall, and a pair of opposing side walls adjacent to the divider and extending to the upper wall, the cavity being open on a lateral side opposite the divider;
a blower outlet conduit that terminates at an opening in the divider and is configured to convey the pressurized respiratory gas from the blower to the docking portion;
a heater plate on a lower side of the docking portion;

a housing for the blower portion and the docking portion;

an air delivery tube connector attached to the housing; and a humidified flow conduit located within the housing and configured to convey the pressurized flow of humidified respiratory gas between the docking portion and the air delivery tube connector; and a humidifier tub configured to be laterally received by the docking portion through the open lateral side of the cavity, the humidifier tub comprising:

a first tub subsection comprising an air inlet opening and an air outlet opening;

a second tub subsection laterally adjacent to the first tub subsection;

a flange extending outwardly from an outer surface of the humidifier tub to form a transition between the first and second tub subsections, the humidifier tub being configured so that when the humidifier tub is fully received by the docking portion, the first tub subsection is enclosed within the cavity and the second tub subsection remains outside the cavity; and a tub base forming a bottom side of the humidifier tub and comprising a heat conducting base plate configured to engage the heater plate of the docking portion when the humidifier tub is received within the cavity, wherein the air inlet opening of the humidifier tub is configured to complete a sealed airpath from the blower, through the divider, and into the humidifier tub upon the humidifier tub being fully received by the docking portion, and wherein the air outlet opening of the humidifier tub is configured to complete a sealed airpath from the humidifier tub to the air delivery tube connector.

20. The positive airway device of claim 19, wherein the humidifier tub further comprises a latching projection located on a top side of or above the first tub subsection, and wherein the docking portion comprises a recess and the latching projection of the humidifier tub is configured to engage the recess of the docking portion to releasably secure the humidifier tub to the docking portion.

21. The positive airway device of claim 19, wherein the flange is configured to abut a rim of the open lateral side of the cavity when the humidifier tub is fully received by the docking portion.

22. The positive airway device of claim 19, wherein the air inlet opening of the humidifier tub is configured to receive the pressurized flow of respiratory gas in a horizontal direction.

23. The positive airway device of claim 19, wherein the humidifier tub further comprises an air inlet conduit extending laterally inwardly from the air inlet opening.

24. The positive airway device of claim 19, wherein the heater plate is located on the lower wall of the cavity of the docking portion.

25. The positive airway device of claim 19, wherein the flange is configured to abut a rim of the open lateral side of the cavity when the humidifier tub is fully received by the docking portion, wherein the air inlet opening of the humidifier tub is configured to receive the pressurized flow of respiratory gas in a horizontal direction, wherein the humidifier tub further comprises an air inlet conduit extending laterally inwardly from the air inlet opening, and wherein the heater plate is located on the lower wall of the cavity of the docking portion.

\* \* \* \* \*

UNITED STATES PATENT AND TRADEMARK OFFICE
CERTIFICATE OF CORRECTION

PATENT NO. : 11,844,907 B2
APPLICATION NO. : 17/363040
DATED : December 19, 2023
INVENTOR(S) : Ian Malcolm Smith et al.

It is certified that error appears in the above-identified patent and that said Letters Patent is hereby corrected as shown below:

In the Claims

In Claim 15, Column 21, Line 22, --...the humidifier tub are located on the same substantially planar side wall-- should read --...the humidifier tub are located on the same planar side wall--

Signed and Sealed this
Twenty-seventh Day of August, 2024

Katherine Kelly Vidal
*Director of the United States Patent and Trademark Office*